US007202247B2

(12) United States Patent
Sikorski et al.

(10) Patent No.: US 7,202,247 B2
(45) Date of Patent: Apr. 10, 2007

(54) 1,3-BIS-(SUBSTITUTED-PHENYL)-2-PROPYN-1-ONES AND THEIR USE TO TREAT DISORDERS

(75) Inventors: James A. Sikorski, Atlanta, GA (US); Charles Q. Meng, Alpharetta, GA (US); M. David Weingarten, Cummings, GA (US)

(73) Assignee: AtheroGenics, Inc., Alpharetta, GA (US)

( * ) Notice: Subject to any disclaimer, the term of this patent is extended or adjusted under 35 U.S.C. 154(b) by 50 days.

(21) Appl. No.: 10/325,087

(22) Filed: Dec. 19, 2002

(65) Prior Publication Data

US 2003/0232877 A1 Dec. 18, 2003

Related U.S. Application Data

(60) Provisional application No. 60/341,972, filed on Dec. 19, 2001.

(51) Int. Cl.
*C07C 49/213* (2006.01)
*C07D 213/06* (2006.01)
*C07D 231/02* (2006.01)
*A61K 31/12* (2006.01)

(52) U.S. Cl. ............................ 514/252.01; 514/252.1; 514/256; 514/438; 514/461; 514/465; 544/224; 544/242; 544/335; 546/184; 546/312; 548/146; 548/215; 548/300.1; 549/78; 549/80; 549/406; 549/498

(58) Field of Classification Search .................. 549/78, 549/80, 406, 498; 548/146, 215, 300.1; 546/184, 546/312; 544/224, 242, 335; 514/252.01, 514/252.1, 256, 438, 461, 465, 338
See application file for complete search history.

(56) References Cited

U.S. PATENT DOCUMENTS

| | | | |
|---|---|---|---|
| 4,522,811 | A | 6/1985 | Epstein et al. |
| 5,631,365 | A | 5/1997 | Rosenblum et al. |
| 5,767,115 | A | 6/1998 | Rosenblum et al. |
| 6,069,148 | A | 5/2000 | Schmidt et al. |
| 6,140,343 | A | 10/2000 | DeNinno et al. |
| 6,147,089 | A | 11/2000 | DeNinno et al. |
| 6,147,090 | A | 11/2000 | DeNinno et al. |
| 6,162,445 | A | 12/2000 | Bernardon |
| 6,197,786 | B1 | 3/2001 | DeNinno et al. |
| 6,310,075 | B1 | 10/2001 | DeNinno et al. |
| 6,313,142 | B1 | 11/2001 | Damon et al. |

FOREIGN PATENT DOCUMENTS

| | | |
|---|---|---|
| EP | 0 476 658 | 3/1992 |
| WO | WO 96/08484 | 3/1996 |
| WO | WO 97/33882 | 9/1997 |
| WO | WO 98/04528 | 2/1998 |
| WO | WO 98/35937 | 8/1998 |
| WO | WO 98/40375 | 9/1998 |
| WO | WO 99/14174 | 3/1999 |
| WO | WO 99/14215 | 3/1999 |
| WO | WO 99/15504 | 4/1999 |
| WO | WO 00/17166 | 3/2000 |
| WO | WO 00/18721 | 4/2000 |
| WO | WO 00/18723 | 4/2000 |
| WO | WO 00/18724 | 4/2000 |
| WO | WO 00/38725 | 7/2000 |

OTHER PUBLICATIONS

Sakharova et al., PubMed Abstract (Curr Opin Nephrol Hypertens. 10(6):727-38) Nov. 2001.*
Mannino, PubMed Abstract (Respir Care 48(12):1185-91; discussion 1191-3) Dec. 2003.*
Lee et al., PubMed Abstract (J Neuroimmunol. 98(2):77-88) Aug. 1999.*
Corey et. al., *Tetrahedron Lett.* (1972), 3769-3772.
Endo, A. *J. Lipid Res. 33*, 1569 (1992).
Grundy, S. M. *New Engl. J. Med. 319*, 24 (1988).
Jones, R. and N. Bischofberger, *Antiviral Research*, 27 (1995) 1-17.
Ling and Jones in "Dietary Phytosterols: A Review of Metabolism, Benefits and Side Effects," *Life Sciences*, 57 (3), 195-206 (1995).
Wetterrau, et al. *Science*, 282, Oct. 23, 1998, pp. 751-754.
Van Dinther-Janssen, A.C.H.M. et al., "The VLA-4/VCAM-1 Pathway is Involved in Lymphocyte Adhesion to Endothelium in Rheumatoid Synovium", *Journal of Immunology*, 147(12): 4207-4210, (1991).
Ohkawara, Y. et al., "In Situ Expression of the Cell Adhesion Molecules in Bronchial Tissues from Asthmatics with Air Flow Limitations: In Vivo Evidence of VCAM-1/VLA-4 Interaction in Selective Eosinophil Infiltration", *Am. J. Respir. Cell Mol. Biol.*, 12: 4-12 (1995).
Braunstahl, G.-J. et al., "Nasal Allergen Provocation Induces Adhesion Molecule Expression and Tissue Eosinophilia in Upper and Lower Airways", *J. Allergy Clin. Immunol.*, 107(3): 469-476 (2001).

(Continued)

*Primary Examiner*—Deepak Rao
(74) *Attorney, Agent, or Firm*—King & Spalding

(57) ABSTRACT

The invention relates to compounds, pharmaceutical compositions and methods of using compounds of the general formula

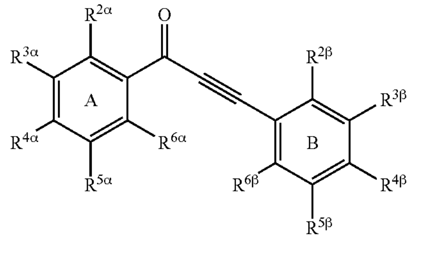

or its pharmaceutically acceptable salt or ester, wherein the substituents are defined in the application.

25 Claims, No Drawings

OTHER PUBLICATIONS

Koga, M. et al., "Relationship Between Circulating Vascular Cell Adhesion Molecule-1 and Microvascular Complications in Type 2 Diabetes Mellitus", *Diabet. Med.*, 15: 661-667 (1998).

Wagner, O.F. et al., "Putative Role of Adhesion Molecules in Metabolic Disorders", *Horm. Metab. Res.*, 29: 627-630 (1997).

Jones, S.M. et al., "VCAM-1 Expression on Endothelium in Lesions from Cutaneous Lupus Erythematosus Is Increased Compared With Systemic and Localized Scleroderma", British *Journal of Dermatology*, 135: 678-686 (1996).

Lee, S.J. et al., "Adhesion Molecule Expression and Regulation on Cells of the Central Nervous System", *Journal of Neuroimmunology*, 98: 77-88 (1999).

Wasserman M.A. et al., "Chemistry and Pharmacology of Vascular Protectants: A Novel Approach to the Treatment of Atherosclerosis and Coronary Artery Disease", *American Journal of Cardiology*, 91: 34A-40A (2003).

* cited by examiner

1,3-BIS-(SUBSTITUTED-PHENYL)-2-PROPYN-1-ONES AND THEIR USE TO TREAT DISORDERS

This application claims priority to U.S. Provisional Patent Application Ser. No. 60/341,972 filed Dec. 19, 2001.

The present invention is in the field of novel 1,3-bis-subsituted-phenyl)-2-propyn-1-ones, pharmaceutical compositions and methods for treating a variety of diseases and disorders, including inflammation and cardiovascular disease.

BACKGROUND OF THE INVENTION

Adhesion of leukocytes to the endothelium represents a fundamental, early event in a wide variety of inflammatory conditions, autoimmune disorders and bacterial and viral infections. Leukocyte recruitment to endothelium is mediated in part by the inducible expression of adhesion molecules on the surface of endothelial cells that interact with counterreceptors on immune cells. Endothelial cells determine which types of leukocytes are recruited by selectively expressing specific adhesion molecules, such as vascular cell adhesion molecule-1 (VCAM-1), intercellular adhesion molecule-1 (ICAM-1), and E-selectin. VCAM-1 binds to the integrin VLA-4 expressed on lymphocytes, monocytes, macrophages, eosinophils, and basophils but not neutrophils. This interaction facilitates the firm adhesion of these leukocytes to the endothelium. VCAM-1 is an inducible gene that is not expressed, or expressed at very low levels, in normal tissues. VCAM-1 is upregulated in a number of inflammatory diseases, including arthritis (including rheumatoid arthritis), asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

Coronary heart disease (CHD), primarily as a result of atherosclerosis, remains the leading cause of death in industrialized countries. Atherosclerosis is a disease characterized by vascular inflammation, deposition of lipids in the arterial vessel wall and smooth muscle cell proliferation resulting in a narrowing of the vessel passages. In advanced stages of the disease atherosclerotic lesions can become unstable resulting in plaque rupture, thrombosis, myocardial infarction and ischemic heart disease. It is now well accepted that the initiating events in atherosclerosis are local injury to the arterial endothelium that results in the induction of VCAM-1 and recruitment of mononuclear leukocytes that express the integrin counterreceptor, VLA-4, (O'Brien, et al., *J. Clin. Invest.*, 92: 945–951, 1993). Subsequent conversion of leukocytes to foamy macrophages results in the synthesis of a wide variety of inflammatory cytokines, growth factors, and chemoattractants that help propagate formation of the mature atheromatous plaque by further inducing endothelial activation, leukocyte recruitment, smooth muscle cell proliferation, and extracellular matrix deposition. Pharmacological inhibition of VCAM-1 expression has been shown to inhibit atherosclerosis in several animal models (Sundell et al., *Circulation,* 100: 42, 1999). A monoclonal antibody against VCAM-1 has also been shown to inhibit neointimal formation in a mouse model of arterial wall injury (Oguchi, S., et al., *Arterioscler. Thromb. Vasc. Biol.,* 20: 1729–1736, 2000).

Asthma, which is increasing in prevalence and morbidity world-wide, is a chronic inflammatory disease characterized by lung eosinophilia and bronchial hyperreactivity. The interaction between VCAM-1 on lung endothelial cells and VLA-4, which is the integrin counterreceptor expressed on eosinophils, is thought to be important for selective eosinophil recruitment. Eosinophils have been considered an important effector cell in the pathogenesis of asthma and other allergic diseases. Activated eosinophils release proteins such as major basic protein (MBP) that have been demonstrated to induce bronchial hyperreactivity, one of the defining criteria of asthma (Bousquot, et al., *N. Engl. J. Med.,* 323: 1033–1039, 1990). It has been demonstrated that VCAM-1 is markedly upregulated on human bronchial vascular endothelium of subjects with asthma who have air flow limitation, when compared with subjects without asthma (Pilewski, et al., *Am. J. Respir. Cell Mol. Biol.,* 12, 1–3, 1995; Ohkawara, Y., et al., *Am. J. Respir. Cell Mol. Biol.,* 12, 4–12, 1995; Gosset, P., et al., *Int. Arch. Allergy Immunol.* 106: 69–77, 1995; Hacken, N. H., et al., *Clin. Exp. Allergy,* 28 (12): 1518–1525, 1998). An elevation in serum soluble VCAM-1 levels has also been demonstrated in patients undergoing a bronchial asthma attack compared with levels under stable conditions (Montefort, S., Koizumi, A., *Clin. Exp. Immunol.,* 101: 468–73, 1995). Several animal studies further demonstrate a spatial and temporal association between VCAM-1 and asthma. In a mouse model of allergic asthma, VCAM-1 expression was shown to be induced by allergen challenge, and administration of an anti-VCAM-1 antibody was effective in inhibiting eosinophil infiltration that occurred in this model (Metzger, W. J., et al., *J. Allergy Clin. Immunol.,* 93: 183, 1994). Further evidence for the importance of VCAM-1 in allergic asthma comes from work in IL-12 knockout mice. IL-12 knockout mice had fewer eosinophils and VCAM-1 expression than wildtype mice; however, administration of recombinant IL-12 at the time of ova sensitization and challenge restored lung VCAM-1 expression and eosinophilia (Wang, S., et al., *J. Immunol.,* 166:2741–2749, 2001). There are several examples where blocking the integrin receptors for VCAM-1 have had positive effects on animal models of asthma (Rabb et al., *Am. J. Respir. Care Med.* 149: 1186–1191, 1994; Abraham, W, et al., *Am. J. Respir. Crit. Care Med.* 156: 696–703. 1997) further demonstrating the importance of VCAM-1/VLA-4 interactions in allergic inflammation. Eosinophils are also important effector cells in allergic rhinitis. VCAM-1 has been demonstrated to be upregulated 24 hrs after nasal allergen provocation in patients with seasonal allergic rhinitis but not in normal subjects (Braunstahl, G. J., et al., *J. Allergy Clin. Immunol.,* 107: 469–476, 2001).

Rheumatoid arthritis (RA) is a clinical syndrome of unknown cause characterized by symmetric, polyarticular inflammation of synovial-lined joints. The role of adhesion molecules in the pathogenesis of RA has also been well documented, and VCAM-1 expression on synovial fibroblasts is a clinical hallmark of RA (Li, P., et al., *J. Immunol.* 164: 5990–7, 2000). VLA-4/VCAM-1 interactions may be the predominant mechanism for recruitment of leukocytes to the synovium (Dinther-Janssen, et al., *J. Immunol.* 147: 4207–4210, 1991; Issekeutz and Issekeutz, *Clin. Immunol. Immunopathol.* 61:436–447, 1991; Morales-Ducret et al., *J. Immunol.* 149:1424–1431, 1992; Postigo et al., *J. Clin. Invest.* 89:1445–1452, 1992; Matsuyama, T., et al, *Hum.*

*Cell,* 9: 187–192, 1996). In support of this, increased VCAM-1 expression has been found in RA synovial tissue compared with osteoarthritis and control tissue (Wilkinson et al., *Lab. Invest.* 69:82–88, 1993; Furuzawa-Carballeda, J., et al., *Scand. J. Immunol.* 50: 215–222; 1999). Soluble VCAM-1 is higher in RA patients than in control subjects (Kolopp-Sarda, M. N., et al., *Clin. Exp. Rheumatol.* 19: 165–70, 2001). Soluble VCAM-1 has been shown to be chemotactic for T cells (Kitani, A., et al., *J. Immun.* 161: 4931–8, 1998), and in addition to being a possible diagnostic marker for RA, may contribute to its pathogenesis by inducing migration and recruitment of T cells. VCAM-1 expressed on fibroblast-like synoviocytes has also been implicated in enhanced survival of activated synovial fluid B cells (Marinova, Mutafcheia, L., *Arthritis Rheum.* 43: 638–644, 2000) that may further contribute to RA pathogenesis.

Chronic inflammation and accompanying vascular complications and organ damage characterize systemic lupus erythematosis (SLE). Recent studies suggest that VCAM-1 plays a role in SLE. Expression of VCAM-1 is increased on dermal vessel endothelial cells in patients with active systematic lupus erythematosus (Jones, S. M., *British J. Dermatol.* 135: 678–686, 1996) and correlates with increased disease severity (Belmont et al., *Arthritis Rheum.* 37:376–383, 1994). SLE muscle samples with perivascular infiltrate have greater endothelial cell expression of VCAM-1 compared with SLE patients without a perivascular infiltrate or with control samples (Pallis et al., *Ann. Rheum. Dis.* 52:667–671, 1993). Increased expression of VCAM-1 has also been demonstrated in kidneys of lupus-prone MRL/lpr mice compared to nonautoimmune strains and its expression increased with disease severity (McHale, J. F., et al., *J. Immunol.* 163: 3993–4000, 1999). VCAM-1 expression on mesangial cells in vitro can be stimulated by IL-1, TNF-α, and INFγ exposure as well as by anti-endothelial cell IgG fraction and anti-DNA autoantibodies from SLE patients (Wuthrich, *Kidney Int.* 42: 903–914, 1992; Papa, N. D., et al., *Lupus,* 8: 423–429, 1999; Lai, K. N., et al., *Clin Immunol Immunopathol,* 81: 229–238, 1996). Furthermore, soluble VCAM-1 is higher in SLE patients than in normal subjects (Mrowka, C., et al., *Clin. Nephrol.* 43: 288–296, 1995; Baraczka, K., et al., *Acta. Neurol. Scand.* 99: 95–99, 1999; Kaplanski, G., et al., *Arthritis Rheumol.* 43: 55–64, 2000; Ikeda, Y., *Lupus,* 7: 347–354, 1998) and correlates with disease activity (Scudla, V., *Vnitr. Lek.,* 43: 307–311, 1997).

Increased VCAM-1 expression has also been demonstrated in solid organ transplant rejection. Acute transplant rejection occurs when the transplant recipient recognizes the grafted organ as "non-self" and mounts an immune response characterized by massive infiltration of immune cells, edema, and hemorrage that result in the death of the transplanted organ. Acute rejection occurs in a matter of hours or days and has been correlated with increased levels of VCAM-1 in tissues and in plasma (Tanio et al., *Circulation,* 89:1760–1768, 1994; Cosimi et al., *J. Immunol.* 144: 4604–4612, 1990; Pelletier, R., et al., *Transplantation,* 55: 315, 1992). A monoclonal antibody to VCAM-1 has been shown to inhibit cardiac allograft rejection in mice (Pelletier, R., *J. Immunol.,* 149: 2473–2481, 1992; Pelletier, R., et al., *Transplantation Proceedings,* 25: 839–841, 1993; Orosz, C. G., et al., *J. Heart and Lung Transplantation,* 16: 889–904, 1997) and when given for 20 days can cause complete inhibition of rejection and long-term graft acceptance (Orosz C. G., et al., *Transplantation,* 56: 453–460, 1993). Chronic graft rejection also known as allograft vasculopathy is distinct from acute transplant rejection and is a leading cause of late graft loss after renal and heart transplantation. Histologically it is characterized by concentric neointimal growth within vessels that is largely due to smooth muscle migration and proliferation. It is thought to be the result of endothelial damage brought about by several factors including: ischemia-reperfusion injury, immune complexes, hypertension, hyperlipidemia and viruses. All of these factors have been associated with induction of VCAM-1 in endothelial cells. There is also a strong correlation of soluble and tissue VCAM-1 levels with chronic rejection (Boratynska, M., *Pol. Arch. Med. Wewn,* 100: 410–410, 1998; Zembala, M., et al., *Ann. Transplant.* 2: 16–9, 1998; Solez K., et al., *Kidney International.,* 51: 1476–1480, 1997; Koskinen P. K., et al., *Circulation,* 95: 191–6, 1997).

Multiple sclerosis is a common demyelinating disorder of the central nervous system, causing patches of sclerosis (plaques) in the brain and spinal cord. It occurs in young adults and has protean clinical manifestations. It is well documented that VCAM-1 is expressed on brain microvascular endothelial cells in active lesions of multiple sclerosis (Lee S. J., et al., *J. Neuroimmunol.,* 98: 77–88, 1998). Experimental therapy of experimental autoimmune encephalomyelitis, which is an animal model for; multiple sclerosis, using antibodies against several adhesion molecules, including VCAM-1, clearly shows that adhesion molecules are critical for the pathogenesis of the disease (Benveniste et al., *J. Neuroimmunol.* 98:77–88, 1999). A time and dose dependent expression of VCAM-1 and release of soluble VCAM-1 were detected in cultures of human cerebral endothelial cells induced by TNFα, but not in peripheral blood mononuclear cells (Kallmann et al., *Brain,* 123:687–697, 2000). Clinical data also show that adhesion molecules in blood and cerebrospinal fluid are up-regulated throughout the clinical spectrum of multiple sclerosis (Baraczka, K., et al., *Acta. Neurol. Scand.* 99: 95–99, 1999; Reickmann, P., et al., *Mult. Scler.,* 4: 178–182, 1998; Frigerio, S., et al., *J. Neuroimmunol.,* 87: 88–93, 1998) supporting the notion that therapies which interfere with cell adhesion molecules such as VCAM-1 may be beneficial in modifying this disease (Elovaara et al., *Arch. Neurol.* 57:546–551, 2000).

Diabetes mellitus is a metabolic disease in which carbohydrate utilization is reduced and that of lipid and protein is enhanced. Evidence has accumulated that increased levels of adhesion molecules may play a functional pathophysiological role in diabetes (Wagner and Jilma, *Hormone and Metabolic Research,* 29: 627–630, 1997; Kado, S., *Diabetes Res. Clin. Pract.,* 46: 143–8, 1999). It is caused by an absolute or relative deficiency of insulin and is characterized by chronic hyperglycemia, glycosuria, water and electrolyte loss, ketoacidosis, and coma. Elevated circulating adhesion molecules including VCAM-1 have been detected in patients with diabetes and in experimental models of diabetes in animals (Lorini et al., *Hormone Research,* 48: 153, 1997; Otsuki et al., *Diabetologia,* 40: A440, 1997; Hart et al., *FASEB J.* 11:A340, 1997; Albertini et al., *Diabetologia,* 39: A240, 1996; Wagner et al., *Diabetologia,* 39: A205, 1996; Enghofer et al., *Diabetologia,* 39: A97, 1996; Koga M., *Diabet. Med.,* 15: 661–667, 1998). In addition, complications of diabetes often include peripheral vasculopathies such as diabetic retinopathy and diabetic nephropathy. It is believed that adhesion of leukocytes to the peripheral vasculature plays a central role in the vasculopathies often associated with diabetes.

Crohn's disease, also known as regional enteritis, is a subacute chronic inflammatory condition of unknown cause, involving the internal ileum and less frequently other parts of the gastrointestinal tract. It is characterized by patchy deep ulcers that may cause fistulas, and narrowing and thickening of the bowel by fibrosis and lymphocytic infiltration. Ulcerative colitis is a chronic disease of unknown cause characterized by ulceration of the colon and rectum, with rectal bleeding, mucosal crypt abscesses, inflammatory pseudopolyps, abdominal pain, and diarrhea. It has been reported that serum VCAM-1 reflects the grade of intestinal inflammation in patients with Crohn's disease or ulcerative colitis (Jones, et al., *Gut,* 36: 724–30, 1995; Goggins et al., *Gastroenterology,* 108: A825, 1995; Goeke and Manns, *Gastroenterology,* 106: A689, 1994; Goeke et al., *J. Gasterokenterol.* 32:480–486, 1997; Loftus et al., *Gastroenterology,* 108: A684, 1995; Tahami et al., *Gastroenterology,* 118: A344, 2000). Antibodies to VCAM-1 have been shown to ameliorate experimentally-induced colitis in mice (Soriano, A., *Lab. Invest.* 80: 1541–1551, 2000).

Psoriasis is a chronic skin disease characterized by erythematous scaling plaques as a result of keratinocyte hyperplasia, influx of immune cells and endothelial activation (Nickoloff, B. J., et al., *J. Invest. Dermatol.,* 127: 871–884, 1991). VCAM-1 is upregulated in psoriatic skin as compared to normal skin (Groves, R. W., *J. Am. Acad. Dermatol.,* 29: 67–72, 1993; Uyemura, K., et al., *J. Invest. Dermatol.* 101: 701–705, 1993) and levels of circulating VCAM-1 correlate with disease activity (Schopf, R. E., *Br. J. Dermatol.,* 128: 34–7, 1993).

Given that VCAM-1 is a mediator of chronic inflammatory disorders, it is a goal of the present work to identify new compounds, compositions and methods that can inhibit the expression of VCAM-1. A more general goal is to identify selective compounds and methods for suppressing the expression of redox sensitive genes or activating redox sensitive genes that are suppressed. An even more general goal is to identify selective compounds, pharmaceutical compositions and methods of using the compounds for the treatment of inflammatory diseases.

It is therefore an object of the present invention to provide new compounds for the treatment of disorders mediated by VCAM-1.

It is also an object to provide new pharmaceutical compositions for the treatment of diseases and disorders mediated by the expression of VCAM-1.

It is a further object of the invention to provide compounds and methods of treating disorders and diseases mediated by VCAM-1, including cardiovascular and inflammatory diseases.

It is another object of the invention to provide compounds, compositions and methods to treat arthritis.

Another object of the invention is to provide compounds, compositions and methods to treat rheumatoid arthritis. The inventions compounds, compositions and methods are also suitable as disease modifying anti-rheumatoid arthritis drugs (DMARDs).

It is yet another object of the invention to provide compounds, compositions and methods to treat asthma.

It is another object of the invention to provide compounds, methods and compositions to inhibit the progression of atherosclerosis.

It is still another object of the invention to provide compounds, compositions, and methods to treat or prevent transplant rejection.

It is a further object of the present invention to provide compounds, methods and compositions for the treatment of lupus.

It is a further object of the present invention to provide compounds, methods and compositions for the treatment of inflammatory bowel disease.

It is a further object of the present invention to provide compounds, methods and compositions for the treatment of autoimmune diabetes.

It is a further object of the present invention to provide compounds, methods and compositions for the treatment of multiple sclerosis.

It is a further object of the present invention to provide compounds, methods and compositions for the treatment of diabetic retinopathy.

It is a further object of the present invention to provide compounds, methods and compositions for the treatment of diabetic nephropathy.

It is a further object of the present invention to provide compounds, methods and compositions for the treatment of diabetic vasculopathy.

It is a further object of the present invention to provide compounds, methods and compositions for the treatment of rhinitis.

It is a further object of the present invention to provide compounds, methods and compositions for the treatment of ischemia-reperfusion injury.

It is a further object of the present invention to provide compounds, methods and compositions for the treatment of post-angioplasty restenosis.

It is a further object of the present invention to provide compounds, methods and compositions for the treatment of chronic obstructive pulmonary disease (COPD).

It is a further object of the present invention to provide compounds, methods and compositions for the treatment of glomerulonephritis.

It is a further object of the present invention to provide compounds, methods and compositions for the treatment of Graves disease.

It is a further object of the present invention to provide compounds, methods and compositions for the treatment of gastrointestinal allergies.

It is a further object of the present invention to provide compounds, methods and compositions for the treatment of conjunctivitis.

It is a further object of the present invention to provide compounds, methods and compositions for the treatment of dermatitis.

It is a further object of the present invention to provide compounds, methods and compositions for the treatment of psoriasis.

SUMMARY OF THE INVENTION

Examples of inflammatory disorders that are mediated by VCAM-1 include, but are not limited to arthritis, asthma, dermatitis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

The compounds disclosed herein can also be used in the treatment of inflammatory skin diseases that are mediated by VCAM-1, as well as human endothelial disorders that are mediated by VCAM-1, which include, but are not limited to psoriasis, dermatitis, including eczematous dermatitis, Kaposi's sarcoma, multiple sclerosis, as well as proliferative disorders of smooth muscle cells.

In yet another embodiment, the compounds disclosed herein can be selected to treat anti-inflammatory conditions that are mediated by mononuclear leucocytes.

In one embodiment, the compounds of the present invention are selected for the prevention or treatment of tissue or organ transplant rejection. Treatment and prevention of organ or tissue transplant rejection includes, but is not limited to treatment of recipients of heart, lung, combined heart-lung, liver, kidney, pancreatic, skin, spleen, small bowel, or corneal transplants. The compounds can also be used in the prevention or treatment of graft-versus-host disease, such as sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

Compounds of the present invention are of the formula

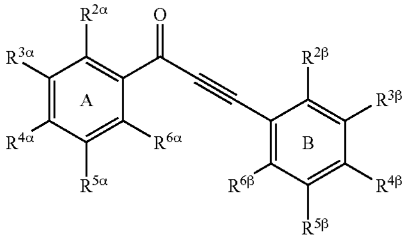

or its pharmaceutically acceptable salt or ester, wherein the substituents are defined herein.

DETAILED DESCRIPTION OF THE INVENTION

It has been discovered that compounds of the invention inhibit the expression of VCAM-1, and thus can be used to treat a patient with a disorder mediated by VCAM-1. These compounds can be administered to a host as monotherapy, or if desired, in combination with another compound of the invention or another biologically active agent, as described in more detail below.

In a 1st embodiment, the invention is represented by Formula I:

(I)

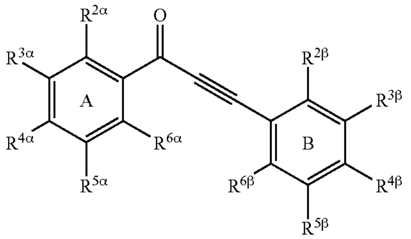

or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —$C(O)R^2$, —$COOR^1$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{2\beta}$, $R^{3\beta}$, $R^{4\beta}$, $R^{5\beta}$ or $R^{6\beta}$, or one of $R^{2\alpha}$, $R^{3\alpha}$, $R^{4\alpha}$, $R^{5\alpha}$ or $R^{6\alpha}$ must be a carbon-carbon linked heterocycle or heteroaryl; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $—OC(R^1)_2COOH$; and/or at least one of $R^{2\alpha}$, $R^{3\alpha}$, $R^{4\alpha}$, $R^{5\alpha}$, $R^{6\alpha}$ or one of $R^{2\beta}$, $R^{3\beta}$, $R^{4\beta}$, $R^{5\beta}$, $R^{6\beta}$ must be selected from the group consisting of carboxy, cyano, tetrazol-5-yl, $—C(O)OR^2$, $—C(O)NHR^2$, $—C(O)NH_2$, $—C(O)N(R^2)_2$, $—C(CH_3)_2C(O)OH$, $—CH_2C(O)OH$, $—NHR_2$, $NH_2$, $—NHSO_2R^2$, $N(R^2)_2$, $—NR^2SO_2R^2$, $—NHSO_2NHR^2$, $—NHC(O)R^2$, $—NHC(O)OR^2$, $—SCH_2CO_2H$, $—SCF_2CO_2H$, —SH, $—SR^2$, $—NR^2C(O)R^2$, $—NHC(O)SR^2$, $NHC(O)NHR^2$, $—NHC(O)N(R^2)_2$, $SC(R^2)_2COOH$, $—SO_2NH_2$, $—SO_2NHR^2$, $—SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 2nd embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR_2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{2\beta}$, $R^{3\beta}$, $R^{4\beta}$, $R^{5\beta}$ or $R^{6\beta}$, or one of $R^{2\alpha}$, $R^{3\alpha}$, $R^{4\alpha}$, $R^{5\alpha}$ or $R^{6\alpha}$ must be a carbon-carbon linked heterocycle or heteroaryl; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a heterocycle or heteroaryl substituted by one or more hydroxyalkyl or aminoalkyl and optionally, substituted with one or more selected from the group consisting of hydroxy, alkyl, carboxy, hydroxyalkyl, carboxyalkyl, amino, cyano, alkoxy, alkoxycarbonyl, acyl, oxo, and halo and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $—OC(R^1)_2COOH$; and/or at least one of $R^{2\alpha}$, $R^{3\alpha}$ $R^{4\alpha}$ or one of $R^{2\beta}$, $R^{3\beta}$, $R^{4\beta}$ must be selected from the group consisting of carboxy, cyano, tetrazol-5-yl, $—C(O)OR^2$, $—C(O)NHR^2$, $—C(O)NH_2$, $—C(O)N(R^2)_2$, $—C(CH_3)_2C(O)OH$, $—CH_2C(O)OH$, $—NHR^2$, $NH_2$, $—NHSO_2R^2$, $N(R^2)_2$, $—NR^2SO_2R^2$, $—NHSO_2NHR^2$, $—NHC(O)R^2$, $—NHC(O)OR^2$, $—SCH_2CO_2H$, $—SCF_2CO_2H$, —SH, $—SR^2$, $—NR^2C(O)R^2$, $—NHC(O)SR^2$, $NHC(O)NHR^2$, $—NHC(O)N(R^2)_2$, $SC(R^1)_2COOH$, $—SO_2NH_2$, $—SO_2NHR^2$, $—SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 3rd embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycloamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —NHC(O)$NHR^2$, and —NHC(O)$N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{2\beta}$, $R^{3\beta}$, $R^{4\beta}$, $R^{5\beta}$ or $R^{6\beta}$ must be a carbon-carbon linked heterocycle or heteroaryl; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- or 6-membered ring containing one nitrogen, which may optionally be substituted with one or more selected from the group consisting of hydroxy alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$, $R^{6\beta}$ cannot be —$OC(R^1)_2COOH$; and/or at least one of $R^{2\alpha}$, $R^{3\alpha}$, $R^{4\alpha}$, $R^{5\alpha}$, or $R^{6\alpha}$ must be selected from the group consisting of carboxy, carboxyalkoxy, cyano, tetrazol-5-yl, —C(O)$OR^2$, —C(O)$NHR^2$, —C(O)$NH_2$, —C(O)$N(R^2)_2$, —$C(CH_3)_2C(O)OH$, —$CH_2C(O)OH$, —$NHR^2$, $NH_2$, —$NHSO_2R^2$, $N(R^2)_2$, —$NR^2SO_2R^2$, —$NHSO_2NHR^2$, —NHC(O)$R^2$, —NHC(O)$OR^2$, —$SCH_2CO_2H$, —$SCF_2CO_2H$, —SH, —$SR^2$, —$NR^2C(O)R^2$, —NHC(O)$SR^2$, NHC(O)$NHR^2$, —NHC(O)$N(R^2)_2$, $SC(R^1)_2COOH$, —$SO_2NH_2$, —$SO_2NHR^2$, —$SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 4th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —C(O)$R^2$, —$COOR^1$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —C(O)$NH_2$, C(O)$NHR^2$, —C(O)$N(R^2)_2$, —NHC(O)$R^2$, —$N(R^2)C(O)R^2$, —NHC(O)$OR^2$, —NHC(O)$SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —NHC(O)$NHR^2$, and —NHC(O)$N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —$OC(R^1)_2COOH$; and/or at least one of $R^{2\alpha}$, $R^{3\alpha}$, or $R^{4\alpha}$ must be selected from the group consisting of carboxy, carboxyalkoxy, cyano, tetrazol-5-yl, —C(O)$OR^2$, —C(O)$NHR^2$, —C(O)$NH_2$, —C(O)$N(R^2)_2$, —$C(CH_3)_2C(O)OH$, —$CH_2C(O)OH$, —$NHR^2$, $NH_2$, —$NHSO_2R^2$, $N(R^2)_2$, —$NR^2SO_2R^2$, —$NHSO_2NHR^2$, —NHC(O)$R^2$, —NHC(O)$OR^2$, —$SCH_2CO_2H$, —$SCF_2CO_2H$, —SH, —$SR^2$, —$NR^2C(O)R^2$, —NHC(O)$SR^2$, NHC(O)$NHR^2$, —NHC(O)$N(R^2)_2$, $SC(R^1)_2COOH$, —$SO_2NH_2$, —$SO_2NHR^2$, —$SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 5th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —OC$(R^1)_2$COOH, —SC$(R^1)_2$COOH, —NHC$(R^1)_2$COOH, —C(O)$R^2$, —COO$R^1$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —C(O)$NH_2$, —C(O)NH$R^2$, —C(O)N$(R^2)_2$, —NHC(O)$R^2$, —N$(R^2)$C(O)$R^2$, —NHC(O)O$R^2$, —NHC(O)S$R^2$, —NH$SO_2$NH$R^2$, —$SO_2NH_2$, —$SO_2NHR_2$, —$SO_2N(R^2)_2$, —$PO_2H_2$, —$PO_3H_2$, P$(R^2)O_2$H, —$SCF_2CO_2H$, —NH$SO_2R^2$, —N(C(O)NH$R^2)_2$, —NR $SO_2R^2$, —NHC(O)NH$R^2$, and —NHC(O)N$(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl; and/or at least one of $R^{2\alpha}$, $R^{3\alpha}$, or $R^{4\alpha}$ must be selected from the group consisting of carboxy, carboxyalkoxy, cyano, tetrazol-5-yl, —C(O)O$R^2$, —C(O)NH$R^2$, —C(O)$NH_2$, —C(O)N$(R^2)_2$, —C$(CH_3)_2$C(O)OH, —$CH_2$C(O)OH, —NH$R^2$, $NH_2$, —NH$SO_2R^2$, N$(R^2)_2$, —N$R^2SO_2R^2$, —NH$SO_2$NH$R^2$, —NHC(O)$R^2$, —NHC(O)O$R^2$, SC$(R^1)_2$COOH, —$SCH_2CO_2H$, —$SCF_2CO_2H$, —SH, —S$R^2$, —N$R^2$C(O)$R^2$, —NHC(O)S$R^2$, NHC(O)NH$R^2$, —NHC(O)N$(R^2)_2$, —$SO_2NH_2$, —$SO_2$NH$R^2$, —$SO_2N(R^2)_2$, and N$R^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 6th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, aryloxy, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —OC$(R^1)_2$COOH, —SC$(R^1)_2$COOH, —NHC$(R^1)_2$COOH, —C(O)$R^2$, —COO$R^2$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —C(O)$NH_2$, —C(O)NH$R^2$, —C(O)N$(R^2)_2$, —NHC(O)$R^2$, —N$(R^2)$C(O)$R^2$, —NHC(O)O$R^2$, —NHC(O)S$R^2$, —NH$SO_2$NH$R^2$, —$SO_2NH_2$, —$SO_2NHR_2$, —$SO_2N(R^2)_2$, —$PO_2H_2$, —$PO_3H_2$, P$(R^2)O_2$H, —$SCF_2CO_2H$, —NH$SO_2R^2$, —N(C(O)NH$R^2)_2$, —N$R^2SO_2R^2$, —NHC(O)NH$R^2$, and —NHC(O)N$(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl; and/or that at least one of $R^{2\alpha}$, $R^{3\alpha}$, or $R^{4\alpha}$ must be selected from the group consisting of carboxy, carboxyalkoxy, cyano, tetrazol-5-yl, —C(O)O$R^1$, —C(O)NH$R^2$, —C(O)$NH_2$, —C(O)N$(R^2)_2$, —C$(CH_3)_2$C(O)OH, —$CH_2$C(O)OH, —$SCH_2CO_2H$, SC$(R)_2$COOH, and —$SCF_2CO_2H$.

In a 7th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy carbocycle, aryl, heteroaryl, heterocycle, cycloalkyl, cyano, alkoxy, lower alkoxy, aryloxy, arylalkoxy, heteroaryloxy, heteroarylalkoxy, alkylthio, alkylamino, aminoalkyl, haloalkylthio, acyl, haloalkyl, aryloxy, acylamino, amino, dialkylamino, haloalkoxy, alkylsulfonyl, haloalkylsulfonyl, halogen, thiol, nitro, alditol, carbohydrate, $—OC(R^1)_2COOH$, $—SC(R^1)_2COOH$, $—NHC(R^1)_2COOH$, $—C(O)R^2$, $—COOR^2$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of carboxy, carboxyalkoxy, cyano, tetrazol-5-yl, $—C(O)OR^2$, $—C(O)NHR^2$, $—C(O)NH_2$, $—C(O)N(R^2)_2$, $—C(CH_3)_2C(O)OH$, $—CH_2C(O)OH$, $SC(R^1)_2COOH$, and $—SCH_2CO_2H$.

In an 8th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy heteroaryl, heterocycle, cycloalkyl, cyano, alkoxy, lower alkoxy, aryloxy, arylalkoxy, heteroaryloxy, heteroarylalkoxy, alkylthio, alkylamino, aminoalkyl, haloalkylthio, acylamino, acyl, haloalkyl, aryloxy, acylamino, amino, dialkylamino, haloalkoxy, halogen, alditol, carbohydrate, $—COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heterocyclo lower alkoxy, heterocycleoxy, heterocyclo lower alkyl, heterocyclothio lower alkyl, heteroarylamino lower alkyl, heterocycloamino lower alkyl, arylamino, heterocycleamino, heteroarylamino, cycloalkylamino, heterocyclealkoxy, cycloalkyloxy, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, hydroxyalkyl, aminoalkyl, amino, alkoxy, acyl, alkoxycarbonyl, oxo, and halo;

$R^1$ is selected from the group consisting of hydrogen, lower alkyl, and cycloalkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is selected from the group consisting of alkyl, lower alkyl, aryl, heteroaryl, heterocycle, arylalkyl; heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of carboxy, carboxyalkoxy, tetrazol-5-yl, $—C(O)NHR^2$, $—C(O)NH_2$, $—SCH_2CO_2H$ and $—C(O)N(R^2)_2$.

In a 9th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, hydroxyl, carboxy, heteroaryl, heterocycle, cycloalkyl, alkoxy, lower alkoxy, alkylthio, alkylamino, aminoalkyl, acylamino, amino, dialkylamino, halogen, polyol alkyl, hydroxyalkyl, heterocyclo lower alkoxy, heterocycleoxy, heterocyclo lower alkyl, arylamino, heterocycleamino, heteroarylamino, cycloalkylamino, heterocyclealkoxy, cycloalkyloxy, $—NHC(O)R^2$, $—N(R^2)C(O)R^2$, $—NHC(O)OR^2$, $—NHC(O)SR^2$, $—NHSO_2NHR^2$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, lower alkyl, hydroxyalkyl, aminoalkyl, amino, acyl, alkoxycarbonyl, and halo;

$R^2$ is selected from the group consisting of alkyl, lower alkyl, aryl, heteroaryl, and heterocycle, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of carboxy, carboxyalkoxy, tetrazol-5-yl, $—C(O)NHR^2$, and $—C(O)NH_2$.

In a 10th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, lower alkyl, carboxy, heteroaryl, heterocycle, alkoxy, lower alkoxy, alkylamino, amino, dialkylamino, halogen, and $—NHSO_2R^2$, all of which can be optionally substituted by one or more selected from the group consisting of hydroxy, lower alkyl, hydroxyalkyl, aminoalkyl, amino, and halo;

$R^2$ is selected from the group consisting of lower alkyl, and aryl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of carboxy, carboxyalkoxy, and tetrazol-5-yl.

In an 11th embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, lower alkyl, carboxy, heteroaryl, heterocycle, lower alkoxy, dialkylamino, and halogen, all of which can be optionally substituted by one or more selected from the group consisting of hydroxy, lower alkyl, hydroxyalkyl, aminoalkyl, amino, acyl, alkoxycarbonyl, and halo;

$R^{2\beta}$, $R^{3\beta}$, $R^{4\beta}$, $R^{5\beta}$ and $R^{6\beta}$ are independently selected from the group consisting of hydrogen, lower alkyl, carboxy, heteroaryl, heterocycle, lower alkoxy, dialkylamino, and halogen, all of which can be optionally substituted by one or more selected from the group consisting of hydroxy, lower alkyl, hydroxyalkyl, aminoalkyl, amino, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be carboxy or carboxyalkoxy.

In a 12th embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, lower alkyl, carboxy, carboxyalkoxy, lower alkoxy, and halogen;

$R^{2\beta}$, $R^{3\beta}$, $R^{4\beta}$, $R^{5\beta}$ and $R^{6\beta}$ are independently selected from the group consisting of hydrogen, lower alkyl, heteroaryl, heterocycle, lower alkoxy, dialkylamino, and halogen all of which can be optionally substituted by one or more selected from the group consisting of hydroxy, methyl, hydroxymethyl, aminomethyl, amino, acyl, alkoxycarbonyl, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be carboxy.

In a 13th embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, lower alkyl, carboxy, carboxyalkoxy, lower alkoxy, and halogen;

$R^{2\beta}$, $R^{3\beta}$, $R^{4\beta}$, $R^{5\beta}$ and $R^{6\beta}$ are independently selected from the group consisting of hydrogen, lower alkyl, heteroaryl, heterocycle, lower alkoxy, dialkylamino, and halogen;

wherein one of $R^{4\beta}$, $R^{5\beta}$ or $R^{6\beta}$ must be a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\alpha}$, $R^{3\alpha}$, or $R^{4\beta}$ must be carboxy.

In a 14th embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\beta}$ are independently selected from the group consisting of hydrogen, lower alkyl, carboxy, carboxyalkoxy, lower alkoxy, and halogen;

$R^{2\beta}$, $R^{3\beta}$, $R^{4\beta}$, $R^{5\beta}$ and $R^{6\beta}$ are independently selected from the group consisting of hydrogen, lower alkyl, heteroaryl, heterocycle, lower alkoxy, dialkylamino, and halogen;

wherein one of $R^{4\beta}$, $R^{5\beta}$ or $R^{6\beta}$ must be a carbon-carbon linked heterocycle selected from the group consisting of pyrrolidinyl, pyranyl, tetrahydrofuranyl, tetrahydropyranyl, pyranyl, piperidinyl, and piperazinyl;

with the proviso that at least one of $R^{2\alpha}$, $R^{3\alpha}$, or $R^{4\alpha}$ must be carboxy.

In a 15th embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, methyl, carboxy, carboxyalkoxy, methoxy, chloro and fluoro;

$R^{2\beta}$, $R^{3\beta}$, $R^{4\beta}$, $R^{5\beta}$ and $R^{6\beta}$ are independently selected from the group consisting of hydrogen, methyl, furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, isoquinolinyl, methoxy, dimethylamino, chloro and fluoro;

wherein one of $R^{4\beta}$, $R^{5\beta}$ or $R^{6\beta}$ must be a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\alpha}$, $R^{3\alpha}$, $R^{4\alpha}$, $R^{5\alpha}$ or $R^{6\alpha}$ must be carboxy.

In a 16th embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, methyl, carboxy, methoxy, chloro and fluoro;

$R^{2\beta}$, $R^{3\beta}$, $R^{4\beta}$, and $R^{6\beta}$ are independently selected from the group consisting of hydrogen, methyl, methoxy, dimethylamino, chloro and fluoro;

$R^{5\beta}$ is a carbon-carbon linked heteroaryl selected from the group consisting of furanyl, benzofuranyl, oxazolyl, thienyl, benzothienyl, indolyl, pyrrolyl, thiazolyl, imidazolyl, pyrimidinyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\alpha}$, $R^{3\alpha}$, or $R^{4\alpha}$ must be carboxy.

In a 17th embodiment, the invention is represented by Formula I:

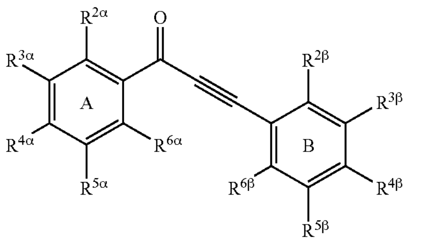

(I)

or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —C(O)R, —$COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —NHC(O)R, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{2\beta}$, $R^{3\beta}$, $R^{4\beta}$, $R^{5\beta}$ or $R^{6\beta}$, or one of $R^{2\alpha}$, $R^{3\alpha}$, $R^{4\alpha}$, $R^{5\alpha}$ or $R^{6\alpha}$ must be a carbon-carbon linked heterocycle or heteroaryl; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $OC(R^1)_2COOH$; and/or at least one of $R^{2\alpha}$, $R^{3\alpha}$, $R^{4\alpha}$, $R^{5\alpha}$, $R^{6\beta}$ or one of $R^{2\beta}$, $R^{3\beta}$, $R^{4\beta}$, $R^{5\beta}$, $R^{6\beta}$ must be selected from the group consisting of carboxy, carboxyalkoxy, cyano, tetrazol-5-yl, —$C(O)OR^2$, —$C(O)NHR^2$, —$C(O)NH_2$, —$C(O)N(R^2)_2$, —$C(CH_3)_2C(O)OH$, —$CH_2C(O)OH$, —$NHR^2$, $NH_2$, —$NHSO_2R^2$, $N(R^2)_2$, —$NR^2SO_2R^2$, —$NHSO_2NHR^2$, —$NHC(O)R^2$, —$NHC(O)OR^2$, —$SCH_2CO_2H$, —$SCF_2CO_2H$, —SH, —$SR^2$, —$NR^2C(O)R^2$, —$NHC(O)SR^2$, $NHC(O)NHR^2$, —$NHC(O)N(R^2)_2$, $SC(R^1)_2COOH$, —$SO_2NH_2$, —$SO_2NHR^2$, —$SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In an 18th broad embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —$C(O)R^2$, —$COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, —NHC(O) $NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{2\beta}$, $R^{3\beta}$, $R^{4\beta}$, $R^{5\beta}$ or $R^{6\beta}$, or one of $R^{2\alpha}$, $R^{3\alpha}$, $R^{4\alpha}$, $R^{5\alpha}$ or $R^{6\alpha}$ must be a carbon-carbon linked heterocycle or heteroaryl and only one of $R^{2\beta}$, $R^{3\beta}$, $R^{4\beta}$, $R^{5\beta}$ or $R^{6\beta}$; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $—OC(R^1)_2COOH$; and/or at least one of $R^{2\alpha}$, $R^{3\alpha}$ $R^{4\alpha}$ or one of $R^{2\beta}$, $R^{3\beta}$ $R^{4\beta}$ must be selected from the group consisting of carboxy, carboxyalkoxy, cyano, tetrazol-5-yl, $—C(O)OR^2$, $—C(O)NHR^2$, $—C(O)NH_2$, $—C(O)N(R^2)_2$, $—C(CH_3)_2C(O)OH$, $—CH_2C(O)OH$, $—NHR_1$, $NH_2$, $—NHSO_2R^2$, $N(R^2)_2$, $—NR^2SO_2R^2$, $—NHSO_2NHR^2$, $—NHC(O)R^2$, —NHC(O)OR, $—SCH_2CO_2H$, $—SCF_2CO_2H$, —SH, $—SR^2$, $—NR^2C(O)R^2$, $—NHC(O)SR^2$, $NHC(O)NHR^2$, $—NHC(O)N(R^2)_2$, $SC(R^1)_2COOH$, $—SO_2NH_2$, $—SO_2NHR^2$, $—SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 19th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower, alkyl, S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, —NHC(O) $NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{2\beta}$, $R^{3\beta}$, $R^{4\beta}$, $R^{5\beta}$ or $R^{6\beta}$ must be a carbon-carbon linked heterocycle or heteroaryl; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $—OC(R^1)_2COOH$; and/or at least one of $R^{2\alpha}$, $R^{3\alpha}$, $R^{4\alpha}$, $R^{5\alpha}$, or $R^{6\alpha}$ must be selected from the group consisting of carboxy, carboxyalkoxy, cyano, tetrazol-5-yl, $—C(O)OR^2$, $—C(O)NHR^2$, $—C(O)NH_2$, $—C(O)N(R^2)_2$, $—C(CH_3)_2C(O)OH$, $—CH_2C(O)OH$, $—NHR^2$, $NH_2$, $—NHSO_2R^2$, $N(R^2)_2$, $—NR^2SO_2R^2$, $—NHSO_2NHR^2$, $—NHC(O)R^2$, $—NHC(O)OR^2$, $—SCH_2CO_2H$, $—SCF_2CO_2H$, —SH, $—SR^2$, $—NR^2C(O)R^2$, $—NHC(O)SR^2$, $NHC(O)NHR^2$, $—NHC(O)N(R^2)_2$, $SC(R^1)_2COOH$, $—SO_2NH_2$, $—SO_2NHR^2$, $—SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 20th broad embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $—OC(R^1)_2COOH$; and/or at least one of $R^{2\alpha}$, $R^{3\alpha}$, or $R^{4\alpha}$ must be selected from the group consisting of carboxy, carboxyalkoxy, cyano, tetrazol-5-yl, $—C(O)OR^2$, $—C(O)NHR^2$, $—C(O)NH_2$, $—C(O)N(R^2)_2$, $—C(CH_3)_2C(O)OH$, $—CH_2C(O)OH$, $—NHR^2$, $NH_2$, $—NHSO_2R^2$, $N(R^2)_2$, $—NR^2SO_2R^2$, $—NHSO_2NHR^2$, $—NHC(O)R^2$, $—NHC(O)OR^2$, $—SCH_2CO_2H$, $—SCF_2CO_2H$, —SH, $—SR^2$, $—NR^2C(O)R^2$, $—NHC(O)SR^2$, $NHC(O)NHR^2$, $—NHC(O)N(R^2)_2$, $SC(R^2)_2COOH$, $—SO_2NH_2$, $—SO_2NHR^2$, $—SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 21st embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\beta}$, or $R^{4\alpha}$ must be selected from the group consisting of carboxy, carboxyalkoxy, cyano, tetrazol-5-yl, —$C(O)OR^2$, —$C(O)NHR^2$, —$C(O)NH_2$, —$C(O)N(R^2)_2$, —$C(CH_3)_2C(O)OH$, —$CH_2C(O)OH$, —$NHR^2$, $NH_2$, —$NHSO_2R^2$, $N(R^2)_2$, —$NR^2SO_2R^2$, —$NHSO_2NHR^2$, —$NHC(O)R^2$, —$NHC(O)OR^2$, $SC(R^1)_2COOH$, —$SCH_2CO_2H$, —$SCF_2CO_2H$, —SH, —$SR^2$, —$NR^2C(O)R^2$, —$NHC(O)SR^2$, $NHC(O)NHR^2$, —$NHC(O)N(R^2)_2$, —$SO_2NH_2$, —$SO_2NHR^2$, —$SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 22nd embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, aryloxy, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —$C(O)R^2$, —$COOR^2$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of carboxy, carboxyalkoxy, cyano, tetrazol-5-yl, —$C(O)OR^1$, —$C(O)NHR^2$, —$C(O)NH_2$, —$C(O)N(R^2)_2$, —$C(CH_3)_2C(O)OH$, —$CH_2C(O)OH$, —$SCH_2CO_2H$, $SC(R^1)_2COOH$, and —$SCF_2CO_2H$.

In a 23rd embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy carbocycle, aryl, heteroaryl, heterocycle, cycloalkyl, cyano, alkoxy, lower alkoxy, aryloxy, arylalkoxy, heteroaryloxy, heteroarylalkoxy, alkylthio, alkylamino, aminoalkyl, haloalkylthio, acyl, haloalkyl, aryloxy, acylamino, amino, dialkylamino, haloalkoxy, alkylsulfonyl, haloalkylsulfonyl, halogen, thiol, nitro, alditol, carbohydrate, —$OC(R^1)_2COOH$, —$SC(R^1)_2COOH$, —$NHC(R^1)_2COOH$, —$C(O)R^2$, —$COOR^2$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of carboxy, carboxyalkoxy, cyano, tetrazol-5-yl, —C(O)$OR^2$, —C(O)$NHR^2$, —C(O)$NH_2$, —C(O)$N(R^2)_2$, —$C(CH_3)_2C$(O)OH, —$CH_2C$(O)OH, $SC(R^1)_2COOH$, and —$SCH_2CO_2H$.

In a 24th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy heteroaryl, heterocycle, cycloalkyl, cyano, alkoxy, lower alkoxy, aryloxy, arylalkoxy, heteroaryloxy, heteroarylalkoxy, alkylthio, alkylamino, aminoalkyl, haloalkylthio, acylamino, acyl, haloalkyl, aryloxy, acylamino, amino, dialkylamino, haloalkoxy, halogen, alditol, carbohydrate, —$COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heterocyclo lower alkoxy, heterocycleoxy, heterocyclo lower alkyl, heterocyclothio lower alkyl, heteroarylamino lower alkyl, heterocycloamino lower alkyl, arylamino, heterocycleamino, heteroarylamino, cycloalkylamino, heterocyclealkoxy, cycloalkyloxy, —C(O)$NH_2$, —C(O)$NHR^2$, —C(O)$N(R^2)_2$, —NHC(O)$R^2$, —$N(R^2)$C(O)$R^2$, —NHC(O)$OR^2$; —NHC(O)$SR^2$, —$NHSO_2NHR^2$, —$NHSO_2R^2$, —N(C(O)$NHR^2)_2$, —$NR^2SO_2R^2$, —NHC(O)$NHR^2$, and —NHC(O)$N(R^2)_2$, all of which can be optionally substituted by one or more selected from the group consisting of hydroxy, alkyl, lower alkyl, hydroxyalkyl, aminoalkyl, amino, alkoxy, acyl, alkoxycarbonyl, oxo, and halo;

$R^1$ is selected from the group consisting of hydrogen, lower alkyl, and cycloalkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is selected from the group consisting of alkyl, lower alkyl, aryl, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of carboxy, carboxyalkoxy, tetrazol-5-yl, —C(O)$NHR^2$, —C(O)$NH_2$, —$SCH_2CO_2H$ and —C(O)$N(R^2)_2$.

In a 25th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, hydroxyl, carboxy, heteroaryl, heterocycle, cycloalkyl, alkoxy, lower alkoxy, alkylthio, alkylamino, aminoalkyl, acylamino, amino, dialkylamino, halogen, polyol alkyl, hydroxyalkyl, heterocyclo lower alkoxy, heterocycleoxy, heterocyclo lower alkyl, arylamino, heterocycleamino, heteroarylamino, cycloalkylamino, heterocyclealkoxy, cycloalkyloxy, —NHC(O)$R^2$, —$N(R^2)$C(O)$R^2$, —NHC(O)$OR^2$, —NHC(O)$SR^2$, —$NHSO_2NHR^2$, —$NHSO_2R^2$, —N(C(O)$NHR^2)_2$, —$NR^2SO_2R^2$, —NHC(O)$NHR^2$, and —NHC(O)$N(R^2)_2$, all of which can be optionally substituted by one or more selected from the group consisting of hydroxy, lower alkyl, hydroxyalkyl, aminoalkyl, amino, acyl; alkoxycarbonyl, and halo;

$R^2$ is selected from the group consisting of alkyl, lower alkyl, aryl, heteroaryl, and heterocycle, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\beta}$, $R^{3\alpha}$, or $R^{4\alpha}$ must be selected from the group consisting of carboxy, carboxyalkoxy, tetrazol-5-yl, —C(O)$NHR^2$, and —C(O)$NH_2$.

In a 26th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, lower alkyl, carboxy, heteroaryl, heterocycle, alkoxy, lower alkoxy, alkylamino, amino, dialkylamino, halogen, and —$NHSO_2R^2$, all of which can be optionally substituted by one or more selected from the group consisting of hydroxy, lower alkyl, hydroxyalkyl, aminoalkyl, amino, and halo;

$R^2$ is selected from the group consisting of lower alkyl, and aryl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of carboxy, carboxymethoxy, and tetrazol-5-yl.

In a 27th embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, lower alkyl, carboxy, heteroaryl, heterocycle, lower alkoxy, dialkylamino, and halogen, all of which can be optionally substituted by one or more selected from the group consisting of hydroxy, lower alkyl, hydroxyalkyl, aminoalkyl, amino, acyl, alkoxycarbonyl, and halo;

$R^{2\beta}$, $R^{3\beta}$, $R^{4\beta}$, $R^{5\beta}$ and $R^{6\beta}$ are independently selected from the group consisting of hydrogen, lower alkyl, carboxy, heteroaryl, heterocycle, lower alkoxy, dialkylamino, and halogen, all of which can be optionally substituted by one or more selected from the group consisting of hydroxy, lower alkyl, hydroxyalkyl, aminoalkyl, amino, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be carboxy or carboxymethoxy.

In a 28th embodiment, the invention is represented by Formula I or its pharmaceutically acceptable salt or ester, wherein:

$R^{2\alpha}$, $R^{3\beta}$, $R^{4\beta}$, $R^{5\beta}$, and $R^{6\beta}$ are independently selected from the group consisting of hydrogen, lower alkyl, carboxy, lower alkoxy, and halogen;

$R^{2\beta}$, $R^{3\beta}$, $R^{4\beta}$, $R^{5\beta}$ and $R^{6\beta}$ are independently selected from the group consisting of hydrogen, lower alkyl, heteroaryl, heterocycle, lower alkoxy, dialkylamino, and halogen all of which can be optionally substituted by one or more selected from the group consisting of hydroxy, methyl, hydroxymethyl, aminomethyl, amino, acyl, alkoxycarbonyl, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be carboxy or carboxymethoxy.

In a 29th embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, lower alkyl, carboxy, lower alkoxy, and halogen;

$R^{2\beta}$, $R^{3\beta}$, $R^{4\beta}$, $R^{5\beta}$ and $R^{6\beta}$ are independently selected from the group consisting of hydrogen, lower alkyl, heteroaryl, heterocycle, lower alkoxy, dialkylamino, and halogen;

wherein one of $R^{4\beta}$, $R^{5\beta}$ or $R^{6\beta}$ must be a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\alpha}$, $R^{3\alpha}$, or $R^{4\alpha}$ must be carboxy or carboxymethoxy.

In a 30th embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, lower alkyl, carboxy, lower alkoxy, and halogen;

$R^{2\beta}$, $R^{3\beta}$, $R^{4\beta}$, $R^{5\beta}$ and $R^{6\beta}$ are independently selected from the group consisting of hydrogen, lower alkyl, heteroaryl, heterocycle, lower alkoxy, dialkylamino, and halogen;

wherein one of $R^{4\beta}$, $R^{5\beta}$ or $R^{6\beta}$ must be a carbon-carbon linked heterocycle selected from the group consisting of pyrrolidinyl, pyranyl, tetrahydrofuranyl, tetrahydropyranyl, pyranyl, piperidinyl, and piperazinyl;

with the proviso that at least one of $R^{2\alpha}$, $R^{3\alpha}$, or $R^{4\alpha}$ must be carboxy or carboxymethoxy.

In a 31st embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, methyl, carboxy, methoxy, chloro and fluoro;

$R^{2\beta}$, $R^{3\beta}$, $R^{4\beta}$, $R^{5\beta}$ and $R^{6\beta}$ are independently selected from the group consisting of hydrogen, methyl, furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, isoquinolinyl, methoxy, dimethylamino, chloro and fluoro;

wherein one of $R^{4\beta}$, $R^{5\beta}$ or $R^{6\beta}$ must be a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\alpha}$, $R^{3\alpha}$, $R^{4\alpha}$, $R^{5\alpha}$ or $R^{6\alpha}$ must be carboxy or carboxymethoxy.

In a 32nd embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, methyl, carboxy, methoxy, chloro and fluoro;

$R^{2\beta}$, $R^{3\beta}$, $R^{4\beta}$, and $R^{6\beta}$ are independently selected from the group consisting of hydrogen, methyl, methoxy, dimethylamino, chloro and fluoro;

$R^{5\beta}$ is a carbon-carbon linked heteroaryl selected from the group consisting of furanyl, benzofuranyl, oxazolyl, thienyl, benzothienyl, indolyl, pyrrolyl, thiazolyl, imidazolyl, pyrimidinyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\alpha}$, $R^{3\alpha}$, or $R^{4\alpha}$ must be carboxy or carboxymethoxy.

In a 33rd embodiment, the invention is represented by Formula I or its pharmaceutically acceptable salt or ester, wherein:

$R^{2\alpha}$, $R^{3\alpha}$, $R^{5\alpha}$, $R^{6\alpha}$ $R^{3\beta}$, and $R^{6\beta}$ are hydrogen;

$R^{4\alpha}$ is carboxy or carboxymethoxy;

$R^{2\beta}$ and $R^{4\beta}$ are methoxy; and $R^{5\beta}$ is a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl.

In a 34th embodiment, the invention is represented by Formula I or its pharmaceutically acceptable salt or ester, wherein:

$R^{2\alpha}$, $R^{3\alpha}$, $R^{5\alpha}$, $R^{6\alpha}$ $R^{3\beta}$, and $R^{6\beta}$ are hydrogen;

$R^{4\alpha}$ is carboxy;

$R^{2\beta}$ and $R^{4\beta}$ are methoxy; and $R^{5\beta}$ is 5-(benzothien-2-yl).

In a 35th embodiment, the invention is represented by Formula I or its pharmaceutically acceptable salt or ester, wherein:

$R^{2\alpha}$, $R^{3\alpha}$, $R^{5\alpha}$, $R^{6\alpha}$ $R^{3\beta}$, and $R^{6\beta}$ are hydrogen;

$R^{4\alpha}$ is carboxy;

$R^{2\beta}$ and $R^{4\beta}$ are methoxy; and $R^{5\beta}$ is thienyl.

In a 36th embodiment, the invention is represented by Formula I or its pharmaceutically acceptable salt or ester, wherein:

$R^{2\alpha}$, $R^{3\alpha}$, $R^{5\alpha}$, $R^{6\alpha}$ $R^{3\beta}$, and $R^{6\beta}$ are hydrogen;

$R^{4\alpha}$ is carboxy;

$R^{2\beta}$ and $R^{4\beta}$ are methoxy; and $R^{5\beta}$ is indolyl.

In a 37th embodiment, the invention is represented by Formula I or its pharmaceutically acceptable salt or ester, wherein:

$R^{2\alpha}$, $R^{6\alpha}$, $R^{3\beta}$ and $R^{6\beta}$ are hydrogen;

$R^{4\alpha}$ is carboxymethoxy;

$R^{3\alpha}$, $R^{5\alpha}$, $R^{2\beta}$ and $R^{4\beta}$ are methoxy; and $R^{5\beta}$ is 5-(benzothien-2-yl).

In a 38th embodiment, the invention is represented by Formula I or its pharmaceutically acceptable salt or ester, wherein:

$R^{2\alpha}$, $R^{6\alpha}$, $R^{3\beta}$ and $R^{6\beta}$ are hydrogen;

$R^{4\alpha}$ is carboxymethoxy;

$R^{3\alpha}$, $R^{5\alpha}$, $R^{2\beta}$ and $R^{4\beta}$ are methoxy; and $R^{5\beta}$ is thienyl.

In a 39th embodiment, the invention is represented by Formula I or its pharmaceutically acceptable salt or ester, wherein:

$R^{2\alpha}$, $R^{6\alpha}$, $R^{3\beta}$ and $R^{6\beta}$ are hydrogen;

$R^{4\alpha}$ is carboxymethoxy;

$R^{3\alpha}$, $R^{5\alpha}$, $R^{2\beta}$ and $R^{4\beta}$ are methoxy; and $R^{5\beta}$ is indolyl.

In a 40th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, alkoxycarbonyl, acyl, oxo, acyl, alkoxycarbonyl and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of $—NHR^2$, $—NH_2$, $—NHSO_2R^2$, $—N(R^2)_2$, $—NR^2C(O)R^2$, $—NHC(O)SR^2$, $—NHC(O)NHR^2$, $—NHC(O)N(R^2)_2$, $—NR^2SO_2R^2$, $—NHSO_2NHR^2$, $—NHC(O)R^2$, and $NHC(O)OR^2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 41st embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, carbocycle, heteroaryl, heterocycle, cycloalkyl, tetrazol-5-yl, alkoxy, lower alkoxy, aryloxy, arylalkoxy, heteroaryloxy, heteroarylalkoxy, alkylthio, alkylamino, haloalkyl, acylamino, dialkylamino, haloalkoxy, halogen, alditol, carbohydrate, $—OC(R^1)_2COOH$, $—SC(R^1)_2COOH$, $—NHC(R^1)_2COOH$, $—COOR^1$, polyoxyalkylene, polyol alkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—P(R^2)O_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, lower alkyl, hydroxyalkyl, alkoxy, acyl, alkoxycarbonyl and halo;

$R^1$ is independently selected from the group consisting of hydrogen and lower alkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of lower alkyl, heterocycle, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of $—NHR^2$, $—NH_2$, $—NHSO_2R^2$, $—N(R^2)_2$, and $—NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, hydroxyalkyl, alkoxy, and halo.

In a 42nd embodiment, the invention is represented by Formula I or its pharmaceutically acceptable salt or ester, wherein:

$R^{2\alpha}$, $R^{3\alpha}$, $R^{4\beta}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, lower alkyl, heterocycle, cycloalkyl, alkoxy, lower alkoxy, dialkylamino, halogen, hydroxyalkyl, heteroaryl lower alkoxy, heterocyclo lower alkoxy, heterocycleoxy, heterocyclo lower alkyl, cycloalkyloxy, —$NHC(O)R^2$, —$NHSO_2R^2$, all of which can be optionally substituted by one or more selected from the group consisting of hydroxy, lower alkyl, hydroxyalkyl, alkoxy, acyl, alkoxycarbonyl and halo;

$R^2$ is independently selected from the group consisting of lower alkyl, heterocycle, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of —$NHR^2$, —$NH_2$, —$NHSO_2R^2$, —$N(R^2)_2$, and —$NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, hydroxyalkyl, alkoxy, and halo.

In a 43rd embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, lower alkyl, lower alkoxy, and halogen, all of which can be optionally substituted by one or more selected from the group consisting of hydroxy, lower alkyl, hydroxyalkyl, alkoxy, acyl, alkoxycarbonyl and halo;

$R^2$ is independently selected from the group consisting of lower alkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of —$NHR^2$, —$NH_2$, —$NHSO_2R^2$, —$N(R^2)_2$, and —$NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, hydroxyalkyl, alkoxy, and halo.

In a 44th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —$C(O)R^2$, —$COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, $NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, oxo, acetyl, carboalkoxy and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\beta}$, $R^{5\beta}$ or $R^{6\beta}$ must be a carbon-carbon linked heterocycle or heteroaryl;

wherein at least one of $R^{2\beta}$, $R^{3\beta}$, or $R^{4\alpha}$ must be selected from the group consisting of —$SCH_2CO_2H$, —$SCF_2CO_2H$, —SH, —$SCH_3$, —$SO_2NH_2$, —$SO_2NHR^2$, and —$SO_2N(R^2)_2$.

In a 45th embodiment, the invention is represented by Formula I or its pharmaceutically salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, haloalkyl, acylamino, amino, dialkylamino, haloalkoxy, alkylsulfonyl, haloalkylsulfonyl, halogen, thiol, alditol, carbohydrate, —$OC(R^1)_2COOH$, —$SC(R^1)_2COOH$, —$NHC(R^1)_2COOH$, —$COOR^1$, hydroxyalkyl, heteroaryl lower alkoxy, heterocyclo lower alkoxy, heterocycleoxy, heteroarylamino lower alkyl, heterocycloamino lower alkyl, arylamino, heterocycleamino, heteroarylamino, cycloalkylamino, cycloalkylalkyl, heterocyclealkoxy, cycloalkylalkoxy, cycloalkyloxy, cycloalkylaminoalkyl, —$C(O)NH_2$, —$C(O)NHR^2$, —$C(O)N(R^2)_2$, —NHC(O)R, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\beta}$, $R^{5\beta}$ or $R^{6\beta}$ must be a carbon-carbon linked heterocycle or heteroaryl;

wherein at least one of $R^{2\alpha}$, $R^{3\alpha}$, or $R^{4\alpha}$ must be selected from the group consisting of —$SCH_2CO_2H$, —$SCF_2CO_2H$, —SH, —$SCH_3$, —$SO_2NH_2$, —$SO_2NHR^2$, —$SO_2N(R^2)_2$, and $SC(R^1)_2COOH$.

In a 46th embodiment, the invention is represented by Formula I or its pharmaceutically salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, alkoxy, lower alkoxy, alkylthio, alkylamino, haloalkylthio, acylamino, amino, dialkylamino, alkylsulfonyl, haloalkylsulfonyl, halogen, thiol, —$SC(R^1)_2COOH$, hydroxyalkyl, cycloalkyloxy, cycloalkylaminoalkyl, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, oxo, acetyl, carboalkoxy and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\beta}$, $R^{5\beta}$ or $R^{6\beta}$ must be a carbon-carbon linked heterocycle or heteroaryl;

wherein at least one of $R^{2\alpha}$, $R^{3\alpha}$, or $R^{4\alpha}$ must be selected from the group consisting of —$SCH_2CO_2H$, —$SCF_2CO_2H$, —SH, —$SCH_3$, —$SO_2NH_2$, —$SO_2NHR^2$, —$SO_2N(R^2)_2$, and $SC(R^1)_2COOH$.

In a 47th embodiment, the invention is represented by Formula I or its pharmaceutically salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, lower alkyl, heteroaryl, heterocycle, lower alkoxy, alkylthio, acylamino, dialkylamino, alkylsulfonyl, haloalkylsulfonyl, halogen, thiol, —$SC(R^1)_2COOH$, hydroxyalkyl, —$SO_2NH_2$, —$SO_2NHR_2$, —$SO_2N(R^2)_2$, —$SCF_2CO_2H$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, oxo, acetyl, carboalkoxy and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\beta}$, $R^{5\beta}$ or $R^{6\beta}$ must be a carbon-carbon linked heterocycle or heteroaryl;

wherein at least one of $R^{2\alpha}$, $R^{3\alpha}$, or $R^{4\alpha}$ must be selected from the group consisting of —$SCH_2CO_2H$, —$SCF_2CO_2H$, —SH, —$SCH_3$, —$SO_2NH_2$, —$SO_2NHR^2$, —$SO_2N(R^2)_2$, and $SC(R^1)_2COOH$.

In a 48th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —$C(O)R^2$, —$COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acetyl, carbalkoxy, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\beta}$, $R^{5\beta}$ or $R^{6\beta}$ must be a carbon-carbon linked heterocycle or heteroaryl;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $—OC(R^1)_2COOH$.

In a 49th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acetyl, carboalkoxy, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\beta}$, $R^{5\beta}$ or $R^{6\beta}$ must be a carbon-carbon linked heterocycle or heteroaryl;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, oxo, and halo.

In a 50th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acetyl, carboalkoxy, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\beta}$, $R^{5\beta}$ or $R^{6\beta}$ must be a carbon-carbon linked heterocycle or heteroaryl;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- to 6-membered heterocycle or heteroaryl containing one or more oxygen hetero atom, said heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, oxo, and halo.

In a 51st broad embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —$C(O)R^2$, —$COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —NHC(O)OR, —$NHC(O)SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{2\beta}$, $R^{3\beta}$, $R^{4\beta}$, $R^{5\beta}$ or $R^{6\beta}$, or one of $R^{2\alpha}$, $R^{3\alpha}$, $R^{4\alpha}$, $R^{5\alpha}$ or $R^{6\alpha}$ must be a carbon-carbon linked heterocycle or heteroaryl;

with the proviso that $R^{2\alpha}$ and $R^{3\alpha}$ taken together or $R^{3\beta}$ and $R^{4\beta}$ taken together or $R^{4\beta}$ and $R^{5\beta}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —$OC(R^1)_2COOH$; or at least one of $R^{2\alpha}$, $R^{3\alpha}$ $R^{4\alpha}$ or one of $R^{2\beta}$, $R^{3\beta}$ $R^{4\beta}$ must be selected from the group consisting of carboxy, carboxyalkoxy, cyano, tetrazol-5-yl, —$C(O)OR^2$, —$C(O)NHR^2$, —$C(O)NH_2$, —$C(O)N(R^2)_2$, —$C(CH_3)_2C(O)OH$, —$CH_2C(O)OH$, —$NHR_1$, $NH_2$, —$NHSO_2R^2$, $N(R^2)_2$, —$NR^2SO_2R^2$, —$NHSO_2NHR^2$, —$NHC(O)R^2$, —$NHC(O)OR^2$, —$SCH_2CO_2H$, —$SCF_2CO_2H$, —SH, —$SR^2$, —$NR^2C(O)R^2$, —$NHC(O)SR^2$, $NHC(O)NHR^2$, —$NHC(O)N(R^2)_2$, $SC(R^1)_2COOH$, —$SO_2NH_2$, —$SO_2NHR^2$, —$SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 52nd broad embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —$C(O)R^2$, —$COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{2\alpha}$, $R^{3\alpha}$, $R^{4\alpha}$, $R^{5\alpha}$ or $R^{6\alpha}$ must be a carbon-carbon linked heterocycle or heteroaryl;

with the proviso that $R^{2\beta}$ and $R^{3\beta}$ taken together or $R^{3\beta}$ and $R^{4\beta}$ taken together or $R^{4\beta}$ and $R^{5\beta}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $OC(R^1)_2COOH$; or at least one of $R^{2\beta}$, $R^{3\beta}$, $R^{4\beta}$, $R^{5\beta}$ or $R^{6\beta}$ must be selected from the group consisting of carboxy, carboxyalkoxy, cyano, tetrazol-5-yl, $—C(O)OR^2$, $—C(O)NHR^2$, $—C(O)NH_2$, $—C(O)N(R^2)_2$, $—C(CH_3)_2C(O)OH$, $—CH_2C(O)OH$, $—NHR^2$, $NH_2$, $—NHSO_2R^2$, $N(R^2)_2$, $—NR\ SO_2R^2$, $—NHSO_2NHR^2$, $—NHC(O)R^2$, $—NHC(O)OR^2$, $—SCH_2CO_2H$, $—SCF_2CO_2H$, —SH, $—SR^2$, $—NR^2C(O)R^2$, $—NHC(O)SR^2$, $NHC(O)NHR^2$, $—NHC(O)N(R^2)_2$, $SC(R^1)_2COOH$, $—SO_2NH_2$, $—SO_2NHR^2$, $—SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a $53^{rd}$ broad embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that $R^{2\beta}$ and $R^{3\beta}$ taken together or $R^{3\beta}$ and $R^{4\beta}$ taken together or $R^{4\beta}$ and $R^{5\beta}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $—OC(R^1)_2COOH$; or at least one of $R^{2\beta}$, $R^{3\beta}$, or $R^{4\beta}$ must be selected from the group consisting of carboxy, carboxyalkoxy, cyano, tetrazol-5-yl, $—C(O)OR^2$, $—C(O)NHR^2$, $—C(O)NH_2$, $—C(O)N(R^2)_2$, $—C(CH_3)_2C(O)OH$, $—CH_2C(O)OH$, $—NHR^2$, $NH_2$, $—NHSO_2R^2$, $N(R^2)_2$, $—NR^2SO_2R^2$, $—NHSO_2NHR^2$, $—NHC(O)R^2$, $—NHC(O)OR^2$, $—SCH_2CO_2H$, $—SCF_2CO_2H$, —SH, $—SR^2$, $—NR^2C(O)R^2$, $—NHC(O)SR^2$, $NHC(O)NHR^2$, $—NHC(O)N(R^2)_2$, $SC(R^1)_2COOH$, $—SO_2NH_2$, $—SO_2NHR^2$, $—SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 54th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —OC$(R^1)_2$COOH, —SC$(R^1)_2$COOH, —NHC$(R^1)_2$COOH, —C(O)$R^2$, —COO$R^1$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —C(O)$NH_2$, —C(O)NH$R^2$, —C(O)N$(R^2)_2$, —NHC(O)$R^2$, —N$(R^2)$C(O)$R^2$, —NHC(O)O$R^2$, —NHC(O)S$R^2$, —NH$SO_2$NH$R^2$, —$SO_2NH_2$, —$SO_2NHR_2$, —$SO_2N(R^2)_2$, —$PO_2H_2$, —$PO_3H_2$, P$(R^2)O_2$H, —$SCF_2CO_2H$, —NH$SO_2R^2$, —N(C(O)NH$R^2$)$_2$, —N$R^2SO_2R^2$, —NHC(O)NH$R^2$, and —NHC(O)N$(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be selected from the group consisting of carboxy, carboxyalkoxy, cyano, tetrazol-5-yl, —C(O)O$R^2$, —C(O)NH$R^2$, —C(O)$NH_2$, —C(O)N$(R^2)_2$, —C$(CH_3)_2$C(O)OH, —$CH_2$C(O)OH, —NH$R^2$, $NH_2$, —NH$SO_2R^2$, N$(R^2)_2$, —NR $SO_2R^2$, —NH$SO_2$NH$R^2$, —NHC(O)$R^2$, —NHC(O)O$R^2$, SC$(R^1)_2$COOH, —$SCH_2CO_2H$, —$SCF_2CO_2H$, —SH, —$SR^2$—N$R^2$C(O)$R^2$, —NHC(O)S$R^2$, NHC(O)NH$R^2$, —NHC(O)N$(R^2)_2$, —$SO_2NH_2$, —$SO_2$NH$R^2$, —$SO_2N(R^2)_2$, and N$R^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 55th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, aryloxy, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —OC$(R^1)_2$COOH, —SC$(R^1)_2$COOH, —NHC$(R^1)_2$COOH, —C(O)$R^2$, —COO$R^2$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —C(O)$NH_2$, —C(O)NH$R^2$, —C(O)N$(R^2)_2$, —NHC(O)$R^2$, —N$(R^2)$C(O)$R^2$, —NHC(O)O$R^2$, —NHC(O)S$R^2$, —NH$SO_2$NH$R^2$, —$SO_2NH_2$, —$SO_2NHR_2$, —$SO_2N(R^2)_2$, —$PO_2H_2$, —$PO_3H_2$, P$(R^2)O_2$H, —$SCF_2CO_2H$, —NH$SO_2R^2$, —N(C(O)NH$R^2$)$_2$, —N$R^2SO_2R^2$, —NHC(O)NH$R^2$, and —NHC(O)N$(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be selected from the group consisting of carboxy, carboxyalkoxy, cyano, tetrazol-5-yl, —C(O)O$R^1$, —C(O)NH$R^2$, —C(O)$NH_2$, —C(O)N$(R^2)_2$, —C$(CH_3)_2$C(O)OH, —$CH_2$C(O)OH, —$SCH_2CO_2H$, SC$(R^1)_2$COOH, and —$SCF_2CO_2H$.

In a 56th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy carbocycle, aryl, heteroaryl, heterocycle, cycloalkyl, cyano, alkoxy, lower alkoxy, aryloxy, arylalkoxy, heteroaryloxy, heteroarylalkoxy, alkylthio, alkylamino, aminoalkyl, haloalkylthio, acyl, haloalkyl, aryloxy, acylamino, amino, dialkylamino, haloalkoxy, alkylsulfonyl, haloalkylsulfonyl, halogen, thiol, nitro, alditol, carbohydrate, —OC$(R^1)_2$COOH, —SC$(R^1)_2$COOH, —NHC$(R^1)_2$COOH, —C(O)$R^2$, —COO$R^2$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —C(O)$NH_2$, —C(O)$NHR^2$, —C(O)$N(R^2)_2$, —NHC(O)$R^2$, —$N(R^2)$C(O)$R^2$, —NHC(O)OR, —NHC(O)$SR^2$, —$NHSO_2NHR^2$, —$SO_2NH_2$, —$SO_2NHR_2$, —$SO_2N(R^2)_2$, —$NHSO_2R^2$, —N(C(O)$NHR^2)_2$, —$NR^2SO_2R^2$, —NHC(O)$NHR^2$, and —NHC(O)$N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be selected from the group consisting of carboxy, carboxyalkoxy, cyano, tetrazol-5-yl, —C(O)$OR^2$, —C(O)$NHR^2$, —C(O)$NH_2$, —C(O)$N(R^2)_2$, —$C(CH_3)_2$C(O)OH, —$CH_2$C(O)OH, $SC(R^1)_2COOH$, and —$SCH_2CO_2H$.

In a 57th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy heteroaryl, heterocycle, cycloalkyl, cyano, alkoxy, lower alkoxy, aryloxy, arylalkoxy, heteroaryloxy, heteroarylalkoxy, alkylthio, alkylamino, aminoalkyl, haloalkylthio, acylamino, acyl, haloalkyl, aryloxy, acylamino, amino, dialkylamino, haloalkoxy, halogen, alditol, carbohydrate, —$COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heterocyclo lower alkoxy, heterocycleoxy, heterocyclo lower alkyl, heterocyclothio lower alkyl, heteroarylamino lower alkyl, heterocycloamino lower alkyl, arylamino, heterocycleamino, heteroarylamino, cycloalkylamino, heterocyclealkoxy, cycloalkyloxy, —C(O)$NH_2$, —C(O)$NHR^2$, —C(O)$N(R^2)_2$, —NHC(O)$R^2$, —$N(R^2)$C(O)$R^2$, —NHC(O)$OR^2$, —NHC(O)SR, —$NHSO_2NHR^2$, —$NHSO_2R^2$, —N(C(O)$NHR^2)_2$, —$NR^2SO_2R^2$, —NHC(O)$NHR^2$, and —NHC(O)$N(R^2)_2$, all of which can be optionally substituted by one or more selected from the group consisting of hydroxy, alkyl, lower alkyl, hydroxyalkyl, aminoalkyl, amino, alkoxy, acyl, alkoxycarbonyl, oxo, and halo;

$R^1$ is selected from the group consisting of hydrogen, lower alkyl, and cycloalkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is selected from the group consisting of alkyl, lower alkyl, aryl, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be selected from the group consisting of carboxy, carboxyalkoxy, tetrazol-5-yl, —C(O)$NHR^2$, —C(O)$NH_2$, —$SCH_2CO_2H$ and —C(O)$N(R^2)_2$.

In a 58th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, hydroxyl, carboxy, heteroaryl, heterocycle, cycloalkyl, alkoxy, lower alkoxy, alkylthio, alkylamino, aminoalkyl, acylamino, amino, dialkylamino, halogen, polyol alkyl, hydroxyalkyl, heterocyclo lower alkoxy, heterocycleoxy, heterocyclo lower alkyl, arylamino, heterocycleamino, heteroarylamino, cycloalkylamino, heterocyclealkoxy, cycloalkyloxy, —NHC(O)R, —$N(R^2)$C(O)R, —NHC(O)$OR^2$, —NHC(O)SR, —$NHSO_2NHR^2$, —$NHSO_2R^2$, —N(C(O)$NHR^2)_2$, —$NR^2SO_2R^2$, —NHC(O)$NHR^2$, and —NHC(O)$N(R^2)_2$, all of which can be optionally substituted by one or more selected from the group consisting of hydroxy, lower alkyl, hydroxyalkyl, aminoalkyl, amino, acyl, alkoxycarbonyl, and halo;

$R^2$ is selected from the group consisting of alkyl, lower alkyl, aryl, heteroaryl, and heterocycle, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be selected from the group consisting of carboxy, carboxyalkoxy, tetrazol-5-yl, —C(O)$NHR^2$, and —C(O)$NH_2$.

In a 59th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, lower alkyl, carboxy, heteroaryl, heterocycle, alkoxy, lower alkoxy, alkylamino, amino, dialkylamino, halogen, and —$NHSO_2R^2$, all of which can be optionally substituted by one or more selected from the group consisting of hydroxy, lower alkyl, hydroxyalkyl, aminoalkyl, amino, and halo;

$R^2$ is selected from the group consisting of lower alkyl, and aryl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be selected from the group consisting of carboxy, carboxy-alkoxy, and tetrazol-5-yl.

In a 60th embodiment, the invention is represented by Formula I or its pharmaceutically acceptable salt or ester, wherein:

$R^{2\beta}$, $R^{3\beta}$, $R^{4\beta}$, $R^{5\beta}$ and $R^{6\beta}$ are independently selected from the group consisting of hydrogen, lower alkyl, carboxy, heteroaryl, heterocycle, lower alkoxy, dialkylamino, and halogen, all of which can be optionally substituted by one or more selected from the group consisting of hydroxy, lower alkyl, hydroxyalkyl, aminoalkyl, amino, acyl, alkoxycarbonyl, and halo;

$R^{2\alpha}$, $R^{3\alpha}$, $R^{4\alpha}$, $R^{5\alpha}$ and $R^{6\alpha}$ are independently selected from the group consisting of hydrogen, lower alkyl, carboxy, heteroaryl, heterocycle, lower alkoxy, dialkylamino, and halogen, all of which can be optionally substituted by one or more selected from the group consisting of hydroxy, lower alkyl, hydroxyalkyl, aminoalkyl, amino, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be carboxy.

In a 61st embodiment, the invention is represented by Formula I or its pharmaceutically acceptable salt or ester, wherein:

$R^{2\beta}$, $R^{3\beta}$, $R^{4\beta}$, $R^{5\beta}$ and $R^{6\beta}$ are independently selected from the group consisting of hydrogen, lower alkyl, carboxy, lower alkoxy, and halogen;

$R^{2\alpha}$, $R^{3\alpha}$, $R^{4\alpha}$, $R^{5\alpha}$ and $R^{6\alpha}$ are independently selected from the group consisting of hydrogen, lower alkyl, heteroaryl, heterocycle, lower alkoxy, dialkylamino, and halogen all of which can be optionally substituted by one or more selected from the group consisting of hydroxy, methyl, hydroxymethyl, aminomethyl, amino, acyl, alkoxycarbonyl, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be carboxy.

In a 62nd embodiment, the invention is represented by Formula I or its pharmaceutically acceptable salt or ester, wherein:

$R^{2\beta}$, $R^{3\beta}$, $R^{4\beta}$, $R^{5\beta}$ and $R^{6\beta}$ are independently selected from the group consisting of hydrogen, lower alkyl, carboxy, lower alkoxy, and halogen;

$R^{2\alpha}$, $R^{3\alpha}$, $R^{4\alpha}$, $R^{5\alpha}$ and $R^{6\alpha}$ are independently selected from the group consisting of hydrogen, lower alkyl, heteroaryl, heterocycle, lower alkoxy, dialkylamino, and halogen;

wherein one of $R^{4\alpha}$, $R^{5\alpha}$ or $R^{6\alpha}$ must be a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\beta}$, $R^{3\beta}$, or $R^{4\beta}$ must be carboxy.

In a 63rd embodiment, the invention is represented by Formula I or its pharmaceutically acceptable salt or ester, wherein:

$R^{2\beta}$, $R^{3\beta}$, $R^{4\beta}$, $R^{5\beta}$ and $R^{6\beta}$ are independently selected from the group consisting of hydrogen, lower alkyl, carboxy, lower alkoxy, and halogen;

$R^{2\alpha}$, $R^{3\alpha}$, $R^{4\alpha}$, $R^{5\alpha}$ and $R^{6\alpha}$ are independently selected from the group consisting of hydrogen, lower alkyl, heteroaryl, heterocycle, lower alkoxy, dialkylamino, and halogen;

wherein one of $R^{4\alpha}$, $R^{5\alpha}$ or $R^{6\alpha}$ must be a carbon-carbon linked heterocycle selected from the group consisting of pyrrolidinyl, pyranyl, tetrahydrofuranyl, tetrahydropyranyl, pyranyl, piperidinyl, and piperazinyl;

with the proviso that at least one of $R^{2\beta}$, $R^{3\beta}$, or $R^{4\beta}$ must be carboxy.

In a 64th embodiment, the invention is represented by Formula I or its pharmaceutically acceptable salt or ester, wherein:

$R^{2\beta}$, $R^{3\beta}$, $R^{4\beta}$, $R^{5\beta}$ and $R^{6\beta}$ are independently selected from the group consisting of hydrogen, methyl, carboxy, methoxy, chloro and fluoro;

$R^{2\alpha}$, $R^{3\alpha}$, $R^{5\alpha}$, $R^{5\alpha}$ and $R^{6\alpha}$ are independently selected from the group consisting of hydrogen, methyl, furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, isoquinolinyl, methoxy, dimethylamino, chloro and fluoro;

wherein one of $R^{4\alpha}$, $R^{5\alpha}$ or $R^{6\alpha}$ must be a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl;

with the proviso that at least one of $R^{2\beta}$, $R^{3\beta}$, $R^{4\beta}$, $R^{5\beta}$ or $R^{6\beta}$ must be carboxy.

In a $65^{th}$ embodiment, the invention is represented by Formula I or its pharmaceutically acceptable salt or ester, wherein:

$R^{2\beta}$, $R^{3\beta}$, $R^{4\beta}$, $R^{5\beta}$ and $R^{6\beta}$ are independently selected from the group consisting of hydrogen, methyl, carboxy, methoxy, chloro and fluoro;

$R^{2\alpha}$, $R^{3\alpha}$, $R^{4\alpha}$, and $R^{6\alpha}$ are independently selected from the group consisting of hydrogen, methyl, methoxy, dimethylamino, chloro and fluoro;

$R^{5\alpha}$ is a carbon-carbon linked heteroaryl selected from the group consisting of furanyl, benzofuranyl, oxazolyl, thienyl, benzothienyl, indolyl, pyrrolyl, thiazolyl, imidazolyl, pyrimidinyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\beta}$, $R^{3\beta}$, or $R^{4\beta}$ must be carboxy.

In a 66th embodiment, the invention is represented by Formula I or its pharmaceutically acceptable salt or ester, wherein:

$R^{2\beta}$, $R^{3\beta}$, $R^{5\beta}$, $R^{6\beta}$ $R^{3\alpha}$, and $R^{6\alpha}$ are hydrogen;

$R^{4\beta}$ is carboxy;

$R^{2\alpha}$ and $R^{4\alpha}$ are methoxy; and $R^{5\alpha}$ is a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl.

In a 67th embodiment, the invention is represented by Formula I or its pharmaceutically acceptable salt or ester, wherein:

$R^{2\beta}$, $R^{3\beta}$, $R^{5\beta}$, $R^{6\beta}$, $R^{3\alpha}$, and $R^{6\alpha}$ are hydrogen;

$R^{4\beta}$ is carboxy;

$R^{2\alpha}$ and $R^{4\alpha}$ are methoxy; and $R^{5\alpha}$ is 5-(benzothien-2-yl).

In a 68th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, alkoxycarbonyl, acyl, oxo, acyl, alkoxycarbonyl and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be selected from the group consisting of $—NHR^2$, $—NH_2$, $—NHSO_2R^2$, $—N(R^2)_2$, $—NR^2C(O)R^2$, $—NHC(O)SR^2$, $—NHC(O)NHR^2$, $—NHC(O)N(R^2)_2$, $—NR^2SO_2R^2$, $—NHSO_2NHR^2$, $—NHC(O)R^2$, and $—NHC(O)OR^2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

In a 69th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, carbocycle, heteroaryl, heterocycle, cycloalkyl, tetrazol-5-yl, alkoxy, lower alkoxy, aryloxy, arylalkoxy, heteroaryloxy, heteroarylalkoxy, alkylthio, alkylamino, haloalkyl, acylamino, dialkylamino, haloalkoxy, halogen, alditol, carbohydrate, $—OC(R^1)_2COOH$, $—SC(R^1)_2COOH$, $—NHC(R^1)_2COOH$, $—COOR^1$, polyoxyalkylene, polyol alkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R$, $—N(R^2)C(O)R^2$, $—NHC(O)OR^2$, $—NHC(O)SR^2$, $—NHSO_2NHR^2$, $—P(R^2)O_2H$, $—NHSO_2R^2$, $—N(C(O)NHR^2)_2$, $—NRSO_2R^2$, $—NHC(O)NHR^2$, and $—NHC(O)N(R^2)_2$, all of which can be optionally substituted by one or more selected from the group consisting of hydroxy, lower alkyl, hydroxyalkyl, alkoxy, acyl, alkoxycarbonyl and halo;

$R^1$ is independently selected from the group consisting of hydrogen and lower alkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of lower alkyl, heterocycle, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be selected from the group consisting of $—NHR^2$, $—NH_2$, $—NHSO_2R^2$, $—N(R^2)_2$, and $—NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, hydroxyalkyl, alkoxy, and halo.

In a 70th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, lower alkyl, heterocycle, cycloalkyl, alkoxy, lower alkoxy, dialkylamino, halogen, hydroxyalkyl, heteroaryl lower alkoxy, heterocyclo lower alkoxy, heterocycleoxy, heterocyclo lower alkyl, cycloalkyloxy, —NHC(O)$R^2$, —$NHSO_2R^2$, all of which can be optionally substituted by one or more selected from the group consisting of hydroxy, lower alkyl, hydroxyalkyl, alkoxy, acyl, alkoxycarbonyl and halo;

$R^2$ is independently selected from the group consisting of lower alkyl, heterocycle, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be selected from the group consisting of —$NHR^2$, —$NH_2$, —$NHSO_2R^2$, —$N(R^2)_2$, and —$NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, hydroxyalkyl, alkoxy, and halo.

In a 71st embodiment, the invention is represented by Formula I or its pharmaceutically acceptable salt or ester, wherein:

$R^{2\alpha}$, $R^{3\alpha}$, $R^4$, $R^5$, $R^6$, $R^{2\beta}$, $R^{3\beta}$, $R^{4\beta}$, $R^{5\beta}$ and $R^{6\beta}$ are independently selected from the group consisting of hydrogen, lower alkyl, lower alkoxy, and halogen, all of which can be optionally substituted by one or more selected from the group consisting of hydroxy, lower alkyl, hydroxyalkyl, alkoxy, acyl, alkoxycarbonyl and halo;

$R^2$ is independently selected from the group consisting of lower alkyl wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\alpha}$, $R^{5\alpha}$ or $R^{6\alpha}$ must be a carbon-carbon linked heterocycle or heteroaryl;

with the proviso that at least one of $R^{2\beta}$, $R^{3\beta}$, or $R^{4\beta}$ must be selected from the group consisting of —$NHR^2$, —$NH_2$, —$NHSO_2R^2$, —$N(R^2)_2$, and —$NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, hydroxyalkyl, alkoxy, and halo.

In a 72nd embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —$C(O)R^2$, —$COOR^1$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, oxo, acetyl, carboalkoxy and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\alpha}$, $R^{5\alpha}$ or $R^{\alpha}$ must be a carbon-carbon linked heterocycle or heteroaryl;

wherein at least one of $R^{2\beta}$, $R^{3\beta}$, or $R^{4\beta}$ must be selected from the group consisting of —$SCH_2CO_2H$, —$SCF_2CO_2H$, —SH, —$SCH_3$, —$SO_2NH_2$, —$SO_2NHR^2$, and —$SO_2N(R^2)_2$.

In a 73rd embodiment, the invention is represented by Formula I or its pharmaceutically salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, haloalkyl, acylamino, amino, dialkylamino, haloalkoxy, alkylsulfonyl, haloalkylsulfonyl, halogen, thiol, alditol, carbohydrate, —$OC(R^1)_2COOH$, —$SC(R^1)_2COOH$, —$NHC(R^1)_2COOH$, —$COOR^1$, hydroxyalkyl, heteroaryl lower alkoxy, heterocyclo lower alkoxy, heterocycleoxy, heteroarylamino lower alkyl, heterocycloamino lower alkyl, arylamino, heterocycleamino, heteroarylamino, cycloalkylamino, cycloalkylalkyl, heterocyclealkoxy, cycloalkylalkoxy, cycloalkyloxy, cycloalkylaminoalkyl, —$C(O)NH_2$, —$C(O)NHR^2$, —$C(O)N(R^2)_2$, —$NHC(O)R^2$, —$N(R^2)C(O)R$, —$NHC(O)OR^2$, —$NHC(O)SR^2$, —$NHSO_2NHR^2$, —$SO_2NH_2$, —$SO_2NHR_2$, —$SO_2N(R^2)_2$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\alpha}$, $R^{5\alpha}$ or $R^{6\alpha}$ must be a carbon-carbon linked heterocycle or heteroaryl;

wherein at least one of $R^{2\beta}$, $R^{3\beta}$, or $R^{4\beta}$ must be selected from the group consisting of —$SCH_2CO_2H$, —$SCF_2CO_2H$, —SH, —$SCH_3$, —$SO_2NH_2$, —$SO_2NHR^2$, —$SO_2N(R^2)_2$, and $SC(R^1)_2COOH$.

In a 74th embodiment, the invention is represented by Formula I or its pharmaceutically salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, alkoxy, lower alkoxy, alkylthio, alkylamino, haloalkylthio, acylamino, amino, dialkylamino, alkylsulfonyl, haloalkylsulfonyl, halogen, thiol, —$SC(R^1)_2COOH$, hydroxyalkyl, cycloalkyloxy, cycloalkylaminoalkyl, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, oxo, acetyl, carboalkoxy and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\alpha}$, $R^{5\alpha}$ or $R^{6\alpha}$ must be a carbon-carbon linked heterocycle or heteroaryl;

wherein at least one of $R^{2\beta}$, $R^{3\beta}$, or $R^{4\beta}$ must be selected from the group consisting of —$SCH_2CO_2H$, —$SCF_2CO_2H$, —SH, —$SCH_3$, —$SO_2NH_2$, —$SO_2NHR^2$, —$SO_2N(R^2)_2$, and $SC(R^1)_2COOH$.

In a 75th embodiment, the invention is represented by Formula I or its pharmaceutically salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, lower alkyl, heteroaryl, heterocycle, lower alkoxy, alkylthio, acylamino, dialkylamino, alkylsulfonyl, haloalkylsulfonyl, halogen, thiol, —$SC(R^1)_2COOH$, hydroxyalkyl, —$SO_2NH_2$, —$SO_2NHR_2$, —$SO_2N(R^2)_2$, —$SCF_2CO_2H$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, oxo, acetyl, carboalkoxy and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\alpha}$, $R^{5\alpha}$ or $R^{6\alpha}$ must be a carbon-carbon linked heterocycle or heteroaryl;

wherein at least one of $R^{2\beta}$, $R^{3\beta}$, or $R^{4\beta}$ must be selected from the group consisting of —$SCH_2CO_2H$, —$SCF_2CO_2H$, —SH, —$SCH_3$, —$SO_2NH_2$, —$SO_2NHR^2$, —$SO_2N(R^2)_2$, and $SC(R^1)_2COOH$.

In a 76th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —$C(O)R^2$, —$COOR^1$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acetyl, carbalkoxy, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\alpha}$, $R^{5\alpha}$ or $R^{6\alpha}$ must be a carbon-carbon linked heterocycle or heteroaryl; and/or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $—OC(R^1)_2COOH$.

In a 77th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acetyl, carboalkoxy, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\alpha}$, $R^{5\alpha}$ or $R^{6\alpha}$ must be a carbon-carbon linked heterocycle or heteroaryl; and/or $R^{2\beta}$ and $R^{3\beta}$ taken together or $R^{3\beta}$ and $R^{4\beta}$ taken together or $R^{4\beta}$ and $R^{5\beta}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, oxo, and halo.

In a 78th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acetyl, carboalkoxy, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, oxo, and halo;

wherein one of $R^{4\alpha}$, $R^{5\alpha}$ or $R^{6\alpha}$ must be a carbon-carbon linked heterocycle or heteroaryl; and/or $R^{2\beta}$ and $R^{3\beta}$ taken together or $R^{3\beta}$ and $R^{4\beta}$ taken together or $R^{4\beta}$ and $R^{5\beta}$ taken together form a 5- to 6-membered heterocycle or heteroaryl containing one or more oxygen hetero atom, said heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, oxo, and halo.

Definitions

A wavy line used as a bond"∿∿∿", denotes a bond which can be either the E- or Z-geometric isomer.

When not used as a bond, the wavy line indicates the point of attachment of the particular substituent.

The terms "alkyl" or "alk", alone or in combination, unless otherwise specified, refers to a saturated straight or branched primary, secondary, or tertiary hydrocarbon from 1 to 10 carbon atoms, including, but not limited to methyl, ethyl, propyl, isopropyl, butyl, isobutyl, t-butyl, and sec-butyl. The term "lower alkyl" alone or in combination refers to an alkyl having from 1 to 4 carbon atoms. The alkyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene et al., *Protective Groups in Organic Synthesis*, John Wiley & Sons, Second Edition, 1991, hereby incorporated by reference. Specifically included are $CF_3$ and $CH_2CF_3$.

The term "alkenyl", alone or in combination, means a non-cyclic alkyl of 2 to 10 carbon atoms having one or more unsaturated carbon-carbon bonds. The alkenyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene et al., *Protective Groups in Organic Synthesis*, John Wiley & Sons, Second Edition, 1991, hereby incorporated by reference. Specifically included are $CF_3$ and $CH_2CF_3$.

The term "alkynyl", alone or in combination, means a non-cyclic alkyl of 2 to 10 carbon atoms having one or more triple carbon-carbon bonds, including but not limited to ethynyl and propynyl. The alkynyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene et al., *Protective Groups in Organic Synthesis*, John Wiley & Sons, Second Edition, 1991, hereby incorporated by reference. Specifically included are $CF_3$ and $CH_2CF_3$.

The terms "carboxy", "COOH" and "C(O)OH" are used interchangeably.

The terms "alkoxycarbonyl" and "carboalkoxy" are used interchangeably. Used alone or in combination, the terms mean refer to the radical —C(O)OR, wherein R is alkyl as defined herein.

The term "thio", alone or in combination, means the radical —S—.

The term "thiol", alone or in combination, means the radical —SH.

The term "hydroxy", alone or in combination means the radical —OH.

The term "sulfonyl", alone or in combination means the radical $—S(O)_2—$.

The term "oxo" refers to an oxygen attached by a double bond (═O).

The term "carbocycle", alone or in combination, means any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

The term "cycloalkyl", alone or in combination, means a saturated or partially unsaturated cyclic alkyl, having from 1 to 10 carbon atoms, including but not limited to mono- or bi-cyclic ring systems such as cyclopropyl, cyclobutyl, cyclopentyl, cyclohexenyl, and cyclohexyl.

The term "aryl", alone or in combination, means a carbocyclic aromatic system containing one, two or three rings wherein such rings may be attached together in a pendent manner or may be fused. The "aryl" group can be optionally substituted with one or more of the moieties selected from the group consisting of alkyl, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, halogen, haloalkylthi, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art, for example, as taught in Greene, et al., "Protective Groups in Organic Synthesis," John Wiley and Sons, Second Edition, 1999. In addition, adjacent groups on an "aryl" ring may combine to form a 5- to 7-membered saturated or partially unsaturated carbocyclic, aryl, heteroaryl or heterocyclic ring, which in turn may be substituted as above.

The term "heterocyclic", alone or in combination, refers to a nonaromatic cyclic group that may be partially (containing at least one double bond) or fully saturated and wherein the ring contains at least one heteroatom selected from oxygen, sulfur, nitrogen, or phosphorus. The terms "heteroaryl" or "heteroaromatic", alone or in combination, refer to an aromatic ring containing at least one heteroatom selected from sulfur, oxygen, nitrogen or phosphorus. The heteroaryl or heterocyclic ring may optionally be substituted by one or more substituent listed as optional substituents for aryl. In addition, adjacent groups on the heteroaryl or heterocyclic ring may combine to form a 5- to 7-membered carbocyclic, aryl, heteroaryl or heterocyclic ring, which in turn may be substituted as above. Nonlimiting examples of heterocylics and heteroaromatics are pyrrolidinyl, tetrahydrofuryl, tetrahydrofuranyl, pyranyl, purinyl, tetrahydropyranyl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl, aziridinyl, furyl, furanyl, pyridyl, pyridinyl, pyridazinyl, pyrimidinyl, benzoxazolyl, 1,2,4-oxadiazolyl, 1,3,4-oxadiazolyl, 1,3,4-thiadiazole, indazolyl, triazinayl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, 1,2,4-oxadiazolyl, 1,3,4-oxadiazolyl, pyrrolyl, quinazolinyl, quinoxalinyl, benzoxazolyl, quinolinyl, isoquinolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, triazolopyridinyl or pteridinyl wherein said heteroaryl or heterocyclic group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term "thienyl", alone or in combination, refers to a five member cyclic group wherein the ring contains one sulfur atom and two double bonds.

The term "benzothienyl", alone or in combination, refers to a five member cyclic group wherein the ring contains one sulfur atom and two double bonds fused to a phenyl ring.

The term "aryloxy", alone or in combination, refers to an aryl group bound to the molecule through an oxygen atom.

The term "heteroaryloxy", alone or in combination, refers to a heteroaryl group bound to the molecule through an oxygen atom.

The term "aralkoxy", alone or in combination, refers to an aryl group attached to an alkyl group which is attached to the molecule through an oxygen atom.

The term "heterocyclearalkoxy" refers to a heterocyclic group attached to an aryl group attached to an alkyl-O— group. The heterocyclic, aryl and alkyl groups can be optionally substituted as described above.

The terms "halo" and "halogen", alone or in combination, refer to chloro, bromo, iodo and fluoro.

The terms "alkoxy" or "alkylthio", alone or in combination, refers to an alkyl group as defined above bonded through an oxygen linkage (—O—) or a sulfur linkage (—S—), respectively. The terms "lower alkoxy" or "lower alkylthio", alone or, in combination, refers to a lower alkyl group as defined above bonded through an oxygen linkage (—O—) or a sulfur linkage (—S—), respectively.

The term "acyl", alone or in combination, refers to a group of the formula C(O)R', wherein R' is an alkyl, aryl, alkaryl or aralkyl group, or substituted alkyl, aryl, aralkyl or alkaryl, wherein these groups are as defined above.

The term "acetyl", alone or in combination, refers to the radical $—C(O)CH_3$.

The term "amino", alone or in combination, denotes the radical $—NH_2$ or —NH—.

The term "nitro", alone or in combination, denotes the radical $—NO_2$.

The term "substituted", means that one or more hydrogen on the designated atom or substituent is replaced with a selection from the indicated group, provided that the designated atom's normal valency is not exceeded, and the that the substitution results in a stable compound. When a subsitutent is "oxo" (keto) (i.e., ═O), then 2 hydrogens on the atom are replaced.

The term "alditol", as referred to herein, and unless otherwise specified, refers to a carbohydrate in which the aldehyde or ketone group has been reduced to an alcohol moiety. The alditols of the present invention can also be optionally substituted or deoxygenated at one or more positions. Exemplary substituents include hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, amino acid, amino acid esters and amides, phosphonyl, phosphinyl, phosphoryl, thioester, thioether, oxime, hydrazine, carbamate, phosphonic acid, and phosphonate. Particular exemplary substituents include amine and halo, particularly fluorine. The substituent or alditol can be either unprotected, or protected as necessary, as known to those skilled in the art, for example, as taught in Greene, et al, *Protective Groups in Organic Synthesis*, John Wiley and Sons, Second Edition, 1999, hereby incorporated by reference. The alditol may have 3, 4, 5, 6 or 7 carbons. Examples of useful alditols are those derived from reduction of monosaccharides, including specifically those derived from the reduction of pyranose and furanose sugars.

The term "carbohydrate", as referred to herein, and unless otherwise specified, refers to a compound of carbon, hydrogen and oxygen that contains an aldehyde or ketone group in combination with at least two hydroxyl groups. The carbohydrates of the present invention can also be optionally substituted or deoxygenated at one or more positions. Carbohydrates thus include substituted and unsubstituted monosaccharides, disaccharides, oligosaceharides, and polysaccharides. The saccharide can be an aldose or ketose, and may comprise 3, 4, 5, 6, or 7 carbons. In one embodiment the carbohydrates are monosaccharides. In another embodiment the carbohydrates are pyranose and furanose sugars.

As used herein, the term "patient" refers to warm-blooded animals or mammals, and in particular humans, who are in need of the therapy described herein. The term "host", as used herein, refers to a unicellular or multicellular organism, including cell lines and animals, and preferably a human.

Synthesis of the Active Compounds

Compounds of the present invention are prepared by reacting an aryl or cyclic substituted acid halide, ester, or amide with an aryl or cyclic substituted acetylene. This reaction is usually carried out under acid or base catalyzed conditions. The reaction may be suitably carried out in aprotic organic solvents such as ethers (e.g. tetrahydrofuran, dioxane, diethyl ether), or hydrocarbons (e.g. toluene, benzene), or chlorinated solvents (e.g. dichloromethane), or mixtures of such solvents. When carrying out the reaction under basic conditions, the base may be selected from sodium, lithium, and potassium hydride, or amides of secondary amines such as diisopropyl amides and methylphenyl amides. Alkyl lithium compounds such as methyl lithium or n-butyl lithium, organic magnesium compounds such as ethyl magnesium bromide or isopropyl magnesium bromide may also be used.

Acid catalysts may be selected from hydrogen chloride, hydrogen bromide, hydrogen iodide, sulfuric acid, sulfonic acids (such as paratoluenesulfonic or methansulfonic acid), lower carboxylic acids (such as formic, acetic, propionic acid), lower halogenated carboxylic acids (such as trifluoroacetic acid), Lewis acids (such as $AlCl_3$, $BF_3$, $POCl_3$, $PCl_5$, $FeCl_3$), or acid ion excange resins.

The reaction may be carried out at temperatures in the range of 100° C. to the boiling point of the solvent or so. The time of reaction may be from 5 minutes to 72 hours.

Compounds of the invention are also prepared in a 2-step synthesis, first by reacting an aryl or cyclic substituted aldehyde with an aryl or cyclic substituted acetylene to form a propargylic alcohol precursor, which is then oxidized to the corresponding 2-propyn-1-one. Formation of the propargylic alcohol precursor is usually carried out under basic conditions. The reaction may be suitably carried out in aprotic organic solvents such as ethers (e.g. tetrahydrofuran, dioxane, diethyl ether), or hydrocarbons (e.g. toluene, benzene), or mixtures of such solvents. The base may be selected from sodium, lithium, and potassium hydride, or amides of secondary amines such as diisopropyl amides and methylphenyl amides. Alkyl lithium compounds such as methyl lithium and n-butyl lithium, organic magnesium compounds such as ethyl magnesium bromide and isopropyl magnesium bromide may also be used.

The base reaction may usually be carried out at temperatures in the range of −78° C. to the boiling point of the solvent. The time of reaction may be from 5 minutes to 72 hours.

For oxidtion of the propargylic alcohol to the desired 2-propyn-1-one, there is no particular limitation imposed on the oxidizing agent. However, examples include metal oxides represented by $Met_mO_n$ (Met represents a metal such as manganese, nickel, tungsten, chromium, vanadium, titanium, silver, mercury, copper, lead or iron, m stands for 1–3 and n stands for 1–3), peroxides such as sodium hypochlorite, CAN (dicerium ammonium nitrate), DDQ (2,3-dichloro-5,6-dicyano-1,4-benzoquinone), chloranil (2,3,5,6-tetrachloro-1,4-benzoquinone), DMSO-pyridine sulfur trioxide complex, Jones' reagent, pyridiumium chlorochromate, pyridinium dichromate, dimethylsufoxide-oxalyl chloride, hydrogen peroxide or tert-butylhydroperoxide; and peracids such as performic acid, peracetic acid or metachloroperbenzoic acid. They may be used in combination. The reaction may be suitably carried out in water or protic organic solvents such as lower alcohols (e.g. methanol, ethanol, tert-butanol), or lower carboxylic acid (e.g. formic acid, glacial acetic acid, propionic acid), or in aprotic organic solvents such as ethers (e.g. tetrahydrofuran, dioxane, diethyl ether), liquid amides (e.g. dimethylformamide, hexanethylphosphordiamide), dimethylsulfoxide, hydrocarbons (e.g. toluene, benzene), or mixtures of such solvents.

The above reaction may usually be carried out at temperatures in the range of −20° C. to the boiling point of the solvent. The time of reaction may be from 5 minutes to 72 hours.

In the above reactions, it may be preferred or necessary to protect various sensitive or reactive groups present in the starting materials so as to prevent said groups from interfering with the reactions. Such protection may be carried out in a well-known manner as taught by Theodora Green et al., in "Protective Groups in Organic Chemistry" (Wiley, 1999) or of the like. The protecting group may be removed after the reaction in a manner known per se.

The 1,3-bis-(substituted-phenyl)-2-propyn-1-one compounds of the present invention can be readily prepared by someone skilled in the art of organic synthesis using commonly known methods many of which are described by R. Dinerstein in EP 0476658 and J. Bernardon in U.S. Pat. No. 6,162,445, incorporated herein by reference. General synthetic procedures for preparing the compounds of the inventin are set forth in the following Schemes. As shown in Scheme 1, a substituted acid chloride, ester, or amide is reacted with a substituted acetylene in the presence of a suitable non-nucleophilic base, such as n-butyllithium, lithium hexamethyldisilizane, or lithium diisopropylamide. The reaction can be carried out in a variety of different aprotic solvents, such as tetrahydrofuran. On either or both of the phenyl rings there is a heteroaryl or heterocyclic substituent.

As shown in Scheme 2, the reaction can also be carried in the presence of a Lewis acid. A variety of Lewis acids can be used. $AlCl_3$ is the preferred acid. This reaction is particularly useful when there are one or more base sensitive substitutions on either one or both of the phenyl rings.

The compounds of the present invention can also be readily prepared as shown in Scheme 3. Typically a substituted aldehyde is reacted with a substituted acetylene in the presence of a suitable non-nucleophilic base, such as n-butyllithium, lithium hexamethyldisilzane, or lithium diisopropylamide. The reaction can be carried out in a variety of different aprotic solvents, such as tetrahydrofuran. The resulting propargylic alcohol is then oxidized in the presence of a suitable oxidizing agent, such as pyridiunium dichromate, manganese dioxide, or dimethylsufoxide-oxalyl chloride. On either or both of the phenyl rings there is a heteroaryl or heterocyclic substituent.

Phenylacetylene compounds can be readily prepared by someone skilled in the art of organic synthesis using commonly known methods, many of which are described by L. Brandsma et al. in *Preparative Acetylenic Chemistry* (Elsevier Science, 1988), that is incorporated herein by reference. A variety of acetylenic forming reactions can be used. The Corey-Fuchs reaction is preferred, and general methods for this procedure are described by Corey et. al. in *Tetrahedron Lett.* (1972), 3769–3772. In general, a heteroaryl or heterocyclic ring substituted phenylacetylene compound can be prepared according to Scheme 4 in a 3-step process. In step "a", the heteroaryl or heterocyclic ring is introduced by replacing the halogen substitution or triflate substitution on the phenyl ring through a metal-catalyzed cross-coupling carbon-carbon bond forming reaction well known in the art of organic chemistry. A variety of metal-catalyzed cross coupling carbon-carbon bond forming reactions can be used. The palladium-catalyzed Suzuki reaction is preferred, and general methods for this procedure are described by A. Suzuki in Recent Advances in the Cross-Coupling Reactions of Organoboron Derivatives with Organic Electrophiles, 1995–1998 (*J. Organomet. Chem.* (1999), 576(1–2), 147–168), incorporated herein by reference. For the Suzuki reaction, a variety of solvents can be used. The preferred solvent for the Suzuki coupling is ethylene glycol dimethyl ether (DME) for the aqueous conditions and THF is preferred for the non-aqueous. In Scheme 4 step "b", the appropriate 2',2'-dibromostyrene compound can be prepared by reacting the appropriate benzaldehyde compound with carbon tetrabromide and triphenylphosphine in a suitable aprotic sovent, such as dichloromethane. In step "c", the appropriate phenylacetylene compound can be prepared by reacting the appropriate 2',2'-dibromostyrene compound with a non-nucleophilic base, such as n-butyl lithium, in a suitable aprotic sovent, such as tetrahydrofuran.

Some benzaldehydes are not commercially available. They can be readily prepared by someone skilled in the art of organic synthesis. As shown in Schemes 5, the heteroaryl or heterocyclic ring is introduced to the benzaldehyde intermediate by replacing the halogen substitution or triflate substitution on the phenyl ring through a metal-catalyzed cross-coupling carbon-carbon bond forming reaction well known in the art of organic chemistry. A variety of metal-catalyzed cross coupling carbon-carbon bond forming reactions can be used. The palladium-catalyzed Suzuki reaction is preferred, and general methods for this procedure are described by A. Suzuki in Recent Advances in the Cross-Coupling Reactions of Organoboron Derivatives with Organic Electrophiles, 1995–1998 (*J. Organomet. Chem.* (1999), 576(1–2), 147–168), incorporated herein by reference. For the Suzuki reaction, a variety of solvents can be used. The preferred solvent for the Suzuki coupling is ethylene glycol dimethyl ether (DME) for the aqueous conditions and THF for the non-aqueous conditions.

Since the pheylacetylenes or benzaldehydes may also contain one or more water solubilizing groups (amines, acohols, carboxylates, phosphates, phosphonates, sulfonates, sulfates, etc) that may interfere in the reaction or that may complicate isolation of the desired produict, one normally skilled in the art may choose to protect these solubilizing groups prior to the reaction using methods commonly known in the literature such as those described by T. W. Greene and P. G. M. Wuts in *Protective Groups in Organic Synthesis* (Wiley, New York, 1999) and A. J. Pearson and W. R. Roush in *Handbook of Reagents for Organic Synthesis: Activating and Agents and Protecting Groups* (Wiley, Chichester, UK, 1999), incorporated herein by reference. Preferable protecting groups include acetates to protect alcohols, esters to protect carboxylic acids, and amides or carbamates to protect amines. Compounds of the present invention include the resulting protected intermediates. One skilled in the art can selectively remove these protecting groups using well established and known procedures to give the desired deprotected heteroaryl or heterocyclic 1,3-bis-(substituted-phenyl)-2-propyn-1-one products. Some protecting groups such as carboxylic esters may be removed prior to the oxidation reaction. Formation of the resulting carboxylate salts, e.g. the sodium salt, may facilitate isolation of the desired heteroaryl or heterocyclic 1,3-bis-(substituted-phenyl)-2-propyn-1-one products from the reaction mixture. Alternatively, acidification of the reaction mixture prior to or during workup may facilitate the isolation of the desired free carboxylic, phosphonic, phosphinic or sulfonic acid derivatives. Various salts of the compounds of this invention can be prepared by someone skilled in the art of organic synthesis. Such salts, e.g. amine hydrochlorides, can be directly isolated from the reaction mixture after acidification or formed separately after isolation of the corresponding free amine.

The chemical reactions described above are generally disclosed in terms of their broadest applications to the preparation of the compounds of the present invention. Occasionally, the reactions may not be applicable as described to each compound included within the disclosed scope. The compounds for which this occurs will be readily recognized by those skilled in the art. In all such cases, either the reactions can successfully performed by conventional modifications recognized by those skilled in the art, e.g., by appropriate protection and deprotection of interfering groups, by changing to alternative conventional solvents or reagents, by routine modification of reaction conditions and the like, or other conventional reactions. Compounds of the present invention may be isolated or synthesized in accordance with methods from literature or methods analogous thereto, and non-limiting examples are taught either by Wade et al, *Organic Chemistry Third Edition,* 1995 or by Smith and March in March's *Advanced Organic Chemistry Fifth Edition* (Wiley, 2001), or references cited therein. In all preparative-methods, all starting materials are known or readily prepared from known starting materials.

The following schemes will prove useful to those skilled in the art:

R=1 to 5 substituents previously defined as $R^{2\beta}$, $R^{3\beta}$, $R^{4\beta}$, $R^{5\beta}$, and $R^{6\beta}$.

R'=1 to 5 substituents previously defined as $R^{2\alpha}$, $R^{3\alpha}$, $R^{4\alpha}$, $R^{5\alpha}$, and $R^{6\alpha}$.

Z=a leaving group.

Scheme 1

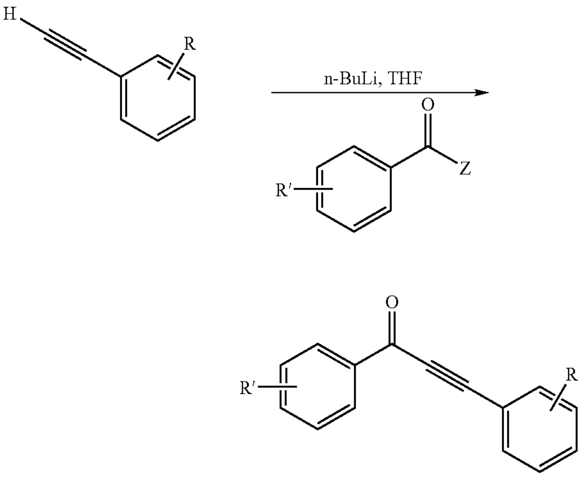

Scheme 2

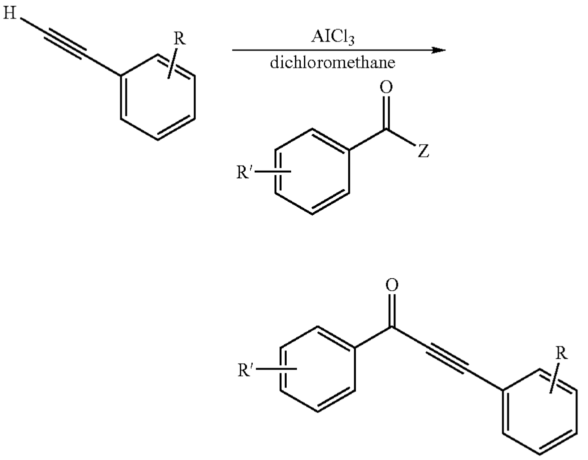

Scheme 3
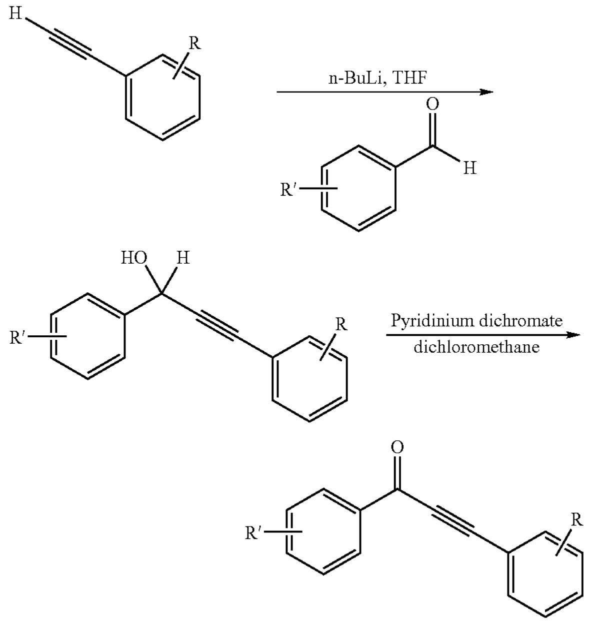
Scheme 4
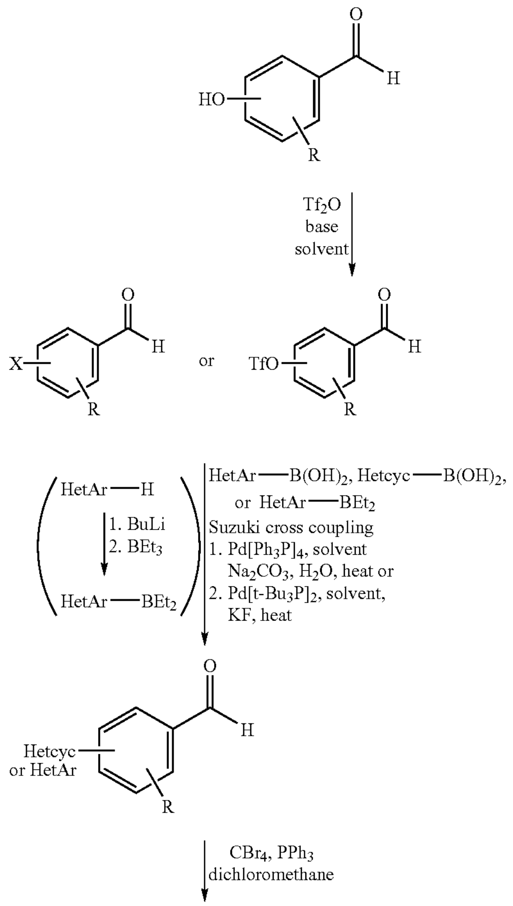
-continued
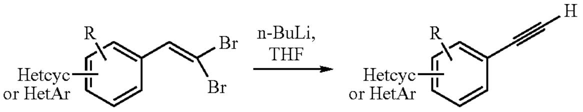
Scheme 5
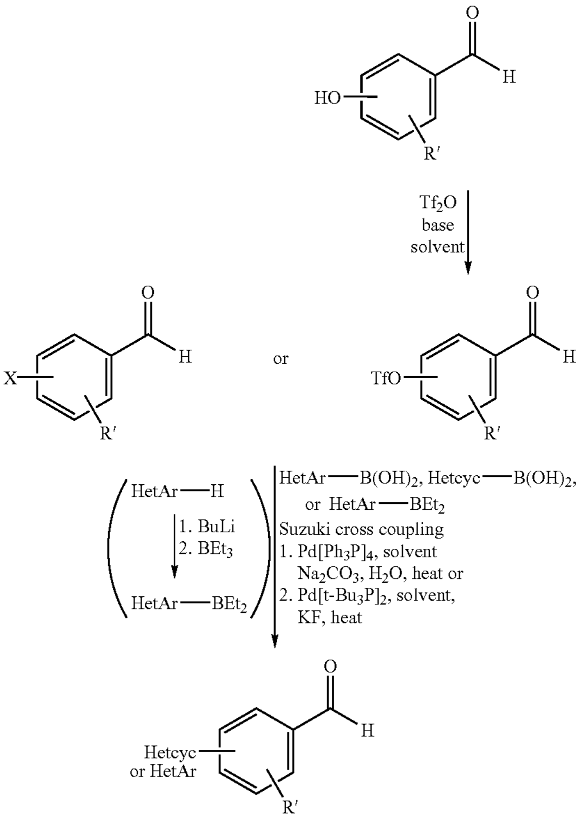
EXAMPLES
The following examples are understood to be illustrative only and are not intended to limit the scope of the present invention in any way. All intermediates and final products have been completely characterized by conventional proton NMR and standard analytical methods known to those skilled in the art.
Example 1
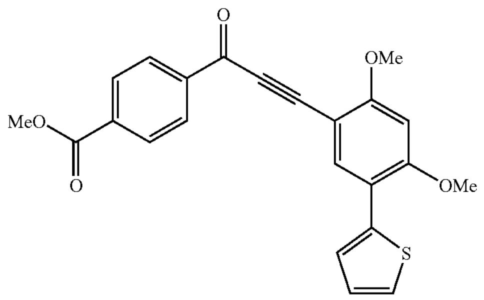

4-[3-(2,4-dimethoxy-5-thiophen-2-yl-phenyl)-propynoyl]-benzoic acid methyl ester Ex-1A: A solution of 5-bromo-2,4-dimethoxy-benzaldehyde (10.0 g, 40.80 mmol) and thiophene-2-boronic acid (7.8 g, 60.96 mmol) in ethylene glycol dimethyl ether (250 mL) was stirred at room temperature under nitrogen for 15 min. Tetrakis(triphenylphosphine)-palladium(0) (4.85 g, 4.19 mmol) and a sodium carbonate solution (2 M, 70 mL) were then added, and the resulting mixture was refluxed under nitrogen overnight. Upon codling to room temperature the reaction was poured into water (250 mL) and extracted with dichloromethane (2×250 mL). The organic phase was dried over sodium sulfate, filtered, and the solvent was removed under reduced pressure. Silica gel chromatography (hexane/ethyl acetate, 3:1) gave 9.2 g (91%) of the desired 2,4-dimethoxy-5-thiophen-2-yl-benzaldehyde product as a pale yellow solid, m.p. 125–126° C. $^1$H-NMR (300 MHz, $CDCl_3$) δ 10.34 (s, 1H), 8.12 (s, 1H), 7.44 (dd, 1H, J=3.5 and 1.5 Hz), 7.31 (dd, 1H, J=5.2 and 1.5 Hz), 7.07 (dd, 1H, J=5.2 and 3.5 Hz), 6.51 (s, 1H), 4.02 (s, 3H), 3.99 (s, 3H)

An alternative procedure: 5-bromo-2,4-dimethoxybenzaldehyde (20.3 g), thiophene-2-boronic acid (11.6 g) and THF (200 mL) were sequentially charged into a clean reaction vessel fitted with a reflux condenser, mechanical stirrer and nitrogen inlet adapter. Nitrogen was bubbled into the resulting solution for 20 min followed by the sequential addition of KF (10.1 g), and $Pd(^tBu_3P)_2$ (0.424 g). The solution was immediately heated to 60° C. and aged for 1.5 h. The reaction was diluted with $H_2O$ (200 mL) and transferred to a separatory funnel containing EtOAc (200 mL) and $H_2O$ (200 mL). The layers were cut and the aqueous layer was extracted with EtOAc (100 mL). The combined organic cuts were filtered through a pre-washed pad of solka floe (5 g). The pad of solka floe and spent catalyst were washed with fresh EtOAc (200 mL) and this wash combined with the batch. The resultant filtrate was concentrated to dryness. The crude product was dissolved in THF (38 mL) and crystallized upon heptane (152 mL) addition. The product was filtered and then dried to a constant weight in the vacuum oven (38° C., 20 mHg) affording 19.32 g (94% yield) of desired 2,4-dimethoxy-5-thiophen-2-yl-benzaldehyde as a light off-white solid. $^1$H-NMR identical as above.

Ex-1B: A solution of triphenylphosphine (8.64 g, 32.9 mmol) and $CBr_4$ (5.4 g, 16.3 mmol) in 140 mL of dichloromethane was stirred at room temperature for 15 min. Then 2,4-dimethoxy-5-thiophen-2-yl-benzaldehyde (3.1 g, 12.5 mmol) from Ex-1A was added, and the mixture was stirred overnight. The solvent was reduced to 30 mL and then filtered through silica gel with hexanes as eluent. After evaporation of the solvents, the crude 2-[5-(2,2-dibromo-vinyl)-2,4-dimethoxy-phenyl]-thiophene was dissolved in THF (40 mL) and cooled to −78° C. Then n-butyllithium (25.6 mmol, 16 mL of a 1.6 M solution in hexanes) was added dropwise while maintaining an internal temperature below −70° C. After stirring the reaction mixture for 1 h at −78° C., the reaction was quenched with a saturated $NH_4Cl$ solution. This solution was extracted with ethyl acetate, and the organic layer was dried over anhydrous magnesium sulfate. The solvent was removed under reduced pressure, and the residue was chromatographed on silica gel (hexane/ethyl acetate, 1:1) to give 2.05 g (67%) of 2-(5-ethynyl-2,4-dimethoxy-phenyl)-thiophene as a yellow solid, m.p. 141–142° C. $^1$H-NMR (300 MHz, $CDCl_3$) δ 7.73 (s, 1H), 7.38 (dd, 1H, J=3.7 and 1.3 Hz), 7.28 (dd, 1H, J=5.2 and 1.3 Hz), 7.06 (dd, 1H, J=5.2 and 3.7 Hz), 6.51 (s, 1H), 3.96 (s, 6H), 3.27 (s, 1H).

Ex-1C: A solution of 2-(5-ethynyl-2,4-dimethoxy-phenyl)-thiophene (1.5 g, 6.14 mmol) from Ex-1B in THF (20 mL) was cooled to −78° C. n-Butyllithium (6.72 mmol, 4.2 mL of a 1.6 M solution in hexanes) was added dropwise while maintaining an internal temperature below −65° C. After aging for 30 min at −78° C., the reaction was transferred via cannula over 10 min to a cold (−78° C.) solution of methyl 4-formylbenzoate (1.07 g, 6.52 mmol) in THF (10 mL). The resulting solution was slowly warmed to 0° C. and then quenched with a saturated $NH_4Cl$ solution. The layers were separated, and the aqueous layer was extracted with ethyl acetate. The combined organic phases were dried over anhydrous magnesium sulfate, and the solvent was removed under reduced pressure. Silica gel chromatography (hexane/ethyl acetate, 3:1, 1:1) gave 2.2 g (88%) of the desired 4-[3-(2,4-dimethoxy-5-thiophen-2-yl-phenyl)-1-hydroxy-prop-2-ynyl]-benzoic acid methyl ester as a greenish yellow solid, m.p. 128–130° C. $^1$H-NMR (300 MHz, $CDCl_3$) d 8.08 (d, 2H, J=8.3 Hz), 7.75 (d, 2H, J=8.3 Hz), 7.68 (s, 1H), 7.37 (dd, 1H, J=3.6 and 1.7 Hz), 7.28 (dd, 1H, J=5.1 and 1.7 Hz), 7.06 (dd, 1H, J=5.1 and 3.6 Hz), 5.79 (d, 1H, J=6.6 Hz), 3.96 (s, 3H), 3.94 (s, 3H), 3.93 (s, 3H), 2.53 (d, 1H, J=6.6 Hz).

4-[3-(2,4-Dimethoxy-5-thiophen-2-yl-phenyl)-1-hydroxy-prop-2-ynyl]-benzoic acid methyl ester (2.0 g, 4.90 mmol) from Ex-1C was dissolved in dichloromethane (60 mL). Pyridinium dichromate (3.70 g, 9.8 mmol) was added and the resulting mixture was stirred at room temperature under nitrogen for 5 h. The reaction was then filtered through a pad of celite and concentrated under reduced pressure. Silica gel chromatography (dichloromethane/methanol, 30:1) gave 1.5 g (75%) of the desired 4-[3-(2,4-dimethoxy-5-thiophen-2-yl-phenyl)-propynoyl]-benzoic acid methyl ester as a yellow solid, m.p. 198–200° C. $^1$H-NMR (300 MHz, $CDCl_3$) δ 8.38 (d, 2H, J=8.0 Hz), 8.17 (d, 2H, J=8.0 Hz), 0.88 (s, 1H), 7.41 (dd, 1H, J=3.7 and 1.6 Hz), 7.33 (dd, 1H, J=5.2 and 1.6 Hz), 7.09 (dd, 1H, J=5.2 and 3.7 Hz), 6.55 (s, 1H), 4.05 (s, 3H), 4.01 (s, 3H), 4.00 (s, 31H); EIMS m/z 406 (M+).

Example 2

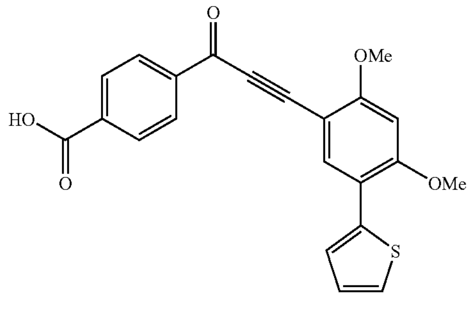

4-[3-{2,4-Dimethoxy-5-(thiophen-2-yl)-phenyl}propynoyl]-benzoic Acid

4-[3-(2,4-dimethoxy-5-thiophen-2-yl-phenyl)-propynoyl]-benzoic acid methyl ester (50 mg, 0.12 mmol) from Ex-1 was dissolved in THF (2 mL) and methanol (2 mL). Sodium hydroxide solution (1 N, 1 mL) was added and the resulting solution was stirred at room termperature under nitrogen for 1 h. The reaction was then diluted with water (10 mL) and washed with ethyl acetate (10 mL). The aqueous phase was acidified with conc. HCl and extracted with ethyl acetate (2×10 mL). The organic phase was dried over magnesium sulfate and concentrated under reduced pressure to afford 20 mg (42%) of the desired 4-[3-(2,4-dimethoxy-5-thiophen-2-yl-phenyl)-propynoyl]-benzoic acid as a yellow solid, m.p. 220° C. with decomposition. $^1$H-NMR (300 MHz, $d_6$-DMSO) δ 8.30 (d, 2H, J=8.0 Hz), 8.14 (d, 2H, J=8.0 Hz), 8.01 (s, 1H), 7.58 (m, 1H), 7.50 (m, 1H), 7.08 (m, 1H), 6.88 (s, 1H), 4.04 (s, 3H), 4.02 (s, 3H); EIMS m/z 392 (M+).

Example 3

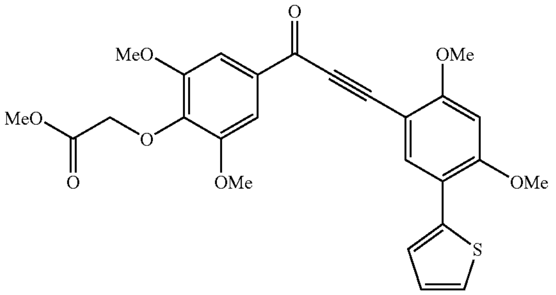

{4-[3-(2,4-Dimethoxy-5-thiophen-2-yl-phenyl)-propynoyl]-2,6-dimethoxy-phenoxy}-acetic acid methyl ester Ex-3A: 4-Hydroxy-3,5-dimethoxy-benzaldehyde (10.0 g, 54.89 mmol) was dissolved in DMF (100 mL). Bromo-acetic acid methyl ester (9.12 g, 59.62 mmol) and $K_2CO_3$ (15.0 g, 108.53 mmol) were then added and the resulting solution was stirred under nitrogen at 65° C. overnight. The reaction was then diluted with water and ethyl acetate and the layers were cut. The organic phase was washed with 1N HCl, dried over magnesium sulfate and concentrated under reduced pressure to afford 10.89 g (78%) of the desired (4-formyl-2,6-dimethoxy-phenoxy)-acetic acid methyl ester as a white solid, m.p. 99–100° C. $^1$H-NMR (300 MHz, $CDCl_3$) δ 9.87 (s, 1H), 7.12 (s, 2H), 4.76 (s, 2H), 3.92 (s, 6H), 3.80 (s, 3H).

Ex-3: A solution of 2-(5-ethynyl-2,4-dimethoxy-phenyl)-thiophene (1.0 g, 4.09 mmol) from Ex-1B in THF (35 mL) was cooled to −78° C. n-Butyllithium (4.62 mmol, 1.85 mL of a 2.5 M solution in hexanes) was added over 15 min while maintaining an internal temperature below −50° C. After aging for 15 min at −78° C., the reaction was transferred via cannula over 5 min to a cold (−78° C.) solution of (4-formyl-2,6-dimethoxy-phenoxy)-acetic acid methyl ester (1.15 g, 4.52 mmol) from Ex-3A in THF (25 mL). The resulting solution was slowly warmed to room temperature and then quenched with a saturated $NH_4Cl$ solution. The layers were separated, and the aqueous layer was extracted with ethyl acetate. The combined organic phases were dried over anhydrous magnesium sulfate, and the solvent was removed under reduced pressure The resulting crude {4-[3-(2,4-dimethoxy-5-thiophen-2-yl-phenyl)-1-hydroxy-prop-2-ynyl]-2,6-dimethoxy-phenoxy}-acetic acid methyl ester was dissolved in dichloromethane (50 mL), charged with pyridinium dichromate (3.00 g, 7.97 mmol) and aged at room temperature under nitrogen for 2.5 h. The reaction was then filtered through a pad of celite using additional dichloromethane and then ethyl acetate. The combined organic was concentrated under reduced pressure. Silica gel chromatography (ethyl acetate/hexane, 3:2) gave 1.0 g (49%) of the desired {4-[3-(2,4-dimethoxy-5-thiophen-2-yl-phenyl)-propynoyl]-2,6-dimethoxy-phenoxy}-acetic acid methyl ester as a yellow solid, m.p. 153–155° C. $^1$H-NMR (300 MHz, $CDCl_3$) δ 7.89 (s, 1H), 7.60 (s, 2H), 7.41 (dd, 1H, J=3.6 and 1.5 Hz), 7.35 (dd, 1H, J=5.3 and 1.5 Hz), 7.09 (dd, 1H, J=5.3 and 3.6 Hz), 6.54 (s, 1H), 4.77 (s, 2H), 4.01 (s, 3H), 3.99 (s, 3H), 3.97 (s, 6H), 3.82 (s, 3H).

Example 4

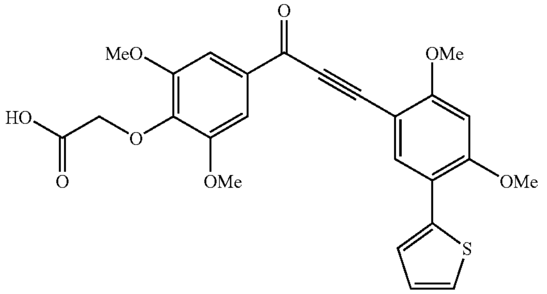

{4-[3-(2,4-Dimethoxy-5-thiophen-2-yl-phenyl)-propynoyl]-2,6-dimethoxy-phenoxy}-acetic acid Ex-4: {4-[3-(2,4-dimethoxy-5-thiophen-2-yl-phenyl)-propynoyl]-2,6-dimethoxy-phenoxy}-acetic acid methyl ester (500 mg, 1.01 mmol) from Ex-3 was dissolved in THF (5 mL) and methanol (5 mL). Sodium hydroxide solution (1 N, 5 mL) was added and the resulting solution was stirred at room termperature under nitrogen for 30 min. The reaction-was then diluted with 1 N HCl and isopropyl acetate and the layers cut. The organic phase was concentrated to dryness under reduced pressure, diluted with a small amount of ethanol and filtered to afford 350 mg (73%) of the desired {4-[3-(2,4-dimethoxy-5-thiophen-2-yl-phenyl)-propynoyl]-2,6-dimethoxy-phenoxy}-acetic acid as a yellow solid, m.p. 192–194° C. $^1$H-NMR (300 MHz, $d_6$-DMSO) δ 7.95 (s, 1H), 7.56 (dd, 1H, J=3.5 and 1.4 Hz), 7.49 (m, 1H), 7.47 (s, 2H), 7.07 (dd, 1H, J=5.1 and 3.5 Hz), 6.86 (s, 1H), 4.61 (s, 2H), 4.00 (s, 3H), 3.97 (s, 3H), 3.84 (s, 6H).

Using one or more of the preceding methods, additional compounds of the invention can be prepared by one skilled in the art. Particular compounds are listed in the following Example Tables:

Example Table 1
Substituted 4-[3-{(5-Heteroaryl or 5-heterocyclic)-2,4-dimethoxyphenyl}-propynoyl]-benzoic Acids
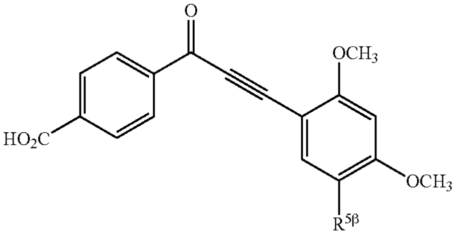
| Ex. No. | $R^{5\beta}$ |
|---|---|
| 201 | 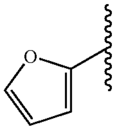 |
| 202 | 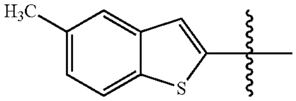 |
| 203 | 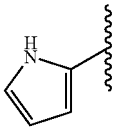 |
| 204 | 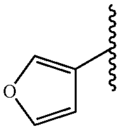 |
| 205 | 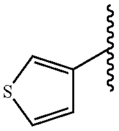 |
| 206 | 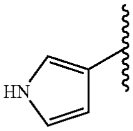 |
| 207 | 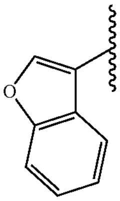 |
-continued
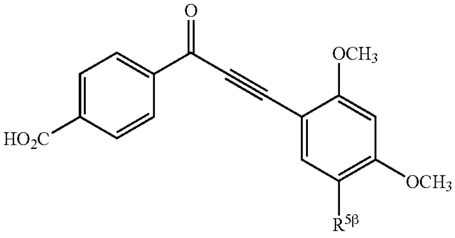
| Ex. No. | $R^{5\beta}$ |
|---|---|
| 208 | 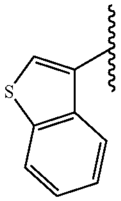 |
| 209 | 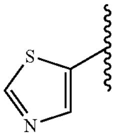 |
| 210 | 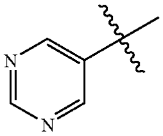 |
| 211 | 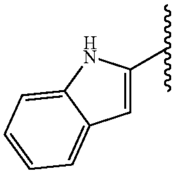 |
| 212 | 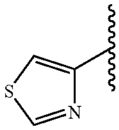 |
| 213 | 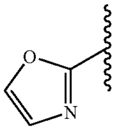 |
| 214 | 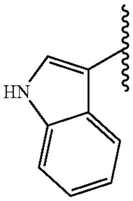 |

-continued
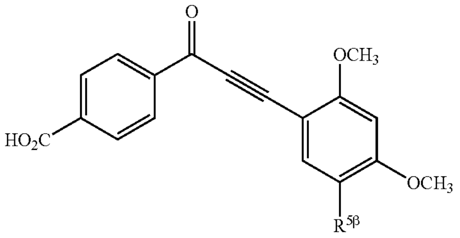
| Ex. No. | $R^{5\beta}$ |
| --- | --- |
| 215 | 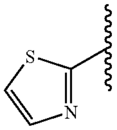 |
| 216 | 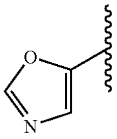 |
| 217 | 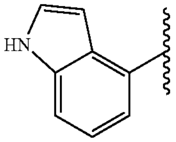 |
| 218 | 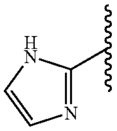 |
| 219 | 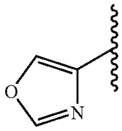 |
| 220 | 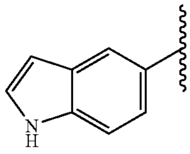 |
| 221 | 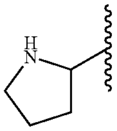 |
| 222 | 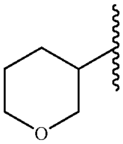 |
-continued
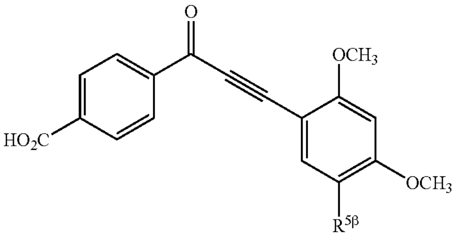
| Ex. No. | $R^{5\beta}$ |
| --- | --- |
| 223 | 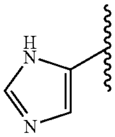 |
| 224 | 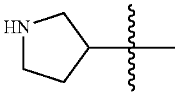 |
| 225 | 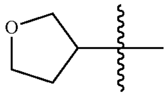 |
| 226 | 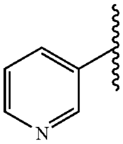 |
| 227 | 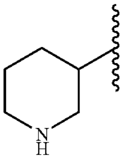 |
| 228 | 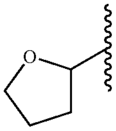 |
| 229 | 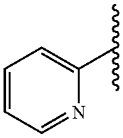 |
| 230 | 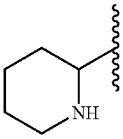 |
| 231 | 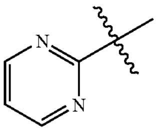 |

-continued
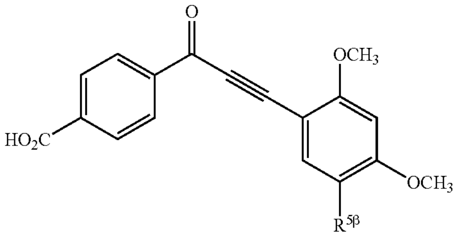
| Ex. No. | $R^{5\beta}$ |
| --- | --- |
| 232 | 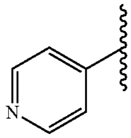 |
| 233 | 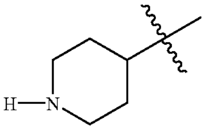 |
| 234 | 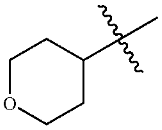 |
| 235 | 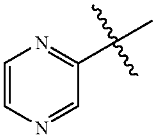 |
| 236 | 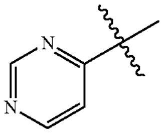 |
| 237 | 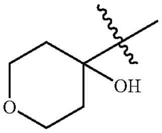 |
| 238 | 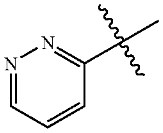 |
| 239 | 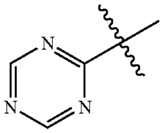 |
| 240 | 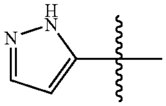 |
-continued
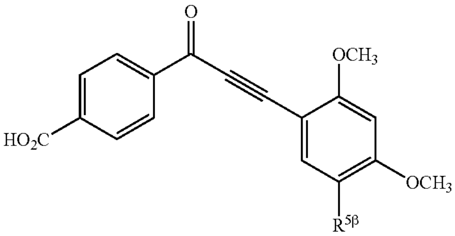
| Ex. No. | $R^{5\beta}$ |
| --- | --- |
| 241 | 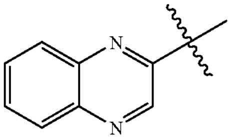 |
| 242 | 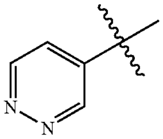 |
| 243 | 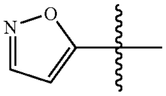 |
| 244 | 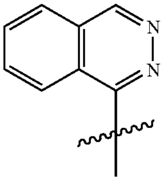 |
| 245 | 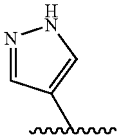 |
| 246 | 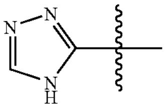 |
| 247 | 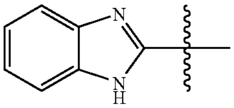 |
| 248 | 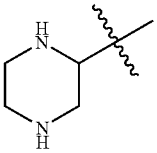 |
| 249 | 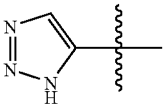 |

-continued
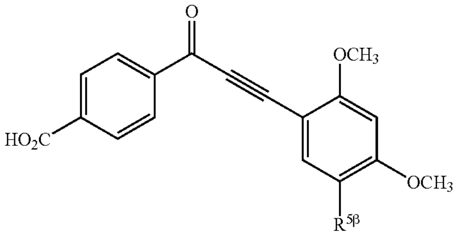
| Ex. No. | $R^{5\beta}$ |
|---|---|
| 250 | 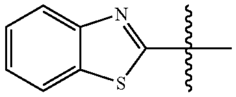 |
| 251 | 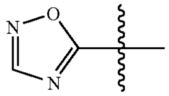 |
| 252 | 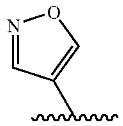 |
| 253 | 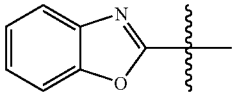 |
| 254 | 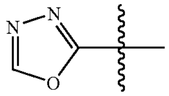 |
| 255 | 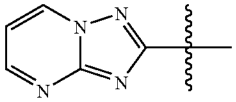 |
| 256 | 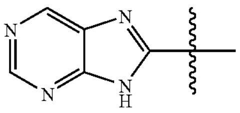 |
| 257 | 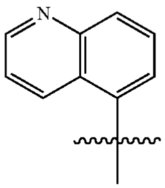 |
| 258 | 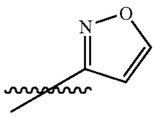 |
-continued
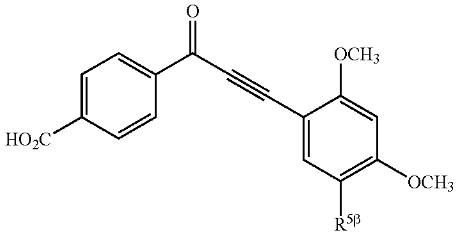
| Ex. No. | $R^{5\beta}$ |
|---|---|
| 259 | 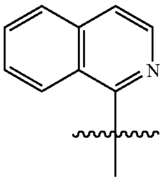 |
| 260 | 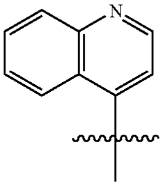 |
| 261 | 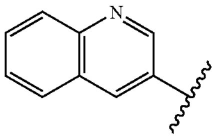 |
| 262 | 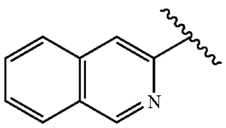 |
| 263 | 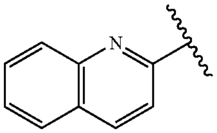 |
| 264 | 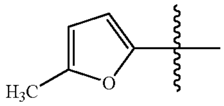 |
| 265 | 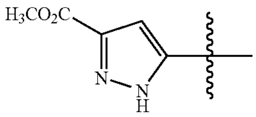 |
| 266 | 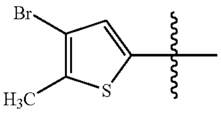 |

-continued
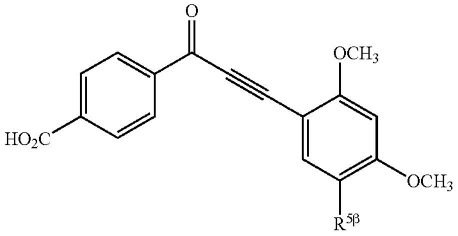
| Ex. No. | $R^{5\beta}$ |
| --- | --- |
| 267 | 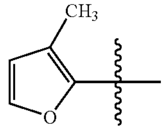 |
| 268 | 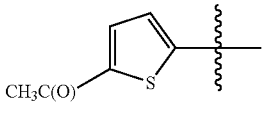 |
| 269 | 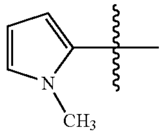 |
| 270 | 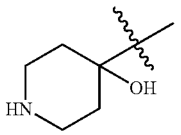 |
| 271 | 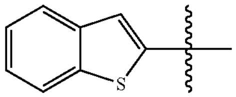 |
| 272 | 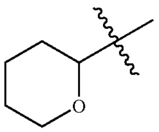 |
Example Table 2
Substituted. 3-[3-{(5-Heteroaryl or 5-heterocyclic)-2,4-dimethoxyphenyl}-propynoyl]-benzoic Acids
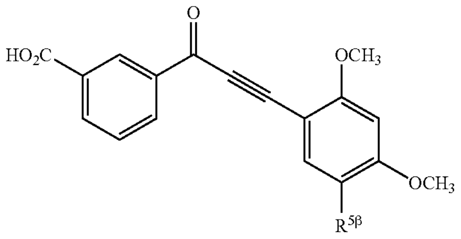
| Ex. No. | $R^{5\beta}$ |
| --- | --- |
| 273 | 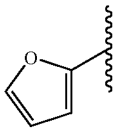 |
| 274 | 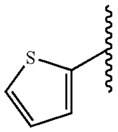 |
| 275 | 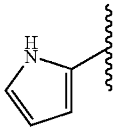 |
| 276 | 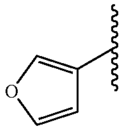 |
| 277 | 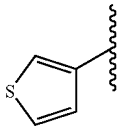 |
| 278 | 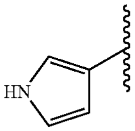 |
| 279 | 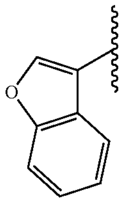 |

-continued
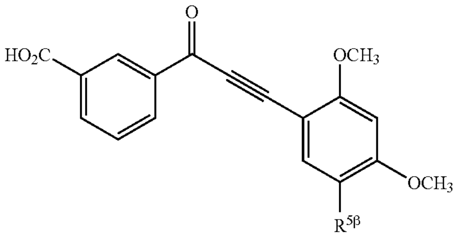
| Ex. No. | $R^{5\beta}$ |
|---|---|
| 280 | 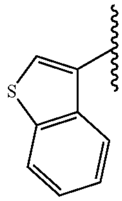 |
| 281 | 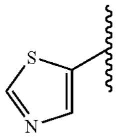 |
| 282 | 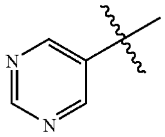 |
| 283 | 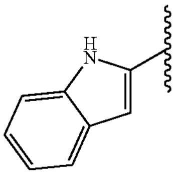 |
| 284 | 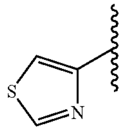 |
| 285 | 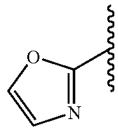 |
| 286 | 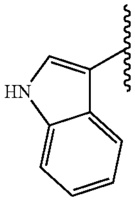 |
-continued
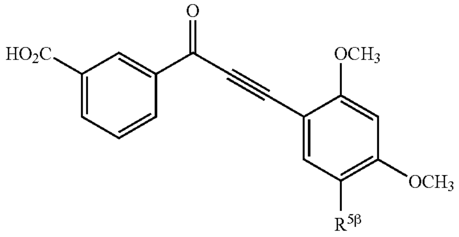
| Ex. No. | $R^{5\beta}$ |
|---|---|
| 287 | 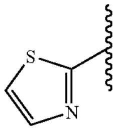 |
| 288 | 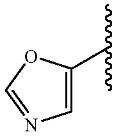 |
| 289 | 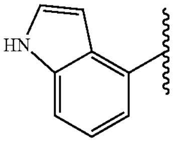 |
| 290 | 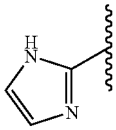 |
| 291 | 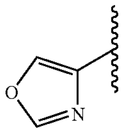 |
| 292 | 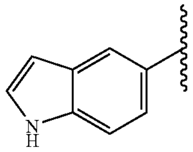 |
| 293 | 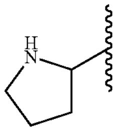 |
| 294 | 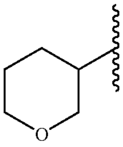 |

-continued
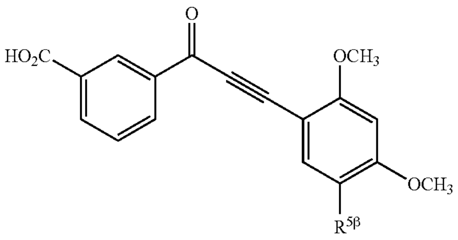
| Ex. No. | $R^{5\beta}$ |
|---|---|
| 295 | 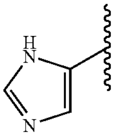 |
| 296 | 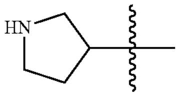 |
| 297 | 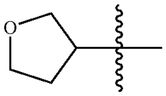 |
| 298 | 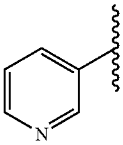 |
| 299 | 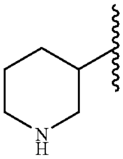 |
| 300 | 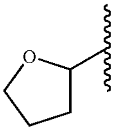 |
| 301 | 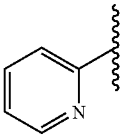 |
| 302 | 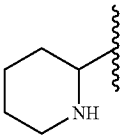 |
| 303 | 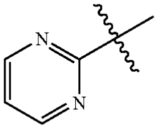 |
-continued
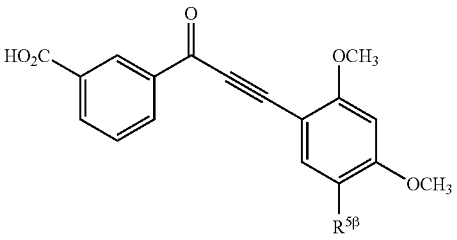
| Ex. No. | $R^{5\beta}$ |
|---|---|
| 304 | 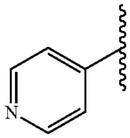 |
| 305 | 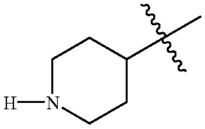 |
| 306 | 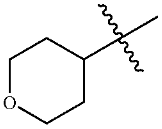 |
| 307 | 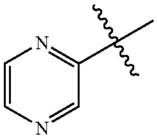 |
| 308 | 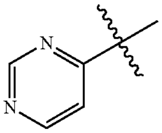 |
| 309 | 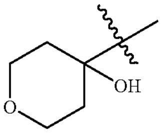 |
| 310 | 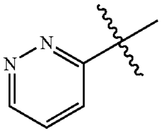 |
| 311 | 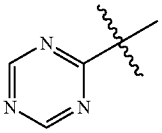 |
| 312 | 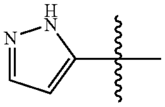 |

-continued
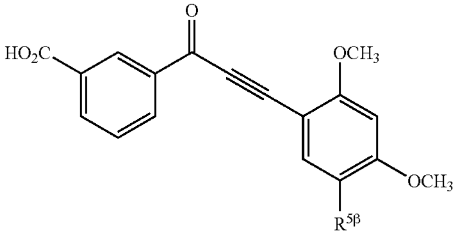
| Ex. No. | $R^{5\beta}$ |
|---|---|
| 313 | 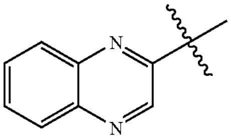 |
| 314 | 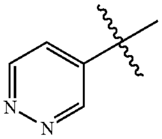 |
| 315 | 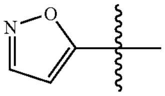 |
| 316 | 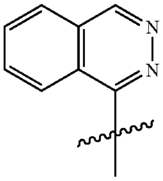 |
| 317 | 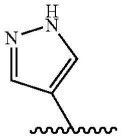 |
| 318 | 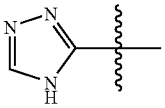 |
| 319 | 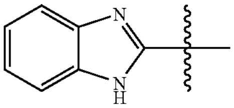 |
| 320 | 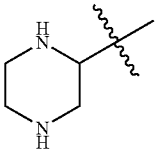 |
| 321 | 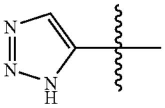 |
-continued
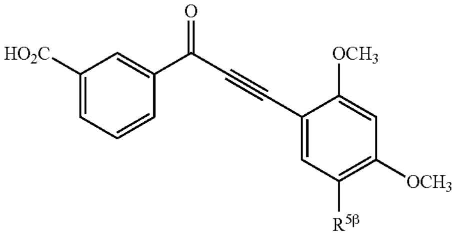
| Ex. No. | $R^{5\beta}$ |
|---|---|
| 322 | 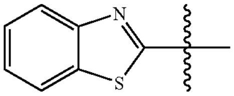 |
| 323 | 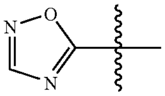 |
| 324 | 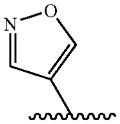 |
| 325 | 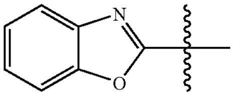 |
| 326 | 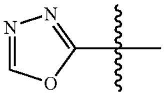 |
| 327 | 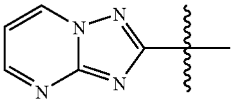 |
| 328 | 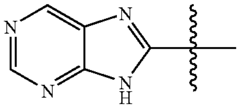 |
| 329 | 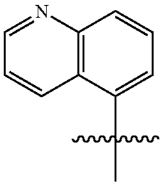 |
| 330 | 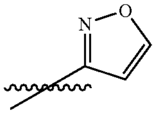 |

-continued
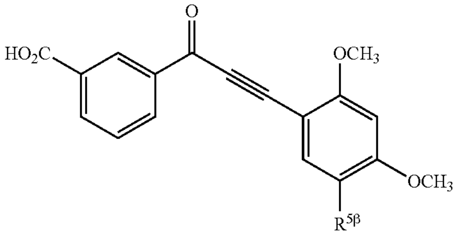
| Ex. No. | $R^{5\beta}$ |
|---|---|
| 331 | 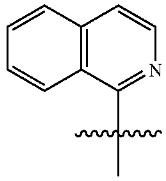 |
| 332 | 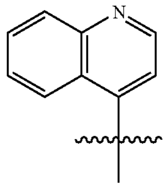 |
| 333 | 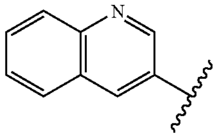 |
| 334 | 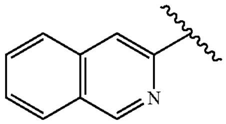 |
| 335 | 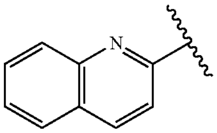 |
| 336 | 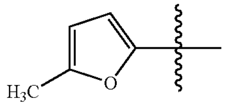 |
| 337 | 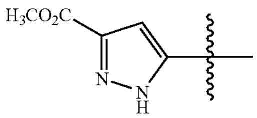 |
-continued
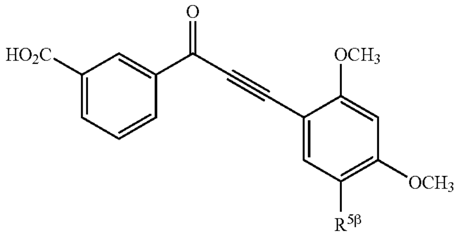
| Ex. No. | $R^{5\beta}$ |
|---|---|
| 338 | 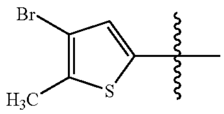 |
| 339 | 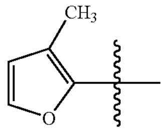 |
| 340 | 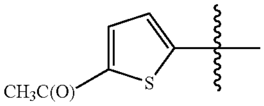 |
| 341 | 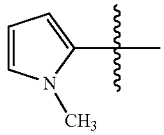 |
| 342 | 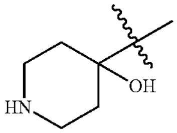 |
| 343 | 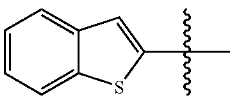 |
| 344 | 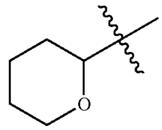 |

Example Table 3
Substituted 2-[3-{(5-Heteroaryl or 5-heterocyclic)-2,4-dimethoxyphenyl}-propynoyl]-benzoic Acids
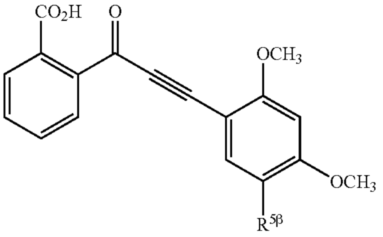
| Ex. No. | $R^{5\beta}$ |
|---|---|
| 345 | 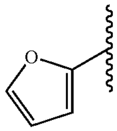 |
| 346 | 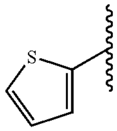 |
| 347 | 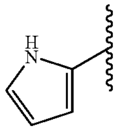 |
| 348 | 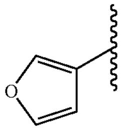 |
| 349 | 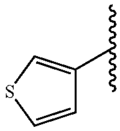 |
| 350 | 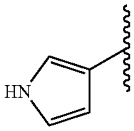 |
| 351 | 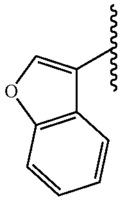 |
-continued
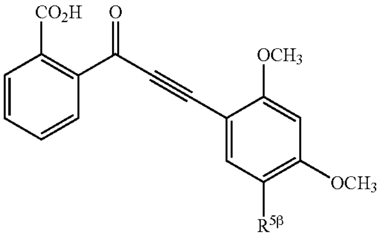
| Ex. No. | $R^{5\beta}$ |
|---|---|
| 352 | 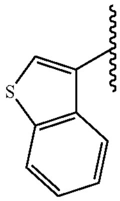 |
| 353 | 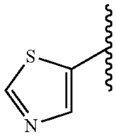 |
| 354 | 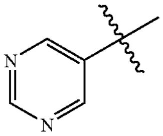 |
| 355 | 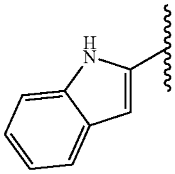 |
| 356 | 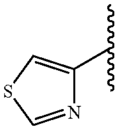 |
| 357 | 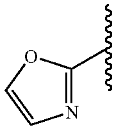 |
| 358 | 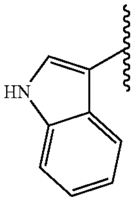 |

-continued
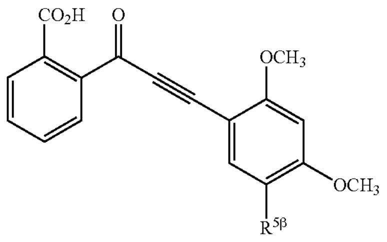
| Ex. No. | $R^{5\beta}$ |
|---|---|
| 359 | 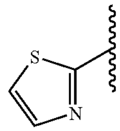 |
| 360 | 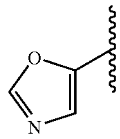 |
| 361 | 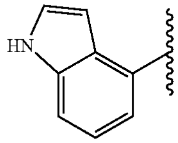 |
| 362 | 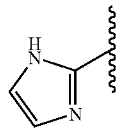 |
| 363 | 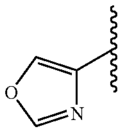 |
| 364 | 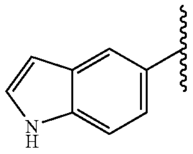 |
| 365 | 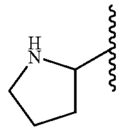 |
| 366 | 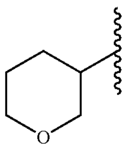 |
-continued
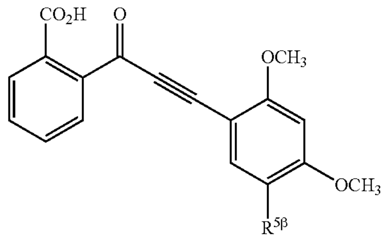
| Ex. No. | $R^{5\beta}$ |
|---|---|
| 367 | 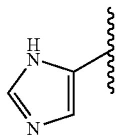 |
| 368 | 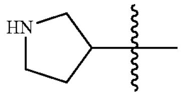 |
| 369 | 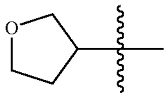 |
| 370 | 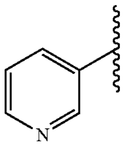 |
| 371 | 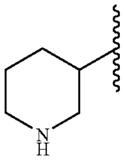 |
| 372 | 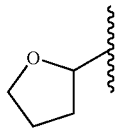 |
| 373 | 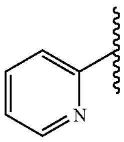 |
| 374 | 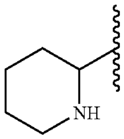 |
| 375 | 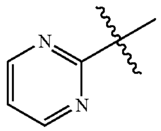 |

-continued
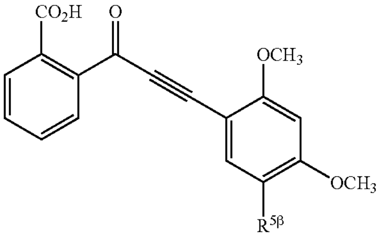
| Ex. No. | $R^{5\beta}$ |
| --- | --- |
| 376 | 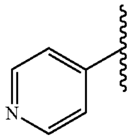 |
| 377 | 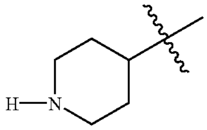 |
| 378 | 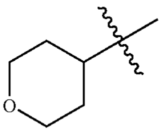 |
| 379 | 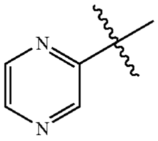 |
| 380 | 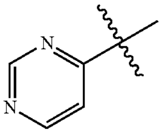 |
| 381 | 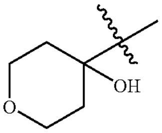 |
| 382 | 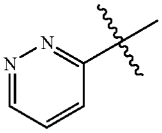 |
| 383 | 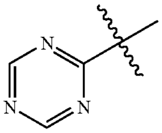 |
| 384 | 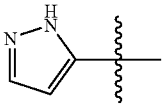 |
-continued
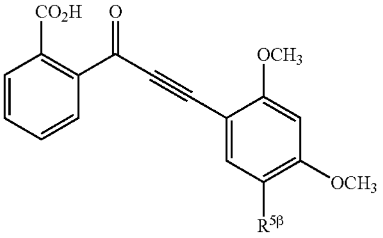
| Ex. No. | $R^{5\beta}$ |
| --- | --- |
| 385 | 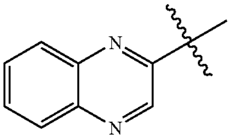 |
| 386 | 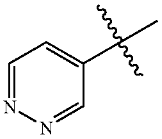 |
| 387 | 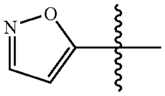 |
| 388 | 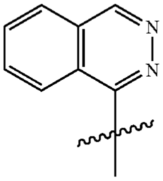 |
| 389 | 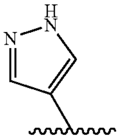 |
| 390 | 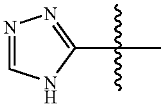 |
| 391 | 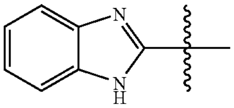 |
| 392 | 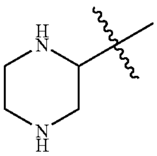 |
| 393 | 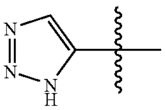 |

-continued
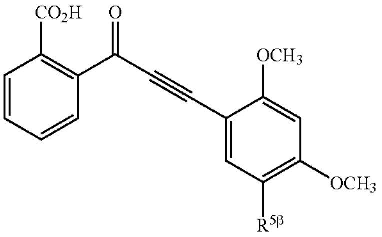
| Ex. No. | $R^{5\beta}$ |
| --- | --- |
| 394 | 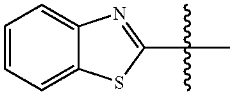 |
| 395 | 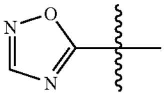 |
| 396 | 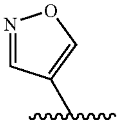 |
| 397 | 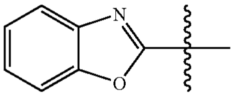 |
| 398 | 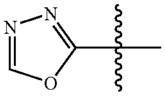 |
| 399 | 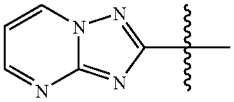 |
| 400 | 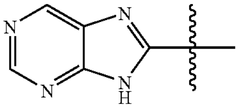 |
| 401 | 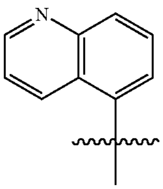 |
| 402 | 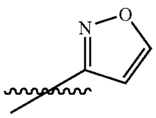 |
-continued
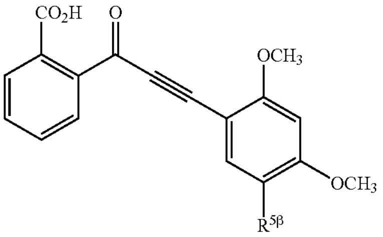
| Ex. No. | $R^{5\beta}$ |
| --- | --- |
| 403 | 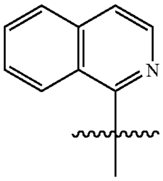 |
| 404 | 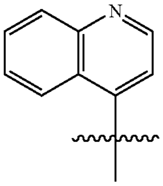 |
| 405 | 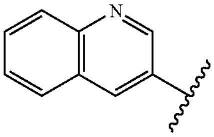 |
| 406 | 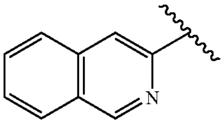 |
| 407 | 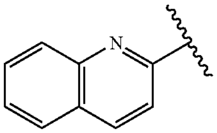 |
| 408 | 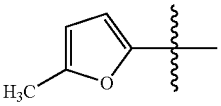 |
| 409 | 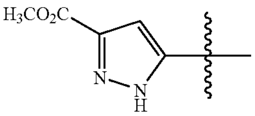 |
| 410 | 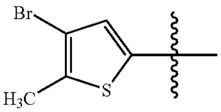 |

-continued
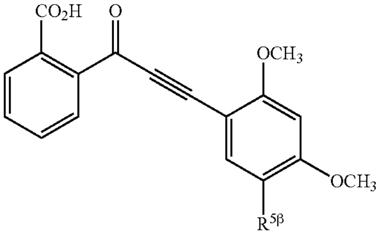
| Ex. No. | $R^{5\beta}$ |
|---|---|
| 411 | 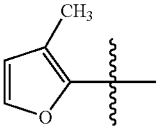 |
| 412 | 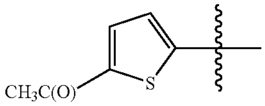 |
| 413 | 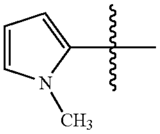 |
| 414 | 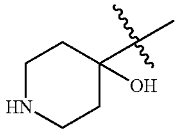 |
| 415 | 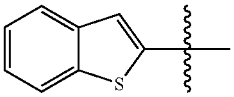 |
| 416 | 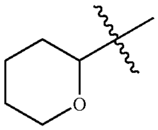 |
Example Table 4
Substituted 4-[3-{(5-Heteroaryl or 5-heterocyclic)-3,4-dimethoxyphenyl}-propynoyl]-benzoic Acids
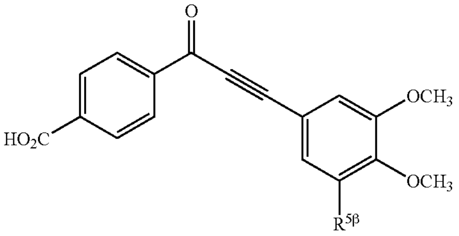
| Ex. No. | $R^{5\beta}$ |
|---|---|
| 417 | 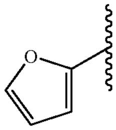 |
| 418 | 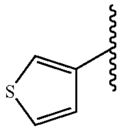 |
| 419 | 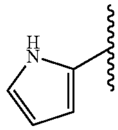 |
| 420 | 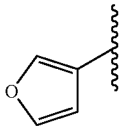 |
| 421 | 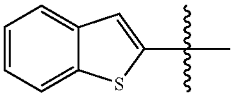 |
| 422 | 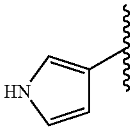 |
| 423 | 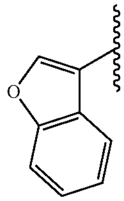 |

-continued
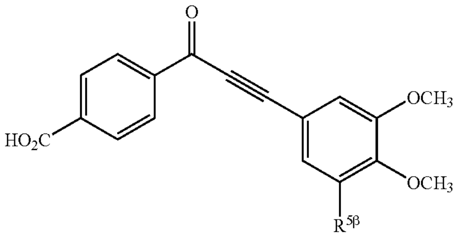
| Ex. No. | $R^{5\beta}$ |
| --- | --- |
| 424 | 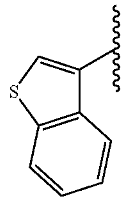 |
| 425 | 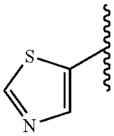 |
| 426 | 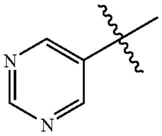 |
| 427 | 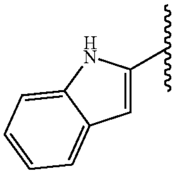 |
| 428 | 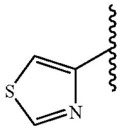 |
| 429 | 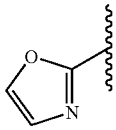 |
| 430 | 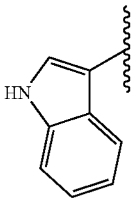 |
-continued
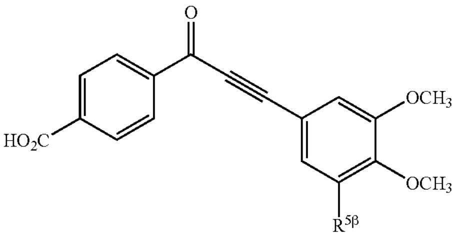
| Ex. No. | $R^{5\beta}$ |
| --- | --- |
| 431 | 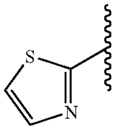 |
| 432 | 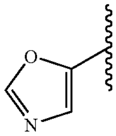 |
| 433 | 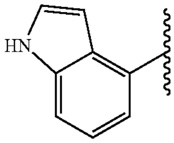 |
| 434 | 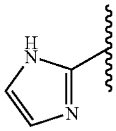 |
| 435 | 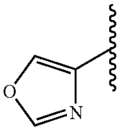 |
| 436 | 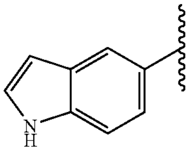 |
| 437 | 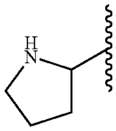 |
| 438 | 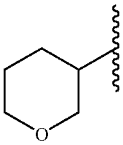 |

-continued
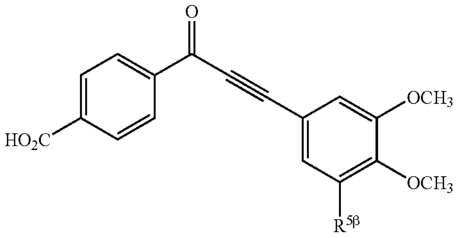
| Ex. No. | $R^{5\beta}$ |
|---|---|
| 439 | 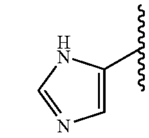 |
| 440 | 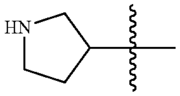 |
| 441 | 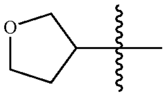 |
| 442 | 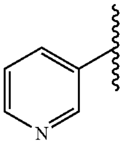 |
| 443 | 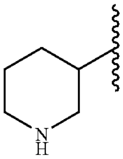 |
| 444 | 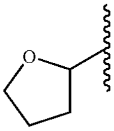 |
| 445 | 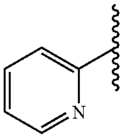 |
| 446 | 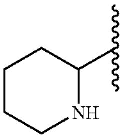 |
| 447 | 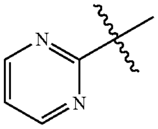 |
-continued
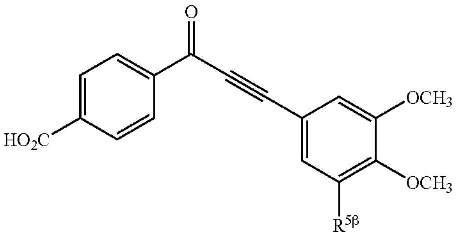
| Ex. No. | $R^{5\beta}$ |
|---|---|
| 448 | 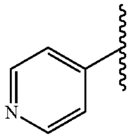 |
| 449 | 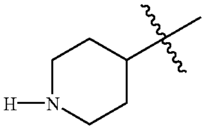 |
| 450 | 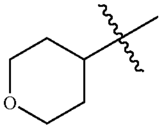 |
| 451 | 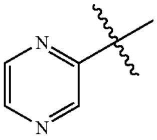 |
| 452 | 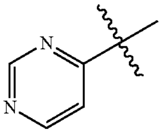 |
| 453 | 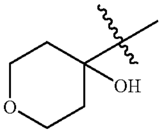 |
| 454 | 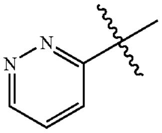 |
| 455 | 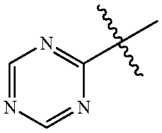 |
| 456 | 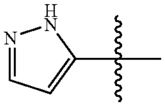 |

-continued
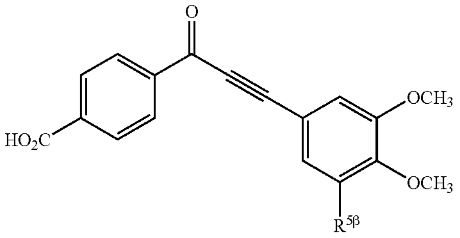
| Ex. No. | $R^{5\beta}$ |
|---|---|
| 457 | 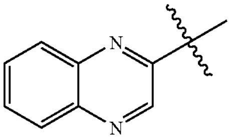 |
| 458 | 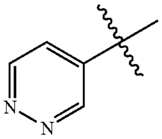 |
| 459 | 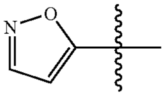 |
| 460 | 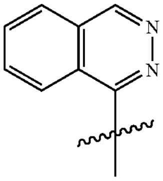 |
| 461 | 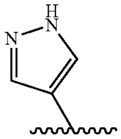 |
| 462 | 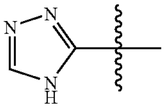 |
| 463 | 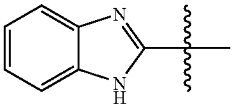 |
| 464 | 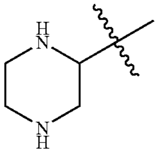 |
| 465 | 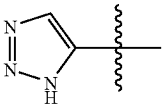 |
-continued
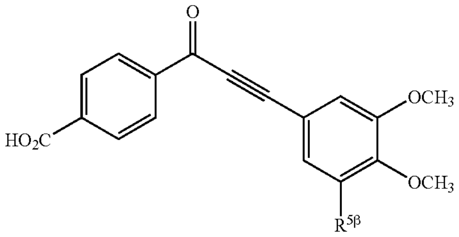
| Ex. No. | $R^{5\beta}$ |
|---|---|
| 466 | 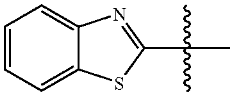 |
| 467 | 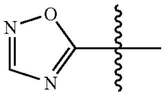 |
| 468 | 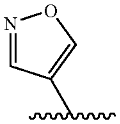 |
| 469 | 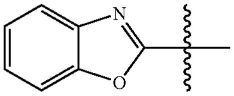 |
| 470 | 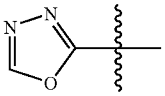 |
| 471 | 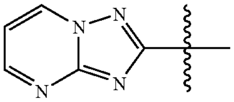 |
| 472 | 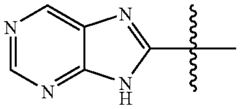 |
| 473 | 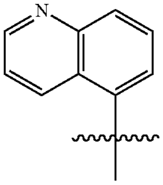 |
| 474 | 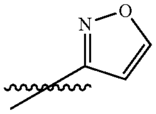 |

-continued
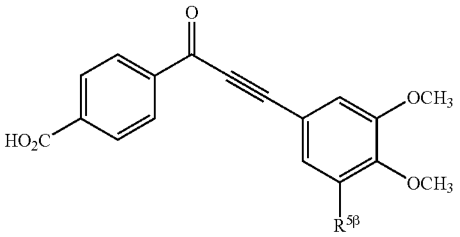
| Ex. No. | $R^{5\beta}$ |
|---|---|
| 475 | 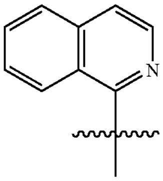 |
| 476 | 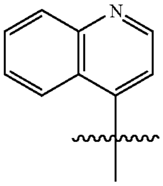 |
| 477 | 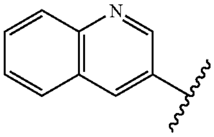 |
| 478 | 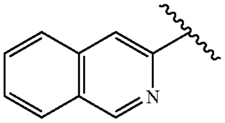 |
| 479 | 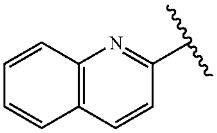 |
| 480 | 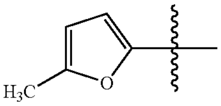 |
| 481 | 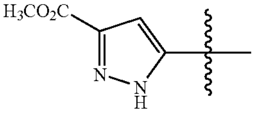 |
| 482 | 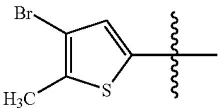 |
-continued
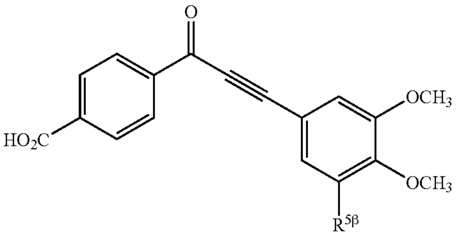
| Ex. No. | $R^{5\beta}$ |
|---|---|
| 483 | 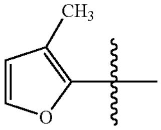 |
| 484 | 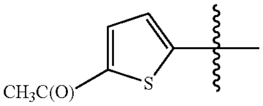 |
| 485 | 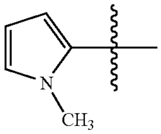 |
| 486 | 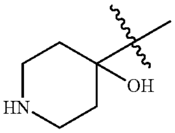 |
| 487 | 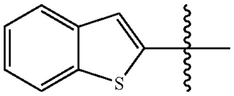 |
| 488 | 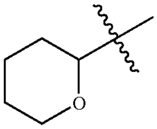 |
| 489 | 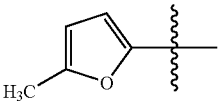 |
| 490 | 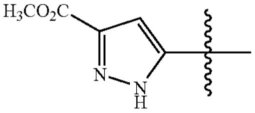 |
| 491 | 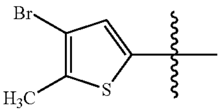 |

-continued
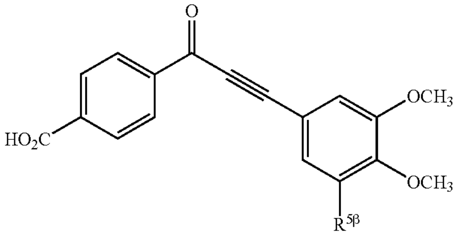
| Ex. No. | $R^{5\beta}$ |
|---|---|
| 492 | 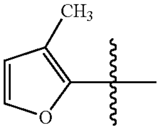 |
| 493 | 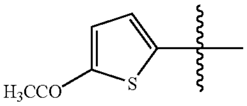 |
| 494 | 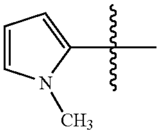 |
| 495 | 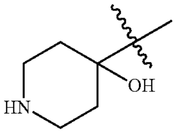 |
| 496 | 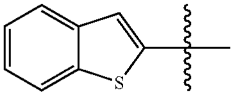 |
| 497 | 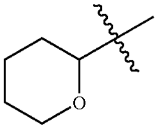 |
Example Table 5
Substituted 3-[3-{(5-Heteroaryl or 5-heterocyclic)-3,4-dimethoxyphenyl}-propynoyl]-benzoic Acids
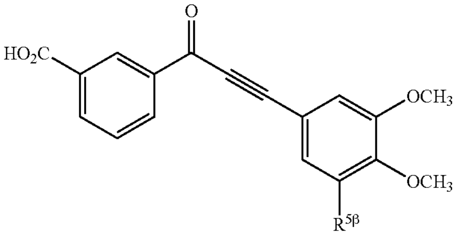
| Ex. No. | $R^{5\beta}$ |
|---|---|
| 498 | 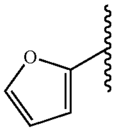 |
| 499 | 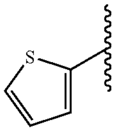 |
| 500 | 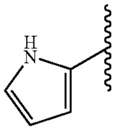 |
| 501 | 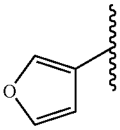 |
| 502 | 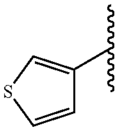 |
| 503 | 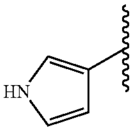 |
| 504 | 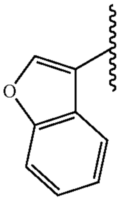 |

-continued
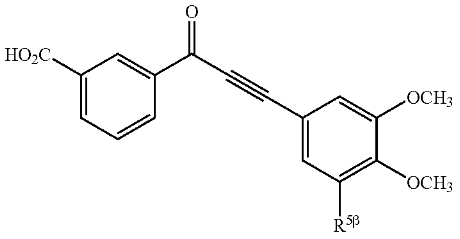
| Ex. No. | $R^{5\beta}$ |
|---|---|
| 505 | 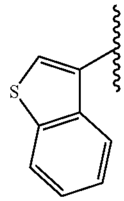 |
| 506 | 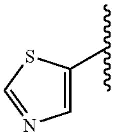 |
| 507 | 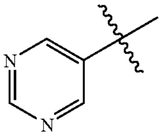 |
| 508 | 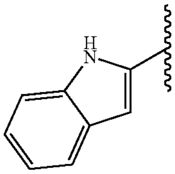 |
| 509 | 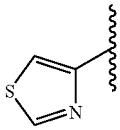 |
| 510 | 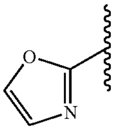 |
| 511 | 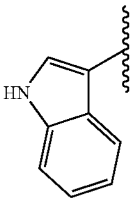 |
-continued
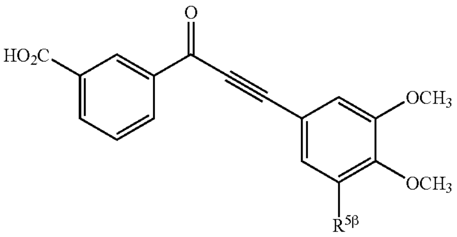
| Ex. No. | $R^{5\beta}$ |
|---|---|
| 512 | 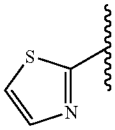 |
| 513 | 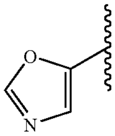 |
| 514 | 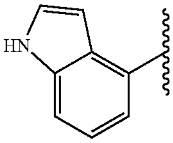 |
| 515 | 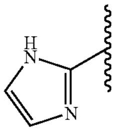 |
| 516 | 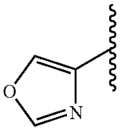 |
| 517 | 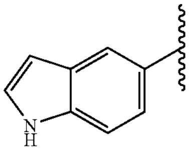 |
| 518 | 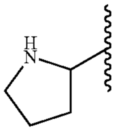 |
| 519 | 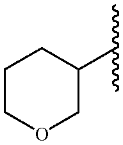 |

-continued
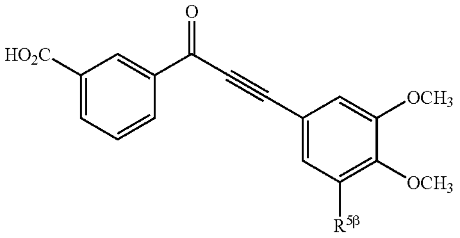
| Ex. No. | $R^{5\beta}$ |
|---|---|
| 520 | 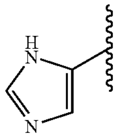 |
| 521 | 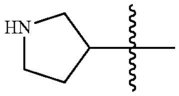 |
| 522 | 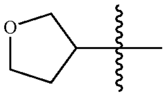 |
| 523 | 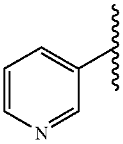 |
| 524 | 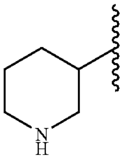 |
| 525 | 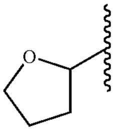 |
| 526 | 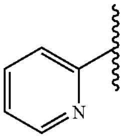 |
| 527 | 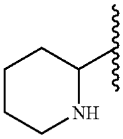 |
| 528 | 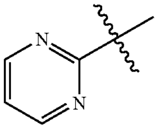 |
-continued
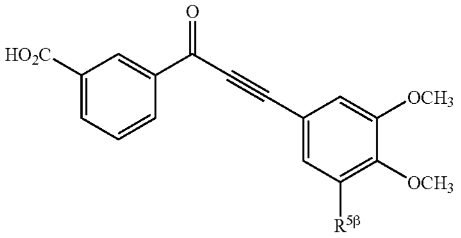
| Ex. No. | $R^{5\beta}$ |
|---|---|
| 529 | 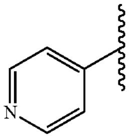 |
| 530 | 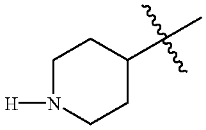 |
| 531 | 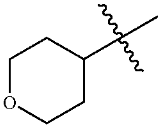 |
| 532 | 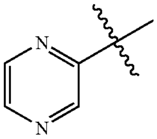 |
| 533 | 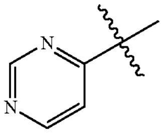 |
| 534 | 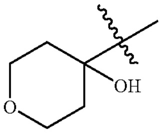 |
| 535 | 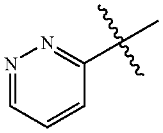 |
| 536 | 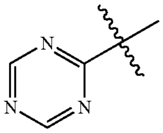 |
| 537 | 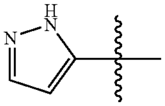 |

-continued
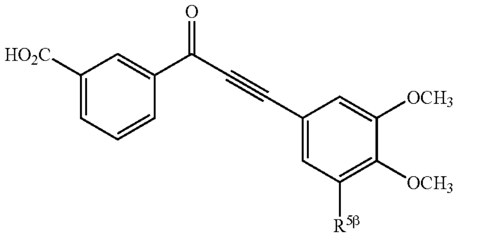
| Ex. No. | $R^{5\beta}$ |
| --- | --- |
| 538 | 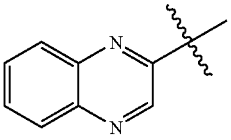 |
| 539 | 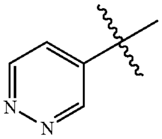 |
| 540 | 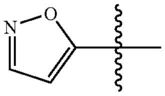 |
| 541 | 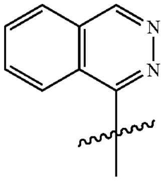 |
| 542 | 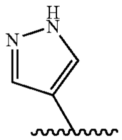 |
| 543 | 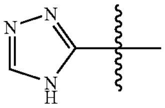 |
| 544 | 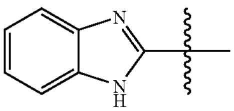 |
| 545 | 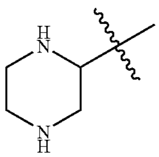 |
| 546 | 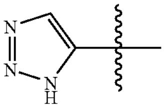 |
-continued
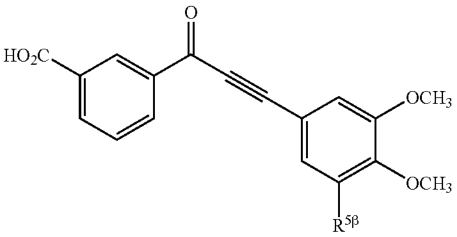
| Ex. No. | $R^{5\beta}$ |
| --- | --- |
| 547 | 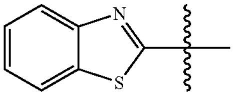 |
| 548 | 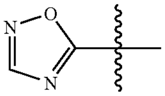 |
| 549 | 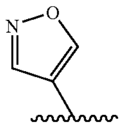 |
| 550 | 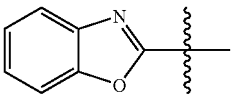 |
| 551 | 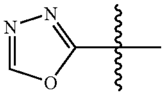 |
| 552 | 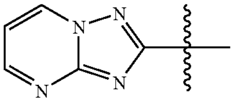 |
| 553 | 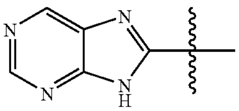 |
| 554 | 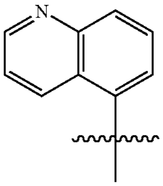 |
| 555 | 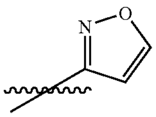 |

-continued
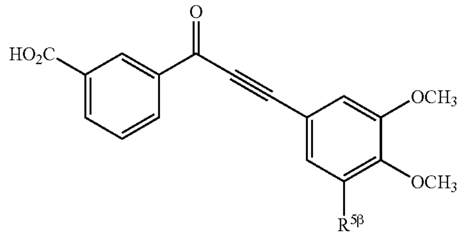
| Ex. No. | $R^{5\beta}$ |
|---|---|
| 556 | 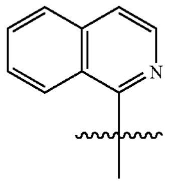 |
| 557 | 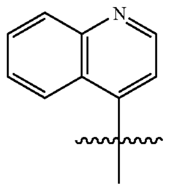 |
| 558 | 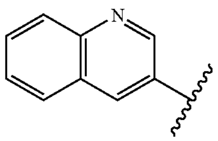 |
| 559 | 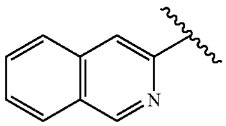 |
| 560 | 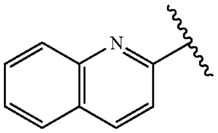 |
| 561 | 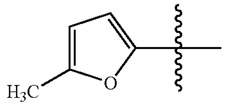 |
| 562 | 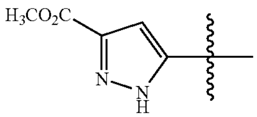 |
-continued
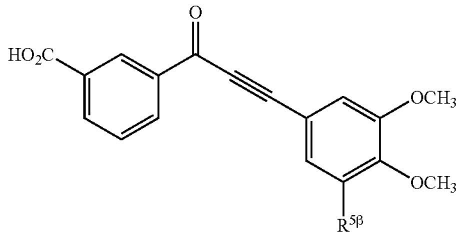
| Ex. No. | $R^{5\beta}$ |
|---|---|
| 563 | 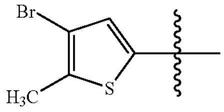 |
| 564 | 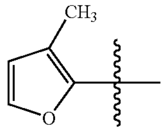 |
| 565 | 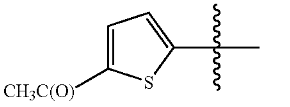 |
| 566 | 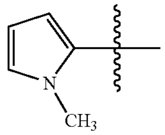 |
| 567 | 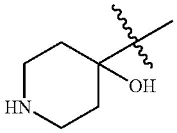 |
| 568 | 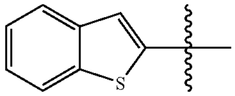 |
| 569 | 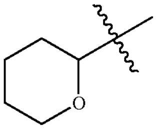 |

Example Table 6
Substituted 2-[3-{(5-Heteroaryl or 5-heterocyclic)-3,4-dimethoxyphenyl}-propynoyl]-benzoic Acids
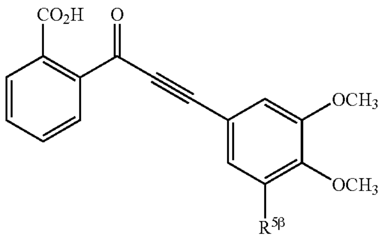
| Ex. No. | $R^{5\beta}$ |
|---|---|
| 570 | 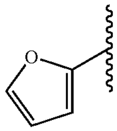 |
| 571 | 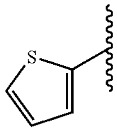 |
| 572 | 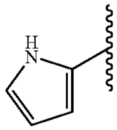 |
| 573 | 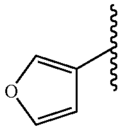 |
| 574 | 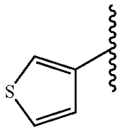 |
| 575 | 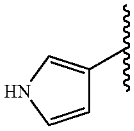 |
| 576 | 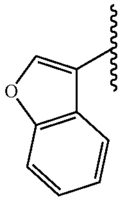 |
-continued
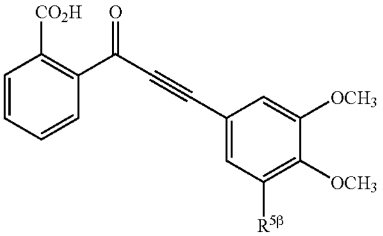
| Ex. No. | $R^{5\beta}$ |
|---|---|
| 577 | 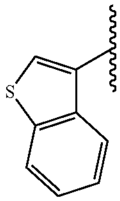 |
| 578 | 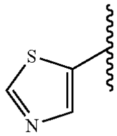 |
| 579 | 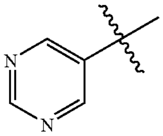 |
| 580 | 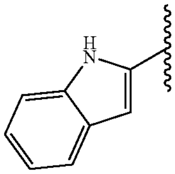 |
| 581 | 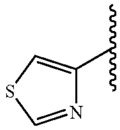 |
| 582 | 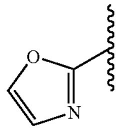 |
| 583 | 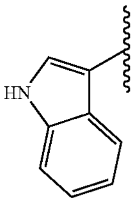 |

-continued
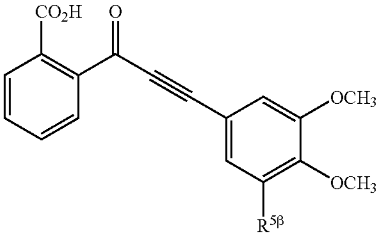
| Ex. No. | $R^{5\beta}$ |
|---|---|
| 584 | 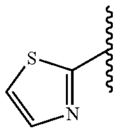 |
| 585 | 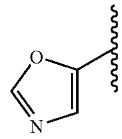 |
| 586 | 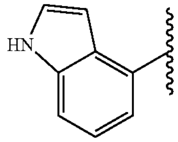 |
| 587 | 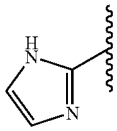 |
| 588 | 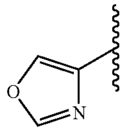 |
| 589 | 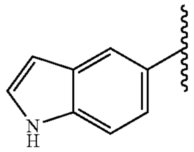 |
| 590 | 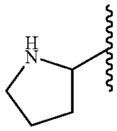 |
| 591 | 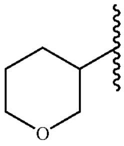 |
-continued
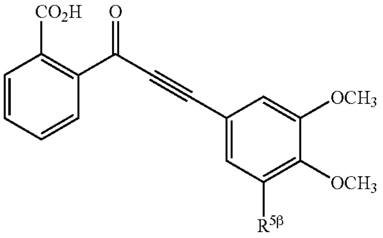
| Ex. No. | $R^{5\beta}$ |
|---|---|
| 592 | 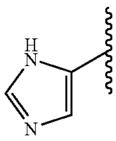 |
| 593 | 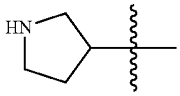 |
| 594 | 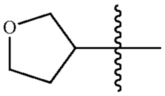 |
| 595 | 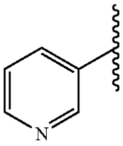 |
| 596 | 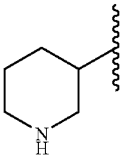 |
| 597 | 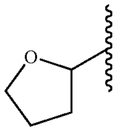 |
| 598 | 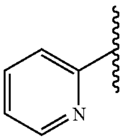 |
| 599 | 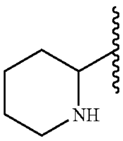 |
| 600 | 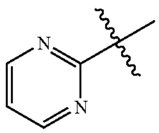 |

-continued
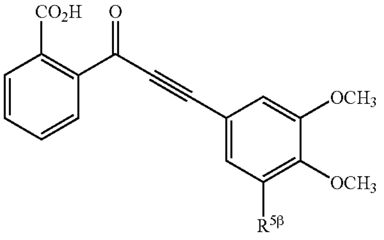
| Ex. No. | $R^{5\beta}$ |
| --- | --- |
| 601 | 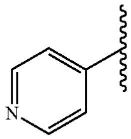 |
| 602 | 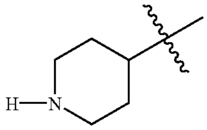 |
| 603 | 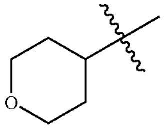 |
| 604 | 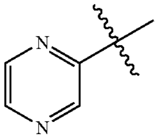 |
| 605 | 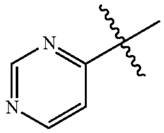 |
| 606 | 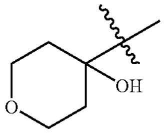 |
| 607 | 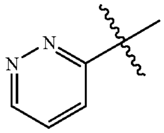 |
| 608 | 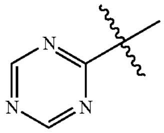 |
| 609 | 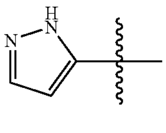 |
-continued
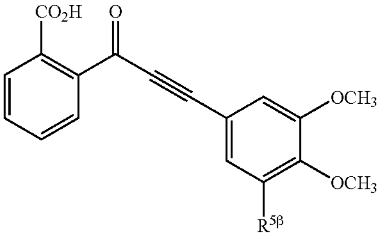
| Ex. No. | $R^{5\beta}$ |
| --- | --- |
| 610 | 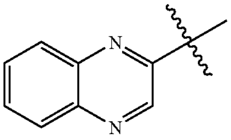 |
| 611 | 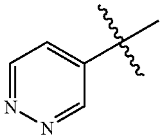 |
| 612 | 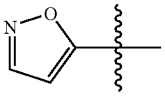 |
| 613 | 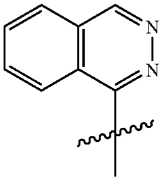 |
| 614 | 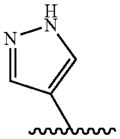 |
| 615 | 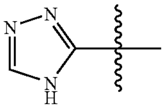 |
| 616 | 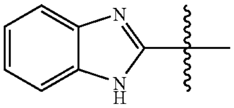 |
| 617 | 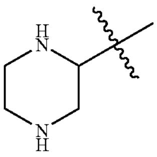 |
| 618 | 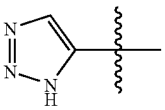 |

-continued
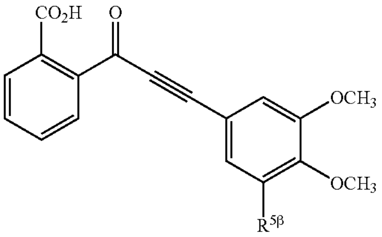
| Ex. No. | $R^{5\beta}$ |
|---|---|
| 619 | 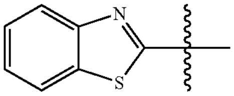 |
| 620 | 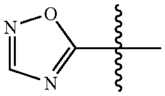 |
| 621 | 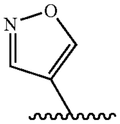 |
| 622 | 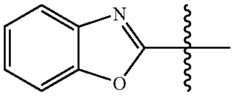 |
| 623 | 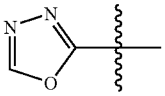 |
| 624 | 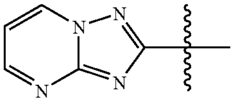 |
| 625 | 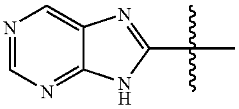 |
| 626 | 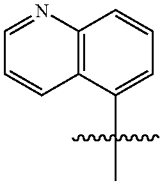 |
| 627 | 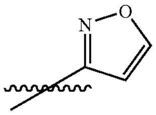 |
-continued
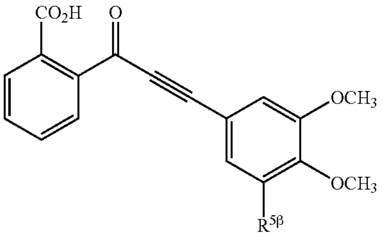
| Ex. No. | $R^{5\beta}$ |
|---|---|
| 628 | 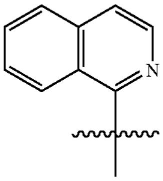 |
| 629 | 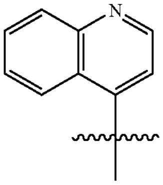 |
| 630 | 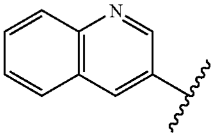 |
| 631 | 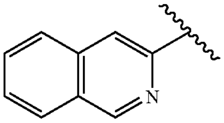 |
| 632 | 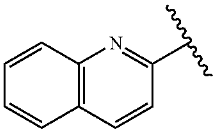 |
| 633 | 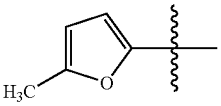 |
| 634 | 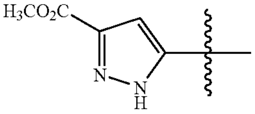 |
| 635 | 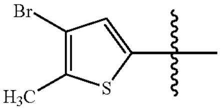 |

-continued
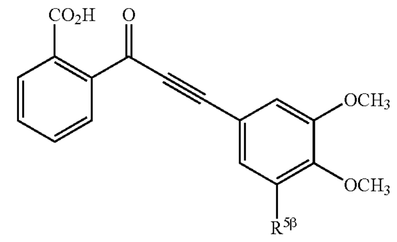
| Ex. No. | $R^{5\beta}$ |
|---|---|
| 636 | 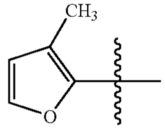 |
| 637 | 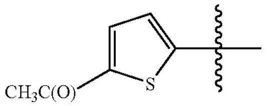 |
| 638 | 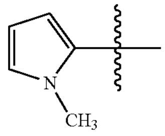 |
| 639 | 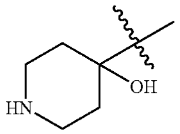 |
| 640 | 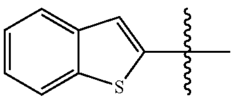 |
| 641 | 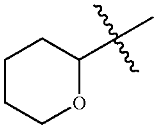 |
Example Table 7
Substituted 4-[3-{(4-Heteroaryl or 4-heterocyclic)-2,6-dimethoxyphenyl}-propynoyl]-benzoic Acids
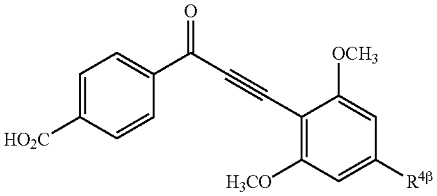
| Ex. No. | $R^{4\beta}$ |
|---|---|
| 642 | 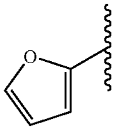 |
| 643 | 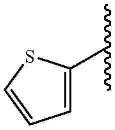 |
| 644 | 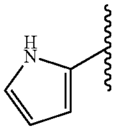 |
| 645 | 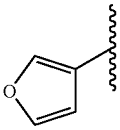 |
| 646 | 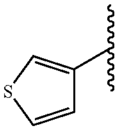 |
| 647 | 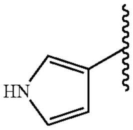 |
| 648 | 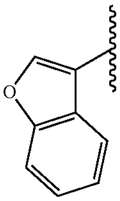 |

-continued
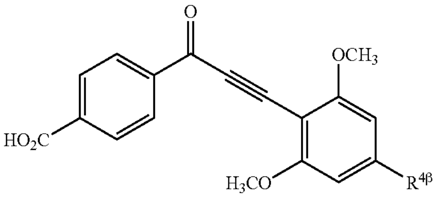
| Ex. No. | $R^{4\beta}$ |
|---|---|
| 649 | 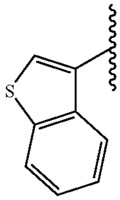 |
| 650 | 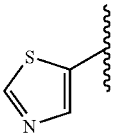 |
| 651 | 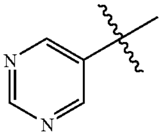 |
| 652 | 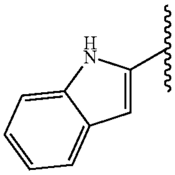 |
| 653 | 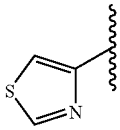 |
| 654 | 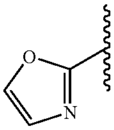 |
| 655 | 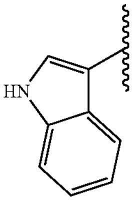 |
| 656 | 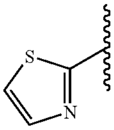 |
-continued
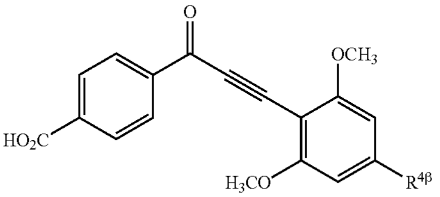
| Ex. No. | $R^{4\beta}$ |
|---|---|
| 657 | 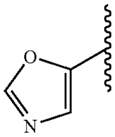 |
| 658 | 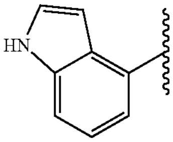 |
| 659 | 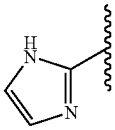 |
| 660 | 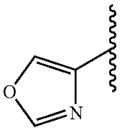 |
| 661 | 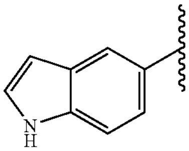 |
| 662 | 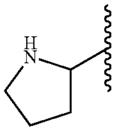 |
| 663 | 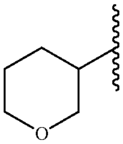 |
| 664 | 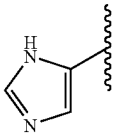 |
| 665 | 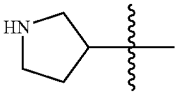 |

-continued
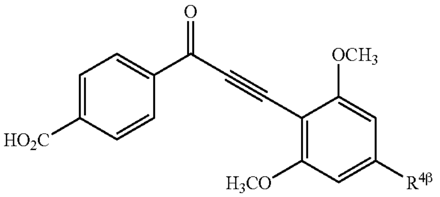
| Ex. No. | $R^{4\beta}$ |
|---|---|
| 666 | 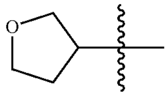 |
| 667 | 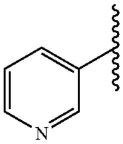 |
| 668 | 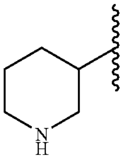 |
| 669 | 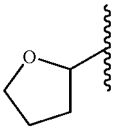 |
| 670 | 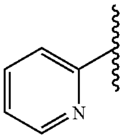 |
| 671 | 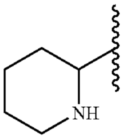 |
| 672 | 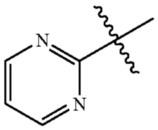 |
| 673 | 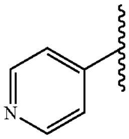 |
| 674 | 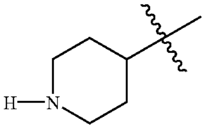 |
-continued
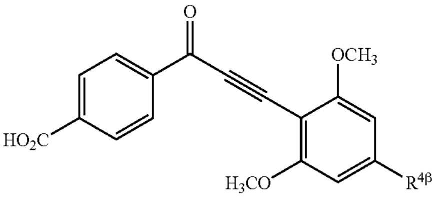
| Ex. No. | $R^{4\beta}$ |
|---|---|
| 675 | 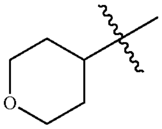 |
| 676 | 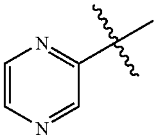 |
| 677 | 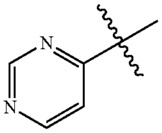 |
| 678 | 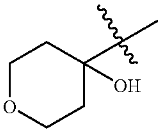 |
| 679 | 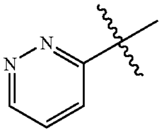 |
| 680 | 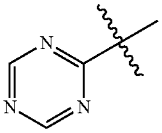 |
| 681 | 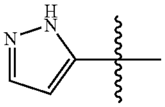 |
| 682 | 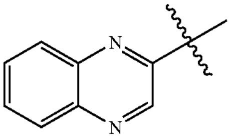 |
| 683 | 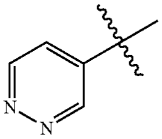 |

-continued
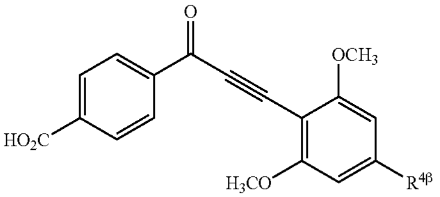
| Ex. No. | $R^{4\beta}$ |
|---|---|
| 684 | 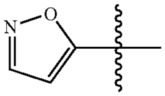 |
| 685 | 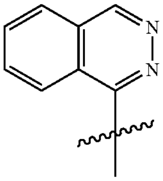 |
| 686 | 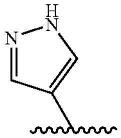 |
| 687 | 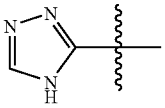 |
| 688 | 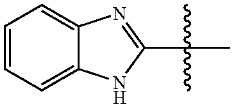 |
| 689 | 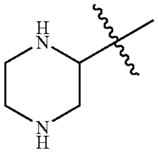 |
| 690 | 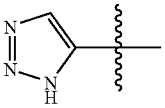 |
| 691 | 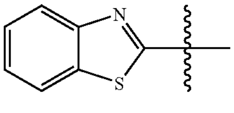 |
| 692 | 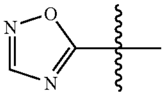 |
| 693 | 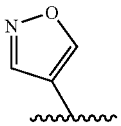 |
-continued
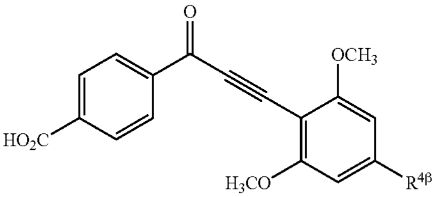
| Ex. No. | $R^{4\beta}$ |
|---|---|
| 694 | 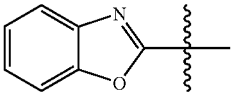 |
| 695 | 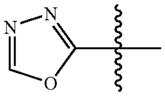 |
| 696 | 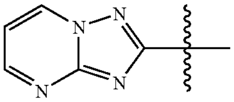 |
| 697 | 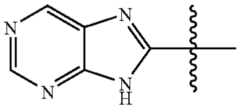 |
| 698 | 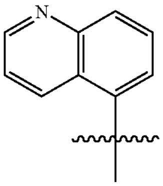 |
| 699 | 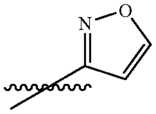 |
| 700 | 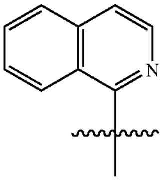 |
| 701 | 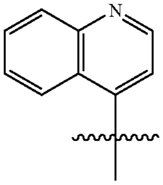 |
| 702 | 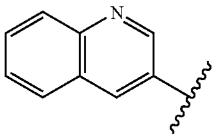 |

-continued
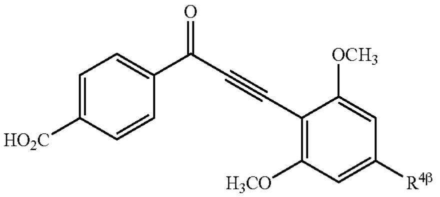
| Ex. No. | $R^{4\beta}$ |
|---|---|
| 703 | 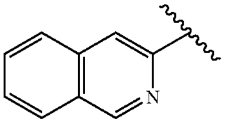 |
| 704 | 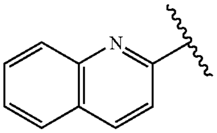 |
| 705 | 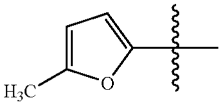 |
| 706 | 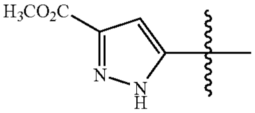 |
| 707 | 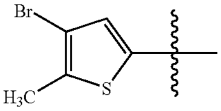 |
| 708 | 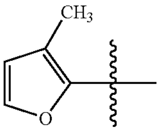 |
| 709 | 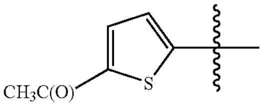 |
| 710 | 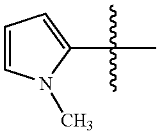 |
| 711 | 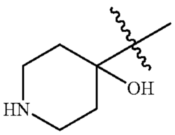 |
| 712 | 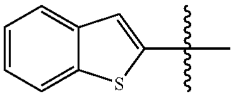 |
-continued
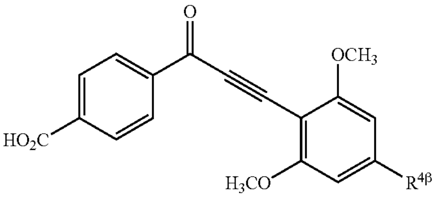
| Ex. No. | $R^{4\beta}$ |
|---|---|
| 713 | 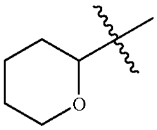 |
Example Table 8
Substituted 3-[3-{(4-Heteroaryl or 4-heterocyclic)-2,6-dimethoxyphenyl}-propynoyl]-benzoic Acids
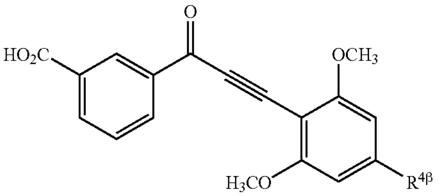
| Ex. No. | $R^{4\beta}$ |
|---|---|
| 714 | 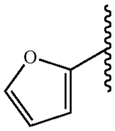 |
| 715 | 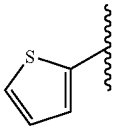 |
| 716 | 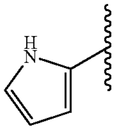 |
| 717 | 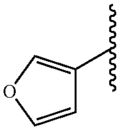 |

-continued
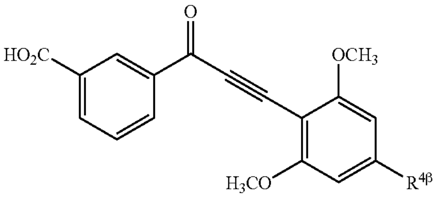
| Ex. No. | $R^{4\beta}$ |
|---|---|
| 718 | 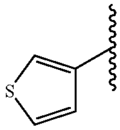 |
| 719 | 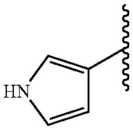 |
| 720 | 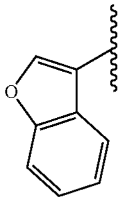 |
| 721 | 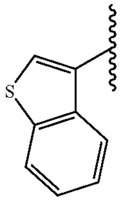 |
| 722 | 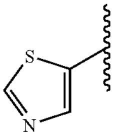 |
| 723 | 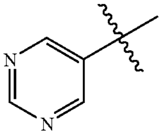 |
| 724 | 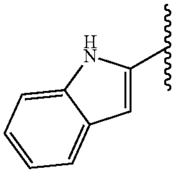 |
| 725 | 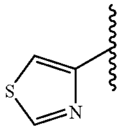 |
-continued
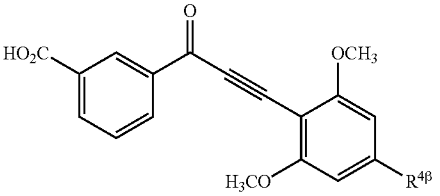
| Ex. No. | $R^{4\beta}$ |
|---|---|
| 726 | 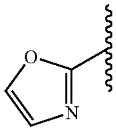 |
| 727 | 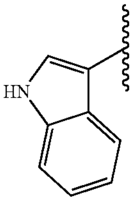 |
| 728 | 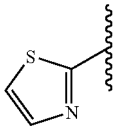 |
| 729 | 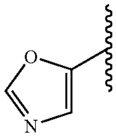 |
| 730 | 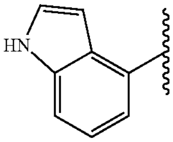 |
| 731 | 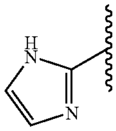 |
| 732 | 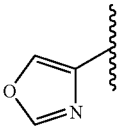 |
| 733 | 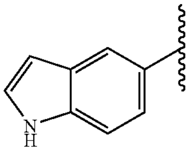 |

-continued
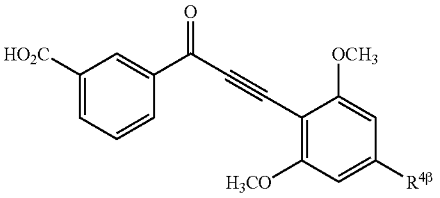
| Ex. No. | $R^{4\beta}$ |
|---|---|
| 734 | 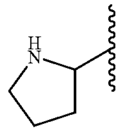 |
| 735 | 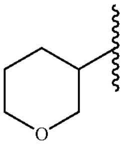 |
| 736 | 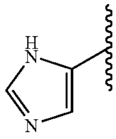 |
| 737 | 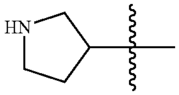 |
| 738 | 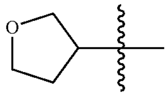 |
| 739 | 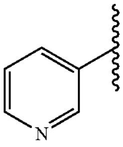 |
| 740 | 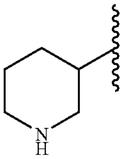 |
| 741 | 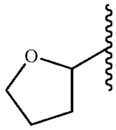 |
| 742 | 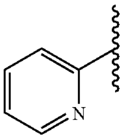 |
-continued
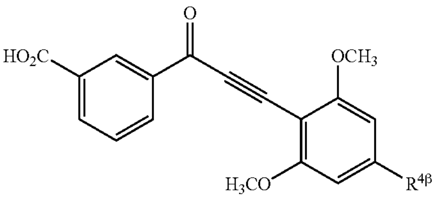
| Ex. No. | $R^{4\beta}$ |
|---|---|
| 743 | 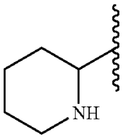 |
| 744 | 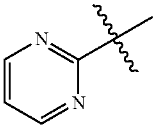 |
| 745 | 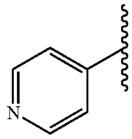 |
| 746 | 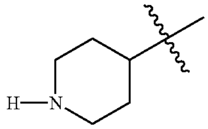 |
| 747 | 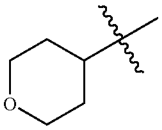 |
| 748 | 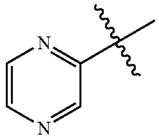 |
| 749 | 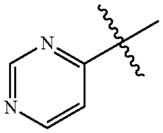 |
| 750 | 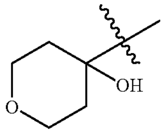 |
| 751 | 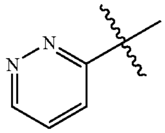 |

-continued
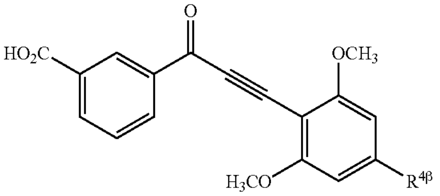
| Ex. No. | $R^{4\beta}$ |
|---|---|
| 752 | 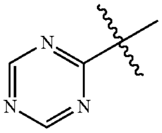 |
| 753 | 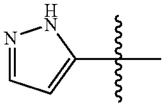 |
| 754 | 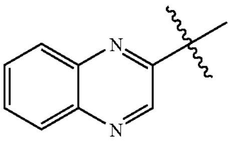 |
| 755 | 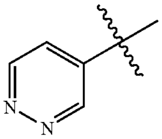 |
| 756 | 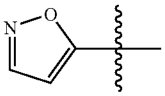 |
| 757 | 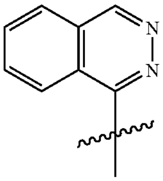 |
| 758 | 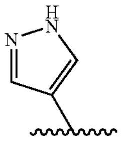 |
| 759 | 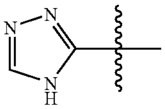 |
| 760 | 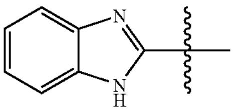 |
-continued
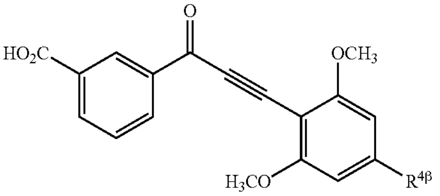
| Ex. No. | $R^{4\beta}$ |
|---|---|
| 761 | 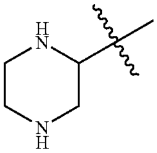 |
| 762 | 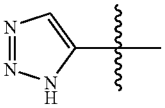 |
| 763 | 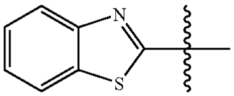 |
| 764 | 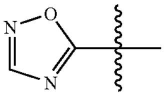 |
| 765 | 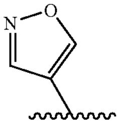 |
| 766 | 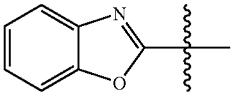 |
| 767 | 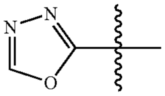 |
| 768 | 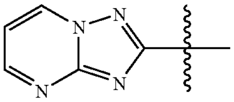 |
| 769 | 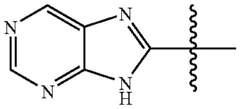 |
| 770 | 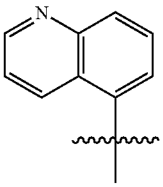 |

-continued
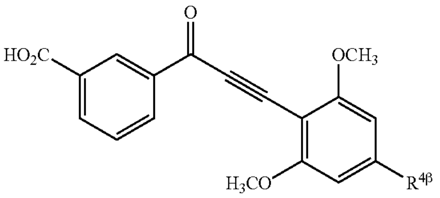
| Ex. No. | $R^{4\beta}$ |
|---|---|
| 771 | 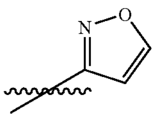 |
| 772 | 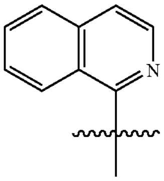 |
| 773 | 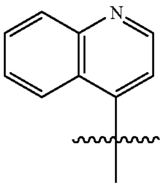 |
| 774 | 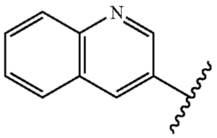 |
| 775 | 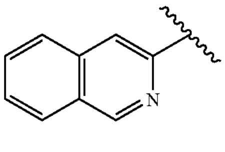 |
| 776 | 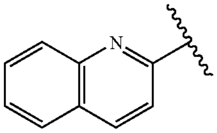 |
| 777 | 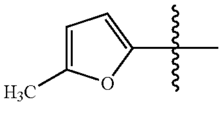 |
-continued
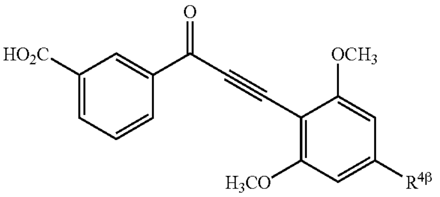
| Ex. No. | $R^{4\beta}$ |
|---|---|
| 778 | 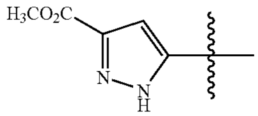 |
| 779 | 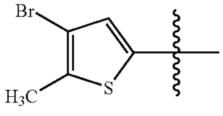 |
| 780 | 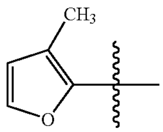 |
| 781 | 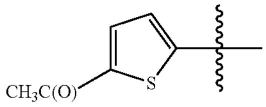 |
| 782 | 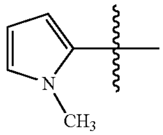 |
| 783 | 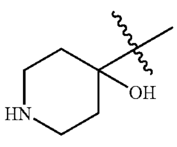 |
| 784 | 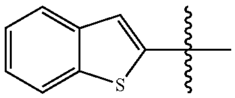 |
| 785 | 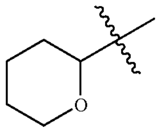 |

Example Table 9
Substituted 2-[3-{(4-Heteroaryl or 4-heterocyclic)-2,6-dimethoxyphenyl}-propynoyl]-benzoic Acids
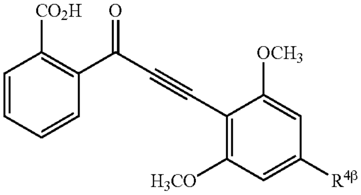
| Ex. No. | $R^{4\beta}$ |
|---|---|
| 786 | 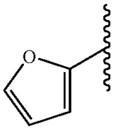 |
| 787 | 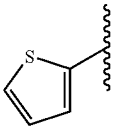 |
| 788 | 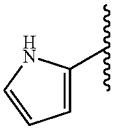 |
| 789 | 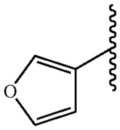 |
| 790 | 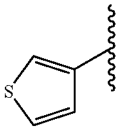 |
| 791 | 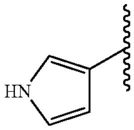 |
| 792 | 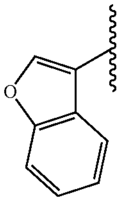 |
-continued
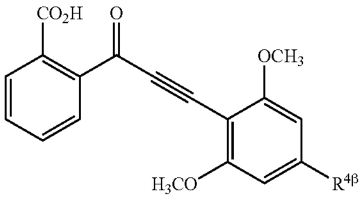
| Ex. No. | $R^{4\beta}$ |
|---|---|
| 793 | 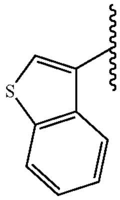 |
| 794 | 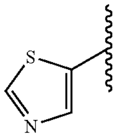 |
| 795 | 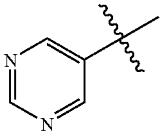 |
| 796 | 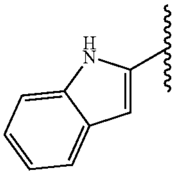 |
| 797 | 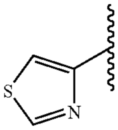 |
| 798 | 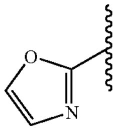 |
| 799 | 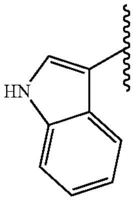 |
| 800 | 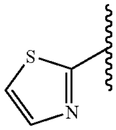 |

-continued
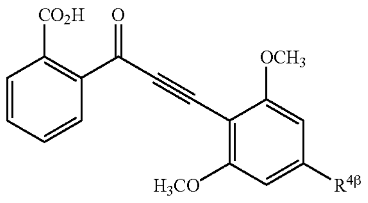
| Ex. No. | $R^{4\beta}$ |
|---|---|
| 801 | 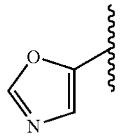 |
| 802 | 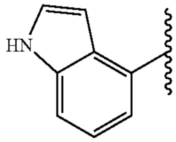 |
| 803 | 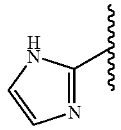 |
| 804 | 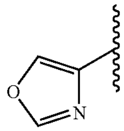 |
| 805 | 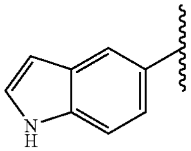 |
| 806 | 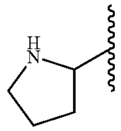 |
| 807 | 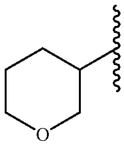 |
| 808 | 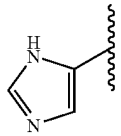 |
| 809 | 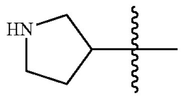 |
-continued
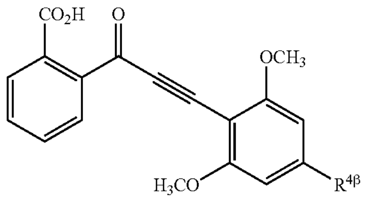
| Ex. No. | $R^{4\beta}$ |
|---|---|
| 810 | 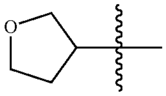 |
| 811 | 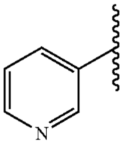 |
| 812 | 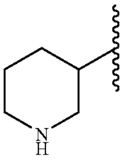 |
| 813 | 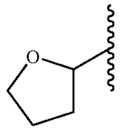 |
| 814 | 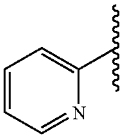 |
| 815 | 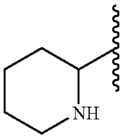 |
| 816 | 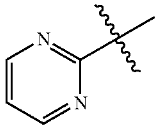 |
| 817 | 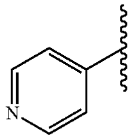 |
| 818 | 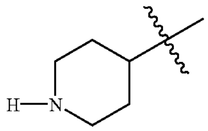 |

-continued
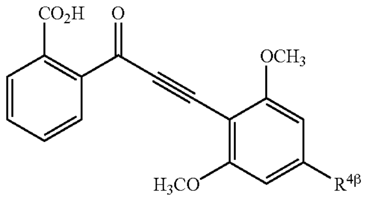
| Ex. No. | $R^{4\beta}$ |
|---|---|
| 819 | 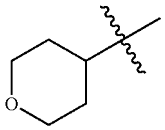 |
| 820 | 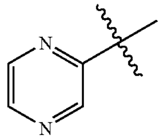 |
| 821 | 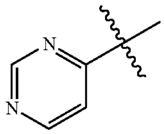 |
| 822 | 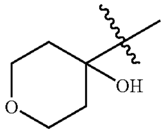 |
| 823 | 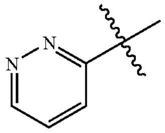 |
| 824 | 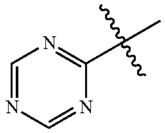 |
| 825 | 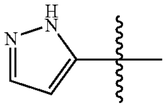 |
| 826 | 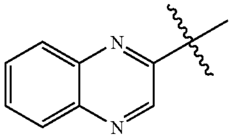 |
| 827 | 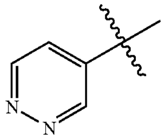 |
-continued
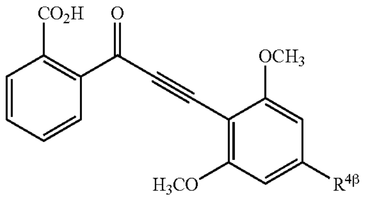
| Ex. No. | $R^{4\beta}$ |
|---|---|
| 828 | 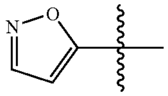 |
| 829 | 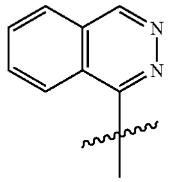 |
| 830 | 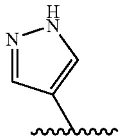 |
| 831 | 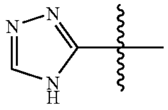 |
| 832 | 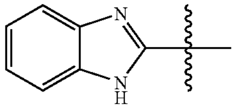 |
| 833 | 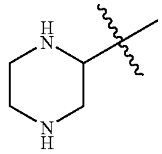 |
| 834 | 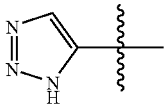 |
| 835 | 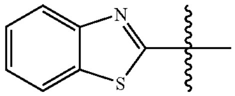 |
| 836 | 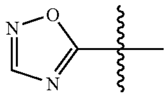 |
| 837 | 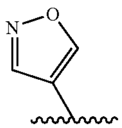 |

-continued
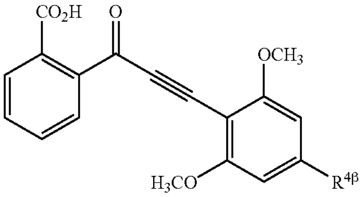
| Ex. No. | $R^{4\beta}$ |
| --- | --- |
| 838 | 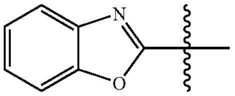 |
| 839 | 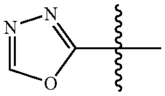 |
| 840 | 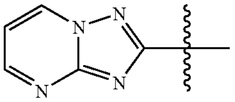 |
| 841 | 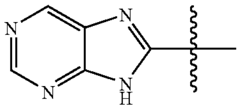 |
| 842 | 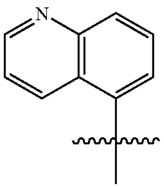 |
| 843 | 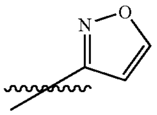 |
| 844 | 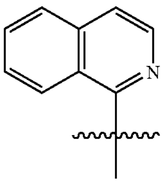 |
| 845 | 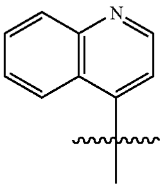 |
| 846 | 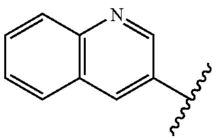 |
-continued
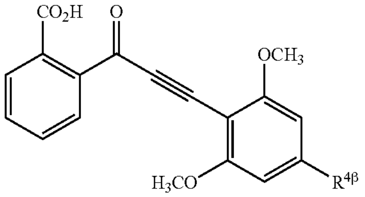
| Ex. No. | $R^{4\beta}$ |
| --- | --- |
| 847 | 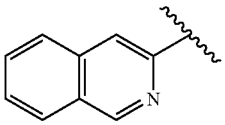 |
| 848 | 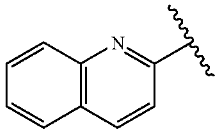 |
| 849 | 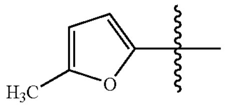 |
| 850 | 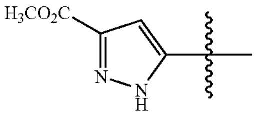 |
| 851 | 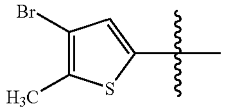 |
| 852 | 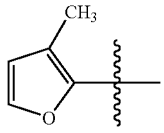 |
| 853 | 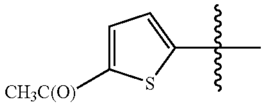 |
| 854 | 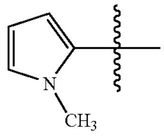 |
| 855 | 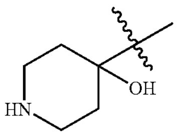 |
| 856 | 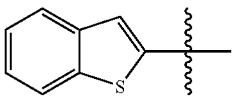 |

-continued

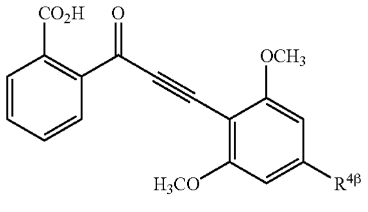

| Ex. No. | $R^{4\beta}$ |
|---|---|
| 857 | 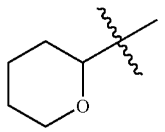 |

Example Table 10

Substituted 4-[3-(5-Thiophen-2-yl-phenyl)-propynoyl]-benzoic Acids

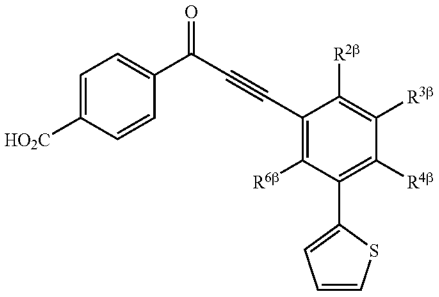

| Ex. No. | $R^{2\beta}$ | $R^{3\beta}$ | $R^{4\beta}$ | $R^{6\beta}$ |
|---|---|---|---|---|
| 858 | F | H | H | H |
| 859 | 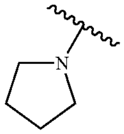 | H | H | H |
| 860 | H | H | F | H |
| 861 | H | H | 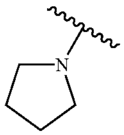 | H |
| 862 | H | H | OMe | H |
| 863 | F | H | 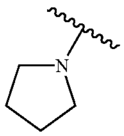 | H |

-continued

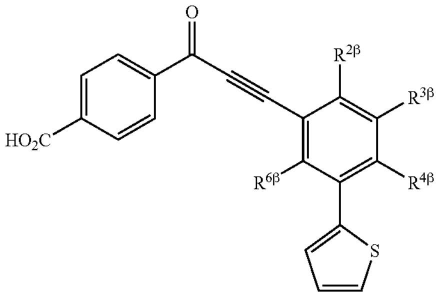

| Ex. No. | $R^{2\beta}$ | $R^{3\beta}$ | $R^{4\beta}$ | $R^{6\beta}$ |
|---|---|---|---|---|
| 864 | F | H | OMe | H |
| 865 | 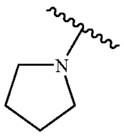 | H | F | H |
| 866 | $CF_3$ | H | F | H |
| 867 | $OCF_3$ | H | F | H |
| 868 | 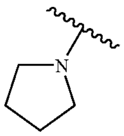 | H | OMe | H |
| 869 | OMe | H | F | H |
| 870 | OMe | H | 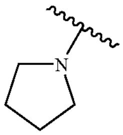 | H |
| 871 | OMe | H | F | OMe |
| 872 | OMe | H | OMe | OMe |
| 873 | OMe | H | 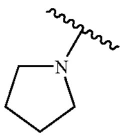 | OMe |
| 874 | OH | H | OH | H |
| 875 | $OCF_3$ | H | OH | H |
| 876 | OMe | H | OH | H |
| 877 | H | $CO_2H$ | OH | H |
| 878 | OMe | H | OH | OMe |
| 879 | Me | H | OH | Me |
| 880 | Me | H | 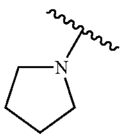 | Me |

Example Table 11
Substituted N-{4-[3-(5-Thiophen-2-yl-phenyl)-propynoyl]-methanesulfonamides
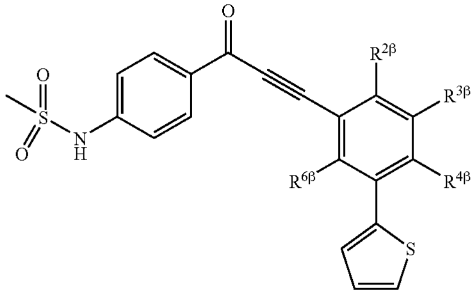
| Ex. No. | $R^{2\beta}$ | $R^{3\beta}$ | $R^{4\beta}$ | $R^{6\beta}$ |
|---|---|---|---|---|
| 881 | F | H | H | H |
| 882 | 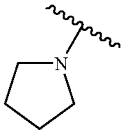 | H | H | H |
| 883 | H | H | F | H |
| 884 | H | H | 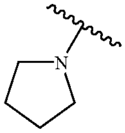 | H |
| 885 | H | H | OMe | H |
| 886 | F | H | 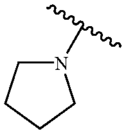 | H |
| 887 | F | H | OMe | H |
| 888 | 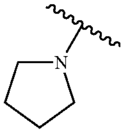 | H | F | H |
| 889 | $CF_3$ | H | F | H |
| 890 | $OCF_3$ | H | F | H |
-continued
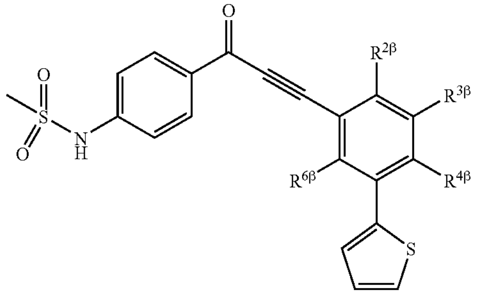
| Ex. No. | $R^{2\beta}$ | $R^{3\beta}$ | $R^{4\beta}$ | $R^{6\beta}$ |
|---|---|---|---|---|
| 891 | 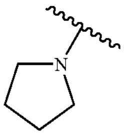 | H | OMe | H |
| 892 | OMe | H | F | H |
| 893 | OMe | H | 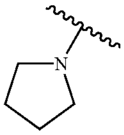 | H |
| 894 | OMe | H | F | OMe |
| 895 | OMe | H | OMe | OMe |
| 896 | OMe | H | 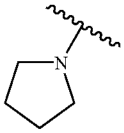 | OMe |
| 897 | OH | H | OH | H |
| 898 | $OCF_3$ | H | OH | H |
| 899 | OMe | H | OH | H |
| 900 | H | $CO_2H$ | OH | H |
| 901 | OMe | H | OH | OMe |
| 902 | Me | H | OH | Me |
| 903 | Me | H | 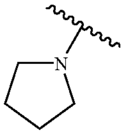 | Me |

Example Table 12

Substituted 1-[4-(1H-Tetrazol-5-yl)-phenyl]-3-(5-thiophen-2-yl-phenyl)-propynone

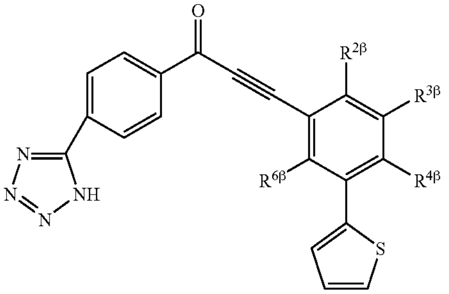

| Ex. No. | $R^{2\beta}$ | $R^{3\beta}$ | $R^{4\beta}$ | $R^{6\beta}$ |
|---|---|---|---|---|
| 904 | F | H | H | H |
| 905 | 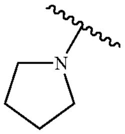 | H | H | H |
| 906 | H | H | F | H |
| 907 | H | H | 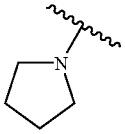 | H |
| 908 | H | H | OMe | H |
| 909 | F | H | 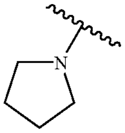 | H |
| 910 | F | H | OMe | H |
| 911 | 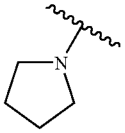 | H | F | H |
| 912 | $CF_3$ | H | F | H |
| 913 | $OCF_3$ | H | F | H |
| 914 | 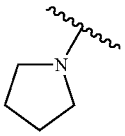 | H | OMe | H |
| 915 | OMe | H | F | H |
| 916 | OMe | H | 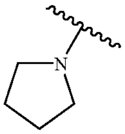 | H |

-continued

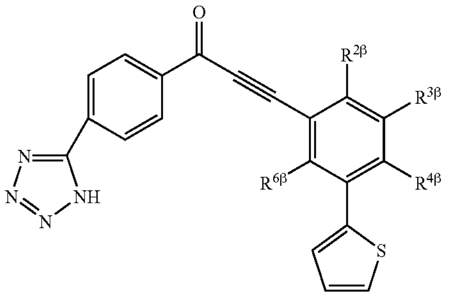

| Ex. No. | $R^{2\beta}$ | $R^{3\beta}$ | $R^{4\beta}$ | $R^{6\beta}$ |
|---|---|---|---|---|
| 917 | OMe | H | F | OMe |
| 918 | OMe | H | OMe | OMe |
| 919 | OMe | H | 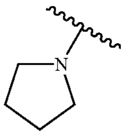 | OMe |
| 920 | OH | H | OH | H |
| 921 | $OCF_3$ | H | OH | H |
| 922 | OMe | H | OH | H |
| 923 | H | $CO_2H$ | OH | H |
| 924 | OMe | H | OH | OMe |
| 925 | Me | H | OH | Me |
| 926 | Me | H | 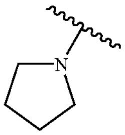 | Me |

Example Table 13

Substituted 1-(1H-Indol-5-yl)-3-(5-thiophen-2-yl-phenyl)-propynones

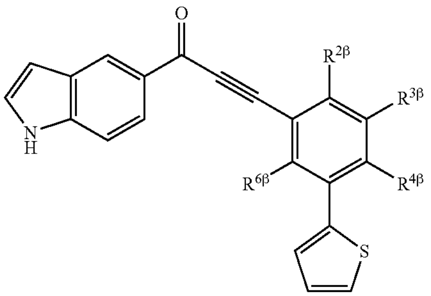

| Ex. No. | $R^{2\beta}$ | $R^{3\beta}$ | $R^{4\beta}$ | $R^{6\beta}$ |
|---|---|---|---|---|
| 927 | F | H | H | H |
| 928 | 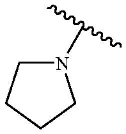 | H | H | H |

-continued

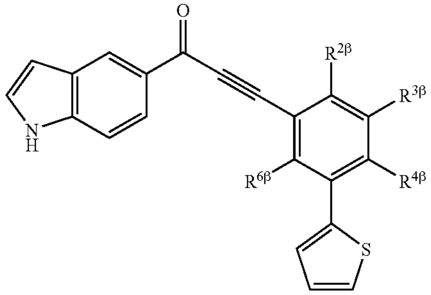

| Ex. No. | $R^{2\beta}$ | $R^{3\beta}$ | $R^{4\beta}$ | $R^{6\beta}$ |
|---|---|---|---|---|
| 929 | H | H | F | H |
| 930 | H | H | 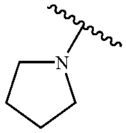 | H |
| 931 | H | H | OMe | H |
| 932 | F | H | 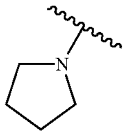 | H |
| 933 | F | H | OMe | H |
| 934 | 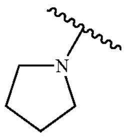 | H | F | H |
| 935 | $CF_3$ | H | F | H |
| 936 | $OCF_3$ | H | F | H |
| 937 | 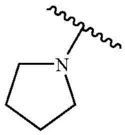 | H | OMe | H |
| 938 | OMe | H | F | H |
| 939 | OMe | H | 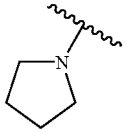 | H |
| 940 | OMe | H | F | OMe |
| 941 | OMe | H | OMe | OMe |
| 942 | OMe | H | 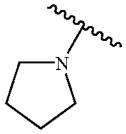 | OMe |
| 943 | OH | H | OH | H |
| 944 | $OCF_3$ | H | OH | H |

-continued

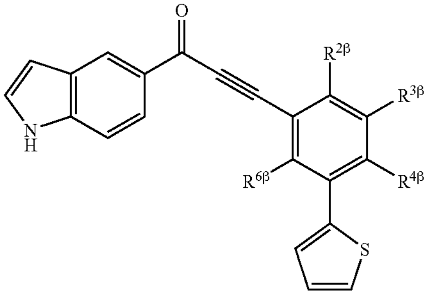

| Ex. No. | $R^{2\beta}$ | $R^{3\beta}$ | $R^{4\beta}$ | $R^{6\beta}$ |
|---|---|---|---|---|
| 945 | OMe | H | OH | H |
| 946 | H | $CO_2H$ | OH | H |
| 947 | OMe | H | OH | OMe |
| 948 | Me | H | OH | Me |
| 949 | Me | H | 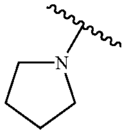 | Me |

Example Table 14

Substituted 1-(1-Methyl-1H-indol-5-yl)-3-(5-thiophen-2-yl-phenyl)-propynones

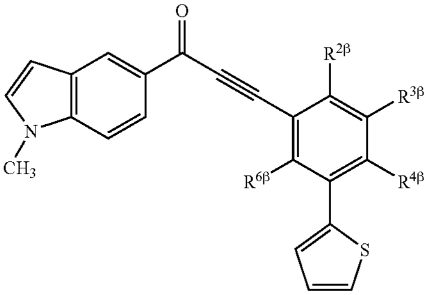

| Ex. No. | $R^{2\beta}$ | $R^{3\beta}$ | $R^{4\beta}$ | $R^{6\beta}$ |
|---|---|---|---|---|
| 950 | F | H | H | H |
| 951 | 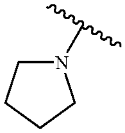 | H | H | H |
| 952 | H | H | F | H |
| 953 | H | H | 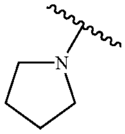 | H |
| 954 | H | H | OMe | H |

-continued

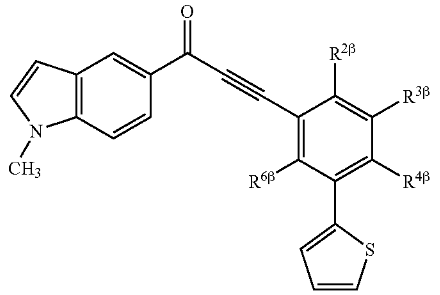

| Ex. No. | $R^{2\beta}$ | $R^{3\beta}$ | $R^{4\beta}$ | $R^{6\beta}$ |
|---|---|---|---|---|
| 955 | F | H | 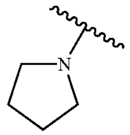 | H |
| 956 | F | H | OMe | H |
| 957 | 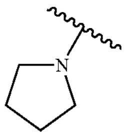 | H | F | H |
| 958 | $CF_3$ | H | F | H |
| 959 | $OCF_3$ | H | F | H |
| 960 | 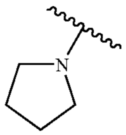 | H | OMe | H |
| 961 | OMe | H | F | H |
| 962 | OMe | H | 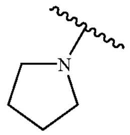 | H |
| 963 | OMe | H | F | OMe |
| 964 | OMe | H | OMe | OMe |
| 965 | OMe | H | 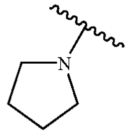 | OMe |
| 966 | OH | H | OH | H |
| 967 | $OCF_3$ | H | OH | H |
| 968 | OMe | H | OH | H |
| 969 | H | $CO_2H$ | OH | H |
| 970 | OMe | H | OH | OMe |
| 971 | Me | H | OH | Me |

-continued

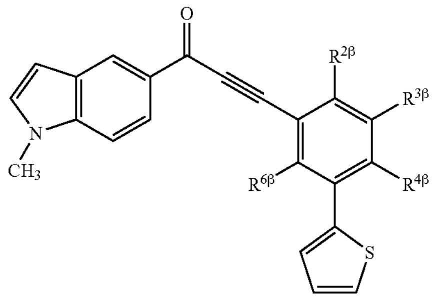

| Ex. No. | $R^{2\beta}$ | $R^{3\beta}$ | $R^{4\beta}$ | $R^{6\beta}$ |
|---|---|---|---|---|
| 972 | Me | H | 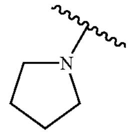 | Me |

Stereoisomerism and Polymorphism

It is appreciated that compounds of the present invention having a chiral center may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following.

i) physical separation of crystals—a technique whereby macroscopic crystals of-the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Pharmaceutically Acceptable Salt Formulations

In cases where compounds are sufficiently basic or acidic to form stable nontoxic acid or base salts, administration of the compound as a pharmaceutically acceptable salt may be appropriate. The term "pharmaceutically acceptable salts" or "complexes" refers to salts or complexes that retain the desired biological activity of the compounds of the present invention and exhibit minimal undesired toxicological effects.

Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including, sulfate, nitrate, bicarbonate and carbonate salts. Alternatively, the pharmaceutically acceptable salts may be made with sufficiently basic compounds such as an amine with a suitable acid affording a physiologically acceptable anion. Alkali metal (for example, sodium, potassium or lithium) or alkaline earth metal (for example calcium) salts of carboxylic acids can also be made.

Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —$NR^+A^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The invention also includes pharmaceutically acceptable prodrugs of the compounds. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Any of the compounds described herein can be administered as a prodrug to increase the activity, bioavailability, stability or otherwise alter the properties of the compound. A number of prodrug ligands are known. In general, alkylation, acylation or other lipophilic modification of the compound will increase the stability of the compound. Examples of substituent groups that can replace one or more hydrogens on the compound are alkyl, aryl, steroids, carbohydrates, including sugars, 1,2-diacylglycerol and alcohols. Many are described in R. Jones and N. Bischofberger, *Antiviral Research,* 27 (1995) 1–17. Any of these can be used in combination with the disclosed compounds to achieve a desired effect.

The compounds can be used to treat inflammatory disorders that are mediated by VCAM-1 including, but not limited to arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

The compounds disclosed herein can be used in the treatment of inflammatory skin diseases that are mediated by VCAM-1, and in particular, human endothelial disorders that are mediated by VCAM-1, which include, but are not limited to, psoriasis, dermatitis, including eczematous dermatitis, and Kaposi's sarcoma, as well as proliferative disorders of smooth muscle cells.

In yet another embodiment, the compounds disclosed herein can be selected to treat anti-inflammatory conditions that are mediated by mononuclear leucocytes.

In yet another embodiment, the compounds of the present invention can be selected for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. They are also indicated for the prevention or treatment of graft-versus-host disease, which sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

In another aspect the invention provides pharmaceutical compositions for the treatment of diseases or disorders mediated by VCAM-1 wherein such compositions comprise a VCAM-1 inhibiting amount of a compound of the invention or a pharmaceutically acceptable salt thereof and/or a pharmaceutically acceptable carrier.

In another aspect the invention provides a method for treating a disease or disorder mediated by VCAM-1 comprising administering to a patient a VCAM-1 inhibiting effective amount of a compound of the invention or a pharmaceutically acceptable salt thereof.

In another aspect the invention provides a method for treating cardiovascular and inflammatory disorders in a patient in need thereof comprising administering to said patient an VCAM-1 inhibiting effective amount of a compound of the invention or a pharmaceutically acceptable salt thereof.

In another aspect the invention provides a method and composition for treating asthma or arthritis in a patient in need thereof comprising administering to said patient an effective amount of a compound of the invention or a pharmaceutically acceptable salt thereof.

The compounds of the present invention can be used to treat any disorder that is mediated by VCAM-1. VCAM-1 is upregulated in a wide variety of disease states, including but not limited to arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, rhinitis, ischemia-reperfusion injury, post-angioplasty restenosis, chronic obstructive pulmonary disease (COPD), glomerulonephritis, Graves disease, gastrointestinal allergies, atherosclerosis, coronary artery disease, angina, small artery disease, and conjunctivitis.

Nonlimiting examples of arthritis include rheumatoid (such as soft-tissue rheumatism and non-articular rheumatism, fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, spondyloarthropaties (ankylosing spondylitis), osteoarthritis, hyperuricemia and arthritis associated with acute gout, chronic gout and systemic lupus erythematosus.

Human endothelial disorders mediated by VCAM-1 include psoriasis, eczematous dermatitis, Kaposi's sarcoma, as well as proliferative disorders of smooth muscle cells.

In yet another embodiment, the compounds disclosed herein can be selected to treat anti-inflammatory conditions that are mediated by mononuclear leucocytes.

In one embodiment, the compounds of the present invention are selected for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. The compounds can also be used in the prevention or treatment of graft-versus-host disease, such as sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

In addition to inhibiting the expression of VCAM-1, some of the compounds of the invenion have the additional properties of inhibiting monocyte chemoattractant protein-1 (MCP-1) and/or smooth muscle proliferation. MCP-1 is a chemoattractant protein produced by endothelial cells, smooth muscle cells as well as macrophages. MCP-1 promotes integrin activation on endothelial cells thereby facilitating adhesion of leukocytes to VCAM-1, and MCP-1 is a chemoattractant for monocytes. MCP-1 has been shown to play a role in leukocyte recruitment in a number of chronic inflammatory diseases including atherosclerosis, rheumatoid arthritis, and asthma. Its expression is upregulated in these diseases and as such inhibition of MCP-1 expression represents a desirable property of anti-inflammatory therapeutics. Furthermore, smooth muscle cell hyperplasia and resulting tissue remodeling and decreased organ function is yet another characteristic of many chronic inflammatory diseases including atherosclerosis, chronic transplant rejection and asthma. Inhibition of the hyperproliferation of smooth muscle cells is another desirable property for therapeutic compounds.

Combination and Alternation Therapy

Any of the compounds disclosed herein can be administered in combination or alternation with a second biologically active agent to increase its effectiveness against the target disorder.

In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The efficacy of a drug can be prolonged, augmented, or restored by administering the compound in combination or alternation with a second, and perhaps third, agent that induces a different biological pathway from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the condition.

Any method of alternation can be used that provides treatment to the patient. Nonlimiting examples of alternation patterns include 1–6 weeks of administration of an effective amount of one agent followed by 1–6 weeks of administration of an effective amount of a second agent. The alternation schedule can include periods of no treatment. Combination therapy generally includes the simultaneous administration of an effective ratio of dosages of two or more active agents.

Illustrative examples of specific agents that can be used in combination or alternation with the compounds of the present invention are described below in regard to asthma and arthritis. The agents set out below or others can alternatively be used to treat a host suffering from any of the other disorders listed above or that are mediated by VCAM-1 or MCP-1. Illustrative second biologically active agents for the treatment of cardiovascular disease are also provided below.

Asthma

In one embodiment, the compounds of the present invention are administered in combination or alternation with heparin, frusemide, ranitidine, an agent that effects respiratory function, such as DNAase, or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, leukotriene-$D_4$-receptor antagonists such as Accolate (zafirlukast), Ziflo (zileuton), leukotriene $C_1$ or $C_2$ antagonists and inhibitors of leukotriene synthesis such as zileuton for the treatment of asthma, or an inducible nitric oxide synthase inhibitor.

In another embodiment, the active compound is administered in combination or alternation with one or more other prophylactic agent(s). Examples of prophylactic agents that can be used in alternation or combination therapy include but are not limited to sodium cromoglycate, Intal (cromolyn sodium, Nasalcrom, Opticrom, Crolom, Ophthalmic Crolom), Tilade (nedocromil, nedocromil sodium) and ketotifen.

In another embodiment, the active compound is administered in combination or alternation with one or more other $\beta_2$-adrenergic agonist(s) (β agonists). Examples of $\beta_2$-adrenergic agonists (β agonists) that can be used in alternation or combination therapy include but are not limited to albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tomalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirmoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, psuedoephedrine (psuedoephedrine polixtirex, psuedoephedrine tannate, psuedoephedrine hydrochloride, psuedoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metassulphobenzoate, Dexamethasonev Soddium Phosphate), Dichlorisone Acetate, Diflorasone Diacetate, Diflucortolone Valerate, Difluprednate, Domoprednate, Endrysone, Fluazacort, Fluclorolone Acetonide, Fludrbcortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other antihistimine(s) ($H_1$ receptor antagonists). Examples of antihistimines ($H_1$ receptor antagonists) that can be used in alternation or combination therapy include alkylamines, ethanolamines ethylenediamines, piperazines, piperidines or phenothiazines. Some non-limiting examples of antihistimes are Chlortrimeton (Teldrin, chlorpheniramine), Atrohist (brompheniramine, Bromarest, Bromfed, Dimetane), Actidil (triprolidine), Dexchlor (Poladex, Polaramine, dexchlorpheniramine), Benadryl (diphenhydramine), Tavist (clemastine), Dimetabs (dimenhydrinate, Dramamine, Marmine), PBZ (tripelennamine), pyrilamine, Marezine (cyclizine), Zyrtec (cetirizine), hydroxyzine, Antivert (meclizine, Bonine), Allegra (fexofenadine), Hismanal (astemizole), Claritin (loratadine), Seldane (terfenadine), Periactin (cyproheptadine), Nolamine (phenindamine, Nolahist), Phenameth (promethazine, Phenergan), Tacaryl (methdilazine) and Temaril (trimeprazine).

Alternatively, the compound of the present invention is administered in combination or alternation with (a) xanthines and methylxanthines, such as Theo-24 (theophylline, Slo-Phylline, Uniphyllin, Slobid, Theo-Dur), Choledyl (oxitriphylline), aminophylline;

(b) anticholinergic agents (antimuscarinic agents) such as belladonna alkaloids, Atrovent (ipratropium bromide), atropine, oxitropium bromide;

(c) phosphodiesterase inhibitors such as zardaverine;

(d) calcium antagonists such as nifedipine; or (e) potassium activators such as cromakalim for the treatment of asthma.

Arthritic Disorders

In one embodiment, the compound of the present invention can also be administered in combination or alternation with apazone, amitriptyline, chymopapain, collegenase, cyclobenzaprine, diazepam, fluoxetine, pyridoxine, ademetionine, diacerein, glucosamine, hylan (hyaluronate), misoprostol, paracetamol, superoxide dismutase mimics, TNFα receptor antagonists, TNFα antibodies, P38 Kinase inhibitors, tricyclic antidepressents, cJun kinase inhibitors or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, and inducible nitric oxide sythase inhibitors.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicdtinate, Dexamethasone Phosphate, Dexamethasone Sodium Metasulphobenzoate, Dekamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other non-steroidal anti-inflammatory drug(s) (NSAIDS). Examples of NSAIDS that can be used in alternation or combination therapy are carboxylic acids, propionic acids, fenamates, acetic acids, pyrazolones, oxicans, alkanones, gold compounds and others that inhibit prostaglandin synthesis, preferably by selectively inhibiting cylcooxygenase-2 (COX-2). Some nonlimiting examples of COX-2 inhibitors are Celebrex (celecoxib), Bextra (valdecoxib), Dynastat (parecoxib sodium) and Vioxx (rofacoxib). Some non-limiting examples of NSAIDS are aspirin (acetylsalicylic acid), Dolobid (diflunisal), Disalcid (salsalate, salicylsalicylate), Trisilate (choline magnesium trisalicylate), sodium salicylate, Cuprimine (penicillamine), Tolectin (tolmetin), ibuprofen (Motrin, Advil, Nuprin Rufen), Naprosyn (naproxen, Anaprox, naproxen sodium), Nalfon (fenoprofen), Orudis (ketoprofen), Ansaid (flurbiprofen), Daypro (oxaprozin), meclofenamate (meclofanamic acid, Meclomen), mefenamic acid, Indocin (indomethacin), Clinoril (sulindac), tolmetin, Voltaren (diclofenac), Lodine (etodolac), ketorolac, Butazolidin (phenylbutazone), Tandearil (oxyphenbutazone), piroxicam (Feldene), Relafen (nabumetone), Myochrysine (gold sodium thiomalate), Ridaura (auranofin), Solganal (aurothioglucose), acetaminophen, colchicine, Zyloprim (allopurinol), Benemid (probenecid), Anturane (sufinpyrizone), Plaquenil (hydroxychloroquine), Aceclofenac, Acemetacin, Acetanilide, Actarit, Alclofenac, Alminoprofen, Aloxiprin, Aluminium Aspirin, Amfenac Sodium, Amidopyrine, Aminopropylone, Ammonium Salicylate, Ampiroxicam, Amyl Salicylate, Anirolac, Aspirin, Auranofin, Aurothioglucose, Aurotioprol, Azapropazone, Bendazac (Bendazac Lysine), Benorylate, Benoxaprofen, Benzpiperylone, Benzydamine, Hydrochloride, Bornyl Salicylate, Bromfenac Sodium, Bufexamac, Bumadizone Calcium, Butibufen Sodium, Capsaicin, Carbaspirin Calcium, Carprofen, Chlorthenoxazin, Choline Magnesium Trisalicylate, Choline Salicylate, Cinmetacin, Clofexamide, Clofezone, Clometacin, Clonixin, Cloracetadol, Cymene, Diacerein, Diclofenac (Diclofenac Diethylammonium Salt, Diclofenac Potassium, Diclofenac Sodium), Diethylamine Salicylate, Diethylsalicylamide, Difenpiramide, Diflunisal, Dipyrone, Droxicam, Epirizole, Etenzamide, Etersalate, Ethyl Salicylate, Etodolac, Etofenamate, Felbinac, Fenbufen, Fenclofenac, Fenoprofen Calcium, Fentiazac, Fepradinol, Feprazone, Floctafenine, Flufenamic, Flunoxaprofen, Flurbiprofen (Flurbiprofen Sodium), Fosfosal, Furprofen, Glafenine, Glucametacin, Glycol Salicylate, Gold Keratinate, Harpagophytum Procumbens, Ibufenac, Ibuprofen, Ibuproxam, Imidazole Salicylate, Indomethacin (Indomethacin Sodium), Indoprofen, Isamifazone, Isonixin, Isoxicam, Kebuzone, Ketoprofen, Ketorolac Trometamol, Lithium Salicylate, Lonazolac Calcium, Lomoxicam, Loxoprofen Sodium, Lysine Aspirin, Magnesium Salicylate, Meclofenamae Sodium, Mefenamic Acid, Meloxicam, Methyl Butetisalicylate, Methyl Gentisate, Methyl Salicylate, Metiazinic Acid, Metifenazone, Mofebutazone, Mofezolac, Morazone Hydrochloride, Morniflumate, Morpholine Salicylate, Nabumetone, Naproxen (Naproxen Sodium), Nifenazone, Niflumic Acid, Nimesulide, Oxametacin, Oxaprozin, Oxindanac, Oxyphenbutazone, Parsalmide, Phenybutazone, Phenyramidol Hydrochloride, Picenadol Hydrochloride, Picolamine Salicylate, Piketoprofen, Pirazolac, Piroxicam, Pirprofen, Pranoprofen, Pranosal, Proglumetacin Maleate, Proquazone, Protizinic Acid, Ramifenazone, Salacetamide, Salamidacetic Acid, Salicylamide, Salix, Salol, Salsalate, Sodium Aurothiomalate, Sodium Gentisate, Sodium Salicylate, Sodium Thiosalicylate, Sulindac, Superoxide Dismutase (Orgotein, Pegorgotein, Sudismase), Suprofen, Suxibuzone, Tenidap Sodium, Tenoxicam, Tetrydamine, Thurfyl Salicylate, Tiaprofenic, Tiaramide Hydrochloride, Tinoridine Hydrochloride, Tolfenamic Acid, Tometin Sodium, Triethanolamine Salicylate, Ufenamate, Zaltoprofen, Zidometacin and Zomepirac Sodium.

Cardiovascular Disease

Compounds useful for combining with the compounds of the present invention for the treatment of cardiovascular disease encompass a wide range of therapeutic compounds.

Ileal bile acid transporter (IBAT) inhibitors, for example, are useful in the present invention, and are disclosed in patent application no. PCT/US95/10863, herein incorporated by reference. More IBAT inhibitors are described in PCT/US97/04076, herein incorporated by reference. Still further IBAT inhibitors useful in the present invention are described in U.S. application Ser. No. 08/816,065, herein incorporated by reference. More IBAT inhibitor compounds useful in the present invention are described in WO 98/40375, and WO 00/38725, herein incorporated by reference. Additional IBAT inhibitor compounds useful in the present invention are described in U.S. application Ser. No. 08/816,065, herein incorporated by reference.

In another aspect, the second biologically active agent is a statin. Statins lower cholesterol by inhibiting of 3-hydroxy-3-methylglutaryl coenzyme A (HMG CoA) reductase, a key enzyme in the cholesterol biosynthetic pathway. The statins decrease liver cholesterol biosynthesis, which increases the production of LDL receptors thereby decreasing plasma total and LDL cholesterol (Grundy, S. M. *New Engl. J. Med.* 319, 24 (1988); Endo, A. *J. Lipid Res.* 33, 1569 (1992)). Depending on the agent and the dose used, statins may decrease plasma triglyceride levels and may increase HDLc. Currently the statins on the market are lovastatin (Merck), simvastatin (Merck), pravastatin (Sankyo and Squibb) and fluvastatin (Sandoz). A fifth statin, atorvastatin (Parke-Davis/Pfizer), is the most recent entrant into the statin market. Any of these statins or thers can be used in combination with the compounds of the present invention.

MTP inhibitor compounds useful in the combinations and methods of the present invention comprise a wide variety of structures and functionalities. Some of the MTP inhibitor compounds of particular interest for use in the present invention are disclosed in WO 00/38725, the disclosure from which is incorporated by reference. Descriptions of these therapeutic compounds can be found in *Science,* 282, 23 Oct. 1998, pp. 751–754, herein incorporated by reference.

Cholesterol absorption antagonist compounds useful in the combinations and methods of the present invention comprise a wide variety of structures and functionalities. Some of the cholesterol absorption antagonist compounds of particular interest for use in the present invention are described in U.S. Pat. No. 5,767,115, herein incorporated by reference. Further cholesterol absorption antagonist compounds of particular interest for use in the present invention, and methods for making such cholesterol absorption antagonist compounds are described in U.S. Pat. No. 5,631,365, herein incorporated by reference.

A number of phytosterols suitable for the combination therapies of the present invention are described by Ling and Jones in "Dietary Phytosterols: A Review of Metabolism, Benefits and Side Effects," *Life Sciences,* 57 (3), 195–206 (1995). Without limitation, some phytosterols of particular use in the combination of the present invention are Clofibrate, Fenofibrate, Ciprofibrate, Bezafibrate, Gemfibrozil. The structures of the foregoing compounds can be found in WO 00/38725.

Phytosterols are also referred to generally by Nes (*Physiology and Biochemistry of Sterols*, American Oil Chemists' Society, Champaign, Ill., 1991, Table 7–2). Especially preferred among the phytosterols for use in the combinations of the present invention are saturated phytosterols or stanols. Additional stanols are also described by Nes (Id.) and are useful in the combination of the present invention. In the combination of the present invention, the phytosterol preferably comprises a stanol. In one preferred embodiment the stanol is campestanol. In another preferred embodiment the stanol is cholestanol. In another preferred embodiment the stanol is clionastanol. In another preferred embodiment the stanol is coprostanol. In another preferred embodiment the stanol is 22,23-dihydrobrassicastanol. In another embodiment the stanol is epicholestanol. In another preferred embodiment the stanol is fucostanol. In another preferred embodiment the stanol is stigmastanol.

Another embodiment the present invention encompasses a therapeutic combination of a compound of the present invention and an HDLc elevating agent. In one aspect, the second HDLc elevating agent can be a CETP inhibitor. Individual CETP inhibitor compounds useful in the present invention are separately described in WO 00/38725, the disclosure of which is herein incorporated by reference. Other individual CETP inhibitor compounds useful in the present invention are separately described in WO99/14174, EP818448, WO 99/15504, WO 99/14215, WO 98/04528, and WO 00/17166, the disclosures of which are herein incorporated by reference. Other individual CETP inhibitor compounds useful in the present invention are separately described in WO 00/18724, WO 00/18723, and WO 00/18721, the disclosures of which are herein incorporated by reference. Other individual CETP inhibitor compounds useful in the present invention are separately described in WO 98/35937 as well as U.S. Pat. Nos. 6,313,142, 6,310,075, 6,197,786, 6,147,090, 6,147,089, 6,140,343, and 6,140,343, the disclosures of which is herein incorporated by reference.

In another aspect, the second biologically active agent can be a fibric acid derivative. Fibric acid derivatives useful in the combinations and methods of the present invention comprise a wide variety of structures and functionalities which have been reported and published in the art.

In another embodiment the present invention encompasses a therapeutic combination of a compound of the present invention and an antihypertensive agent. Hypertension is defined as persistently high blood pressure. In another embodiment, the compound of the invention is administered in combination with an ACE inhibitor, a beta andrenergic blocker, alpha andrenergic blocker, angiotensin II receptor antagonist, vasodilator and diuretic.

Pharmaceutical Compositions

Any host organism, including a pateint, mammal, and specifically a human, suffering from any of the above-described conditions can be treated by the administration of a composition comprising an effective amount of the compound of the invention or a pharmaceutically acceptable salt thereof, optionally in a pharmaceutically acceptable carrier or diluent.

The composition can be administered in any desired manner, including oral, topical, parenteral, intravenous, intradermal, intra-articular, intra-synovial, intrathecal, intra-arterial, intracardiac, intramuscular, subcutaneous, intraorbital, intracapsular, intraspinal, intrasternal, topical, transdermal patch, via rectal, vaginal or urethral suppository, peritoneal, percutaneous, nasal spray, surgical implant, internal surgical paint, infusion pump, or via catheter. In one embodiment, the agent and carrier are administered in a slow release formulation such as an implant, bolus, microparticle, microsphere nanoparticle or nanosphere. For standard information on pharmaceutical formulations, see Ansel, et al., *Pharmaceutical Dosage Forms and Drug Delivery Systems*, Sixth Edition, Williams & Wilkins (1995).

An effective dose for any of the herein described conditions can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication. Typical systemic dosages for all of the herein described conditions are those ranging from 0.1 mg/kg to 500 mg/kg of body weight per day as a single daily dose or divided daily doses. Preferred dosages for the described conditions range from 5–1500 mg per day. A more particularly preferred dosage for the desired conditions ranges from 25–750 mg per day. Typical dosages for topical application are those ranging from 0.001 to 100% by weight of the active compound.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

The compound can also be mixed with other active materials that do not impair the desired action, or with materials that supplement the desired action. The compounds can also be administered in combination with nonsteroidal antiinflammatories such as ibuprofen, indomethacin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If administered intravenously, preferred carriers are physiological saline, bacteriostatic water, Cremophor EL™ (BASF, Parsippany, N.J.) or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Any of the compounds described herein for combination or alternation therapy can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound. This can easily be assessed by preparing the derivative and testing its anti-inflammatory activity according to known methods.

Biological Activity of Active Compounds

The ability of a compound described herein to inhibit the expression of VCAM-1 or in the treatment of diseases in a host can be assessed using any known method, including that described in detail below.

In Vitro MCP-1 Activity Assay

Cultured human endothelial cells can be seeded in 96-well plates. On the following day cells can be stimulated with TNF-α (1 ng/ml) in the presence or absence of compounds dissolved in DMSO. To establish a dose curve and $IC_{50}$ for each compound, multiple concentrations in 2- to 5-fold increments are used. Cells are exposed to TNF-α and compounds for approximately 16 hours. The next day the cells are visually examined via light microscopy to score for visual signs of toxicity. Cell culture media, diluted 1:10, is analyzed by an MCP-1 immunoassay kit (R & D Systems). This assay is a sandwich immunoassay using immobilized anti-MCP-1 antibody in 96-well plate to capture secreted MCP-1 in cell culture media. Captured MCP-1 is subsequently detected with a horse radish peroxidase-conjugated anti-MCP antibody for color development. Results are expressed as $IC_{50}$ values (the amount of compound (μM) required to achieve a 50% reduction compared to control (cells stimulated with TNF-α only)).

In Vitro Smooth Muscle Cell Activity Assay

Cultured human aortic smooth muscle cells are seeded in 24-well plates. When cells reached 80% confluency, they are made quiescent by changing media to 0.2% serum (as compared to 5% serum in normal culture media) for 48 hours. The cells are then stimulated by addition of 5% serum in the presence or absence of compounds dissolved in DMSO. To establish a dose curve and $IC_{50}$ for each compound, multiple concentrations in 5-fold increments are used. After 20 hr incubation, $^3$H-thymidine (0,5 μCi/per well) is added to the cells for 4 hours of labeling. Washed cells are then lysed in NaOH and, the amount of $^3$H-thymidine incorporation is determined. Results are expressed as $IC_{50}$ values (the amount of compound (μM) required to achieve a 50% reduction compared to control (cells stimulated with 5% serum only)).

In Vitro VCAM-1 Assay

Cell Culture and compound dosing: Cultured primary human aortic (HAEC) or pulmonary (HPAEC) endothelial cells were obtained from Clonetics, Inc., and were used below passage 9. Cells were seeded in 96 well plates such that they would reach 90–95% confluency by the following day. On the following day the cells were stimulated with TNF-α (1 ng/ml) in the presence or absence of compounds dissolved in DMSO such that the final concentration of DMSO is 0.25% or less. To establish a dose curve for each compound, four concentrations in 2- to 5-fold increments were used. Cells were exposed to TNF-α and compounds for approximately 16 hours. The next day the cells were examined under microscope to score for visual signs of toxicity or cell stress.

Following 16 hr exposure to TNF-α and compound the media was discarded and the cells were washed once with Hanks Balanced Salt Solution (HBSS)/Phosphate buffered saline (PBS) (1:1). Primary antibodies against VCAM-1 (0.25 μg/ml in HBSS/PBS+5% FBS) were added and incubated for 30–60 minutes at 37° C. Cells were washed with HBSS/PBS three times, and secondary antibody Horse Radish Peroxidase (HRP)-conjugated goat anti-mouse IgG (1:500 in HBSS/PBS+5% FBS) were added and incubated for 30 minutes at 37° C. Cells were washed with HBSS/PBS four time and TMB substrate were added and incubated at room temperature in the dark until there was adequate development of blue color. The length of time of incubation was typically 5–15 minutes. 2N sulfuric acid was added to stop the color development and the data was collected by reading the absorbance on a BioRad ELISA plate reader at OD 450 nm. The results are expressed as $IC_{50}$ values (the concentration (micromolar) of compound required to inhibit 50% of the maximal response of the control sample stimulated by TNF-α only). Compounds exhibiting $IC_{50}$'s of less than 5 micromolar are tabulated in VCAM-1 Table 1.

TABLE 1

VCAM-1

| Example No. | VCAM-1 $IC_{50}$ (μM) |
|---|---|
| 2 | <5 |
| 3 | <5 |
| 4 | <5 |

We claim:

1. A compound of Formula I:

(I)

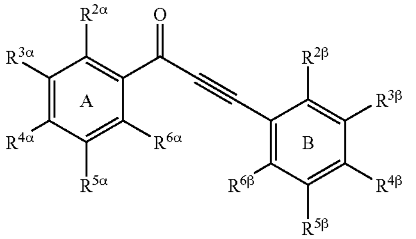

or its pharmaceutically acceptable salt or ester, wherein:

$R^{2\alpha}$, $R^{3\alpha}$, $R^{5\alpha}$, $R^{6\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $OC(R^1)_2COOH$, $SC(R^1)_2COOH$, $NHC(R^1)_2COOH$, $C(O)R^2$, $COOR^1$, polyoxyalkylene, polyol alkyl, alkylcarbonylalkyl, lower alkyl S(O) lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{2\beta}$, $R^{3\beta}$, $R^{4\beta}$, $R^{5\beta}$ or $R^{6\beta}$, or one of $R^{2\alpha}$, $R^{3\alpha}$, $R^{4\alpha}$, $R^{5\alpha}$ or $R^{6\alpha}$ must be a carbon-carbon linked heterocycle or heteroaryl;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $OC(R^1)_2COOH$; or at least one of $R^{2\alpha}$, $R^{3\alpha}$, $R^{4\alpha}$, $R^{5\alpha}$, $R^{6\alpha}$ or one of $R^{2\beta}$, $R^{3\beta}$, $R^{4\beta}$, $R^{5\beta}$, $R^{6\beta}$ must be selected from the group consisting of carboxy, carboxyalkoxy, cyano, tetrazol-5-yl, —$C(O)OR^2$, —$C(O)NHR^2$, —$C(O)NH_2$, —$C(O)N(R^2)_2$, —$C(CH_3)_2C(O)OH$, —$CH_2C(O)OH$, —$NHR^2$, $NH_2$, —$NHSO_2R^2$, $N(R^2)_2$, —$NR^2SO_2R^2$, —$NHSO_2NHR^2$, —$NHC(O)R^2$, —$NHC(O)OR^2$, —$SCH_2CO_2H$, —$SCF_2CO_2H$, —SH, —$SR^2$, —$NR^2C(O)R^2$, —$NHC(O)SR^2$, $NHC(O)NHR^2$, —$NHC(O)N(R^2)_2$, $SC(R^1)_2COOH$, —$SO_2NH_2$, —$SO_2NHR^2$, —$SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

2. A compound of the Formula I:

(I)

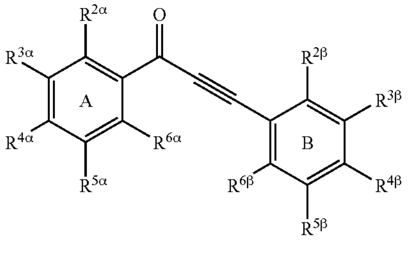

or its pharmaceutically acceptable salt or ester, wherein: $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo; wherein one of $R^{4\beta}$, $R^{5\beta}$ or $R^{6\beta}$ must be a carbon-carbon linked heterocycle or heteroaryl;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; or $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be $—OC(R^1)_2COOH$; or at least one of $R^{2\alpha}$, $R^{3\alpha}$ $R^{4\alpha}$ or one of $R^{2\beta}$, $R^{3\beta}$ $R^{4\beta}$ must be selected from the group consisting of carboxy, carboxyalkoxy, cyano, tetrazol-5-yl, $—C(O)OR^2$, $—C(O)NHR^2$, $—C(O)NH_2$, $—C(O)N(R^2)_2$, $—C(CH_3)_2C(O)OH$, $—CH_2C(O)OH$, $—NHR^2$, $NH_2$, $—NHSO_2R^2$, $N(R^2)_2$, $—NR^2SO_2R^2$, $—NHSO_2NHR^2$, $—NHC(O)R^2$, $—NHC(O)OR^2$, $—SCH_2CO_2H$, $—SCF_2CO_2H$, $—SH$, $—SR^2$, $—NR^2C(O)R^2$, $—NHC(O)SR^2$, $NHC(O)NHR^2$, $—NHC(O)N(R^2)_2$, $SC(R^1)_2COOH$, $—SO_2NH_2$, $—SO_2NHR^2$, $—SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

3. A compound of the Formula I:

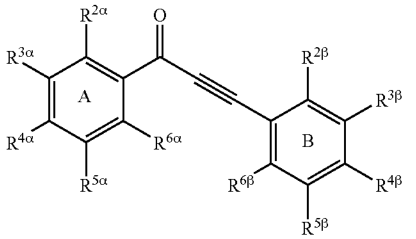

(I)

or its pharmaceutically acceptable salt or ester, wherein: $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, $—OC(R^1)_2COOH$, $—SC(R^1)_2COOH$, $—NHC(R^1)_2COOH$, $—C(O)R^2$, $—COOR^1$, polyoxyalkylene, polyol alkyl, alkylcarbonylalkyl, lower alkyl S(O)-lower alkyl, lower alkyl-S$(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, $—C(O)NH_2$, $—C(O)NHR^2$, $—C(O)N(R^2)_2$, $—NHC(O)R^2$, $—N(R^2)C(O)R^2$, $—NHC(O)OR^2$, $—NHC(O)SR^2$, $—NHSO_2NHR^2$, $—SO_2NH_2$, $—SO_2NHR_2$, $—SO_2N(R^2)_2$, $—PO_2H_2$, $—PO_3H_2$, $P(R^2)O_2H$, $—SCF_2CO_2H$, $—NHSO_2R^2$, $—N(C(O)NHR^2)_2$, $—NR^2SO_2R^2$, $—NHC(O)NHR^2$, and $—NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together form a heterocycle or heteroaryl substituted by one or more hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, and halo; or $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- or 6-membered ring containing one nitrogen, which may optionally be substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo, provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —$OC(R^1)_2COOH$; or at least one of $R^{2\alpha}$, $R^{3\alpha}$, or $R^{4\alpha}$ must be selected from the group consisting of carboxy, carboxyalkoxy, cyano, tetrazol-5-yl, —$C(O)OR^2$, —$C(O)NHR^2$, —$C(O)NH_2$, —$C(O)N(R^2)_2$, —$C(CH_3)_2C(O)OH$, —$CH_2C(O)OH$, —$NHR^2$, $NH_2$, —$NHSO_2R^2$, $N(R^2)_2$, —$NR^2SO_2R^2$, —$NHSO_2NHR^2$, —$NHC(O)R^2$, —$NHC(O)OR^2$, —$SCH_2CO_2H$, —$SCF_2CO_2H$, —SH, —$SR^2$—$NR^2C(O)R^2$, —$NHC(O)SR^2$, $NHC(O)NHR^2$, —$NHC(O)N(R^2)_2$, $SC(R^1)_2COOH$, —$SO_2NH_2$, —$SO_2NHR^2$, —$SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

4. A compound of the Formula I:

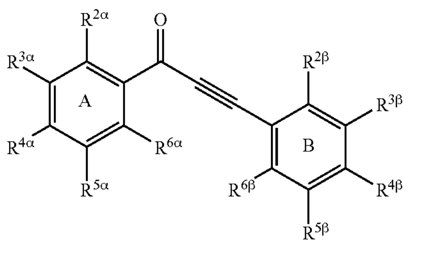

(I)

or its pharmaceutically acceptable salt or ester, wherein: $R^{2\alpha}$, $R^{3\alpha}$, $R^{4\alpha}$, $R^{5\alpha}$, $R^{6\alpha}$, $R^{2\beta}$, $R^{3\beta}$, $R^{4\alpha}$, $R^{5\beta}$ and $R^{6\beta}$ are independently selected from the group consisting of hydrogen, alkyl, lower alkyl, alkenyl, alkynyl, hydroxyl, carboxy, carbocycle, aryl, heteroaryl, heterocycle, cycloalkyl, cyano, tetrazol-5-yl, alkoxy, lower alkoxy, aryloxy, arylalkoxy, heteroaryloxy, heteroarylalkoxy, alkylthio, alkylamino, aminoalkyl, haloalkylthio, acyl, haloalkyl, acylamino, amino, dialkylamino, haloalkoxy, alkylsulfonyl, haloalkylsulfonyl, halogen, thiol, nitro, sulfonic acid, sulfonate, sulfate, sulfinic acid, sulfenic acid, phosphate, alditol, carbohydrate, —$OC(R^1)_2COOH$, —$SC(R^1)_2COOH$, —$NHC(R^1)_2COOH$, —$C(O)R^2$, —$COOR^1$, polyoxyalkylene, polyol alkyl, alkylcarbonylalkyl, lower alkyl S(O)-lower alkyl, lower alkyl-$S(O)_2$-lower alkyl; hydroxyalkyl, heteroaryl lower alkoxy, heterocyclo lower alkoxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, arylamino, heterocycleamino, heteroarylamino, cycloalkylamino, cycloalkylalkyl, heterocyclealkoxy, cycloalkylalkoxy, cycloalkyloxy, alkylthioalkyl, cycloalkylthioalkyl, cycloalkylaminoalkyl, —$C(O)NH_2$, —$C(O)NHR^2$, —$C(O)N(R^2)_2$, —$NHC(O)R^2$, —$N(R^2)C(O)R^2$, —$NHC(O)OR^2$, —$NHC(O)SR^2$, —$NHSO_2NHR^2$, —$SO_2NH_2$, —$SO_2NHR_2$, —$SO_2N(R^2)_2$, —$PO_2H_2$, —$PO_3H_2$, $P(R^2)O_2H$, —$SCF_2CO_2H$, —$NHSO_2R^2$, —$N(C(O)NHR^2)_2$, —$NR^2SO_2R^2$, —$NHC(O)NHR^2$, and —$NHC(O)N(R^2)_2$, all of which can be optionally substituted by one or more selected from the group consisting of hydroxy, alkyl, lower alkyl, alkenyl, carboxy, hydroxyalkyl, carboxyalkyl, aminoalkyl, amino, cyano, alkoxy, acyl, alkoxycarbonyl, oxo, and halo;

$R^1$ is independently selected from the group consisting of hydrogen, lower alkyl, carbocycle, cycloalkyl, aryl, heteroaryl, heterocycle, arylalkyl, heteroarylalkyl and heterocyclealkyl, wherein all may be optionally substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

$R^2$ is independently selected from the group consisting of alkyl, lower alkyl, alkenyl, alkynyl, aryl, carbocycle, heteroaryl, heterocycle, arylalkyl, heteroarylalkyl, and heterocyclealkyl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\beta}$, $R^{3\alpha}$, or $R^{4\alpha}$ must be selected from the group consisting of carboxy, carboxyalkoxy, cyano, tetrazol-5-yl, —$C(O)OR^2$, —$C(O)NHR^2$, —$C(O)NH_2$, —$C(O)N(R^2)_2$, —$C(CH_3)_2C(O)OH$, —$CH_2C(O)OH$, —$NHR^2$, $NH_2$, —$NHSO_2R^2$, $N(R^2)_2$, —$NR^2SO_2R^2$, —$NHSO_2NHR^2$, —$NHC(O)R^2$, —$NHC(O)OR^2$, $SC(R^1)_2COOH$, —$SCH_2CO_2H$, —$SCF_2CO_2H$, —SH, —$SR^2$, —$NR^2C(O)R^2$, —$NHC(O)SR^2$, $NHC(O)NHR^2$, —$NHC(O)N(R^2)_2$, —$SO_2NH_2$, —$SO_2NHR^2$, —$SO_2N(R^2)_2$, and $NR^7R^7$ wherein $R^7$ and $R^7$ are linked together forming a 4- to 7-membered ring that is either unsaturated, saturated, fully saturated or aryl optionally substituted with one or more selected from the group consisting of hydroxy, alkyl, carboxy, hydroxyalkyl, carboxyalkyl, amino, aminoalkyl, cyano, alkoxy, alkoxycarbonyl, acyl, oxo, and halo.

5. The compound of claim 4 or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, lower alkyl, carboxy, carboxyalkoxy, heteroaryl, heterocycle, alkoxy, lower alkoxy, alkylamino, amino, dialkylamino, halogen, and —$NHSO_2R^2$, all of which can be optionally substituted by one or more selected from the group consisting of hydroxy, lower alkyl, hydroxyalkyl, aminoalkyl, amino, and halo;

$R^1$ is selected from the group consisting of lower alkyl, and aryl, wherein all may be substituted by one or more selected from the group consisting of hydroxy, alkyl, lower alkyl, carboxy, hydroxyalkyl, carboxyalkyl, amino, aminoalkyl, cyano, alkoxy, alkoxycarbonyl, acyl, oxo, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be selected from the group consisting of carboxy, and carboxymethoxy.

6. The compound of claim 4 or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, lower alkyl, carboxy, heteroaryl, heterocycle, lower alkoxy, dialkylamino, and halogen, all of which can be optionally substituted by one or more selected from the group consisting of hydroxy, lower alkyl, hydroxyalkyl, aminoalkyl, amino, acyl, carboxyalkoxy, alkoxycarbonyl, and halo;

$R^{2\beta}$, $R^{3\beta}$, $R^{4\beta}$, $R^{5\beta}$ and $R^{6\beta}$ are independently selected from the group consisting of hydrogen, lower alkyl, carboxy, heteroaryl, heterocycle, lower alkoxy, dialkylamino, acyl, alkoxycarbonyl, carboxyalkoxy, and halogen, all of which can be optionally substituted by one or more selected from the group consisting of hydroxy, lower alkyl, hydroxyalkyl, aminoalkyl, amino, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be carboxy or carboxymethoxy.

7. The compound of claim 4 or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, lower alkyl, carboxy, lower alkoxy, carboxyalkoxy, and halogen;

$R^{2\beta}$, $R^{3\beta}$, $R^{4\beta}$, $R^{5\beta}$ and $R^{6\beta}$ are independently selected from the group consisting of hydrogen, lower alkyl, heteroaryl, heterocycle, lower alkoxy, dialkylamino, and halogen all of which can be optionally substituted by one or more selected from the group consisting of hydroxy, methyl, hydroxymethyl, aminomethyl, amino, acyl, alkoxycarbonyl, and halo;

wherein one of $R^{4\beta}$, $R^{5\beta}$ or $R^{6\beta}$ must be a carbon-carbon linked heterocycle or heteroaryl;

with the proviso that at least one of $R^{2\alpha}$, $R^{3\alpha}$, or $R^{4\alpha}$ must be carboxy or carboxymethoxy.

8. The compound of claim 4 or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, lower alkyl, carboxy, lower alkoxy, carboxyalkoxy, and halogen;

$R^{2\beta}$, $R^{3\beta}$, $R^{4\beta2}$, $R^{5\beta}$ and $R^{6\beta}$ are independently selected from the group consisting of hydrogen, lower alkyl, heteroaryl, heterocycle, lower alkoxy, dialkylamino, and halogen;

wherein one of $R^{4\beta}$, $R^{5\beta}$ or $R^{6\beta}$ must be a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\alpha}$, $R^{3\alpha}$, or $R^{4\alpha}$ must be carboxy or carboxymethoxy.

9. The compound of claim 4 or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, lower alkyl, carboxy, lower alkoxy, carboxyalkoxy, and halogen;

$R^{2\beta}$, $R^{3\beta}$, $R^{4\beta}$, $R^{5\beta}$ and $R^{6\beta}$ are independently selected from the group consisting of hydrogen, lower alkyl, heteroaryl, heterocycle, lower alkoxy, dialkylamino, and halogen;

wherein one of $R^{4\beta}$, $R^{5\beta}$ or $R^{6\beta}$ must be a carbon-carbon linked heterocycle selected from the group consisting of pyrrolidinyl, pyranyl, tetrahydrofuranyl, tetrahydropyranyl, pyranyl, piperidinyl, and piperazinyl;

with the proviso that at least one of $R^{2\alpha}$, $R^{3\alpha}$, or $R^{4\alpha}$ must be carboxy or carboxymethoxy.

10. The compound of claim 4 or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, methyl, carboxy, carboxyalkoxy, methoxy, chloro and fluoro;

$R^{2\beta}$, $R^{3\beta}$, $R^{4\beta}$, $R^{5\beta}$ and $R^{6\beta}$ are independently selected from the group consisting of hydrogen, methyl, furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, isoquinolinyl, methoxy, dimethylamino, chloro and fluoro;

wherein one of $R^{4\beta}$, $R^{5\beta}$ or $R^{6\beta}$ must be a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\alpha}$, $R^{3\alpha}$, $R^{4\alpha}$, $R^{5\alpha}$ or $R^{6\alpha}$ must be carboxy or carboxymethoxy.

11. The compound of claim 4 or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen, methyl, carboxy, carboxyalkoxy, methoxy, chloro and fluoro;

$R^{2\beta}$, $R^{3\beta}$, $R^{4\beta}$, and $R^{6\beta}$ are independently selected from the group consisting of hydrogen, methyl, methoxy, dimethylamino, chloro and fluoro;

$R^{5\beta}$ is a carbon-carbon linked heteroaryl selected from the group consisting of furanyl, benzofuranyl, oxazolyl, thienyl, benzothienyl, indolyl, pyrrolyl, thiazolyl, imidazolyl, pyrimidinyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl;

with the proviso that at least one of $R^{2\beta}$, $R^{3\beta}$, or $R^{4\alpha}$ must be carboxy or carboxymethoxy.

12. The compound of claim 4 or its pharmaceutically acceptable salt or ester, wherein:

$R^{2\alpha}$, $R^{3\alpha}$, $R^{5\alpha}$, $R^{6\alpha}$ $R^{3\beta}$, and $R^{6\beta}$ are hydrogen;

$R^{4\alpha}$ is carboxy;

$R^{2\beta}$ and $R^{4\beta}$ are methoxy; and $R^{5\beta}$ is a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl.

13. The compound of claim 12 or its pharmaceutically acceptable salt or ester, wherein:

$R^{2\alpha}$, $R^{3\alpha}$, $R^{5\alpha}$, $R^{6\alpha}$, $R^{3\beta}$, and $R^{6\beta}$ are hydrogen;

$R^{4\alpha}$ is carboxy;

$R^{2\beta}$ and $R^{4\beta}$ are methoxy; and $R^{5\beta}$ is 5-(benzothien-2-yl).

14. The compound of claim 12 or its pharmaceutically acceptable salt or ester, wherein:

$R^{2\alpha}$, $R^{3\alpha}$, $R^{5\alpha}$, $R^{6\alpha}$, $R^{3\beta}$, and $R^{6\beta}$ are hydrogen;

$R^{4\alpha}$ is carboxy;

$R^{2\beta}$ and $R^{4\beta}$ are methoxy; and $R^{5\beta}$ is thienyl.

15. The compound of claim 12 or its pharmaceutically acceptable salt or ester, wherein:

$R^{2\alpha}$, $R^{3\alpha}$, $R^{5\alpha}$, $R^{6\alpha}$, $R^{3\beta}$, and $R^{6\beta}$ are hydrogen;

$R^{4\alpha}$ is carboxy;

$R^{2\beta}$ and $R^{4\beta}$ are methoxy; and $R^{5\beta}$ is indolyl.

16. The compound of claim 4 or its pharmaceutically acceptable salt or ester, wherein:

$R^{2\alpha}$, $R^{6\alpha}$, $R^{3\beta}$ and $R^{6\beta}$ are hydrogen;

$R^{4\alpha}$ is carboxymethoxy;

$R^{3\alpha}$, $R^{5\alpha}$, $R^{2\beta}$ and $R^{4\beta}$ are methoxy; and $R^{5\beta}$ is a carbon-carbon linked heteroaryl selected from the group consisting of furanyl, benzofuranyl, pyrimidinyl, oxazolyl, thienyl, benzothienyl, indolyl, pyrrolyl, thiazolyl, imidazolyl, pyrazolyl, isoxazolyl, 1,2,4-triazolyl, 1,2,3-triazolyl, pyridinyl, pyrazinyl, pyridazinyl, quinoxalinyl, phthalazinyl, benzimidazolyl, benzthiazolyl, benzoxazolyl, triazinyl, 1,2,4-oxadiazolyl, 1,3,4-oxadiazolyl, triazolopyridinyl, quinolinyl, purinyl, and isoquinolinyl.

17. The compound of claim 16 or its pharmaceutically acceptable salt or ester, wherein:

$R^{2\alpha}$, $R^{6\alpha}$, $R^{3\beta}$ and $R^{6\beta}$ are hydrogen;

$R^{4\alpha}$ is carboxymethoxy;

$R^{3\alpha}$, $R^{5\alpha}$, $R^{2\beta}$ and $R^{4\beta}$ are methoxy; and $R^{5\beta}$ is 5-(benzothien-2-yl).

18. The compound of claim 16 or its pharmaceutically acceptable salt or ester, wherein:

$R^{2\alpha}$, $R^{6\alpha}$, $R^{3\beta}$ and $R^{6\beta}$ are hydrogen;

$R^{4\alpha}$ is carboxymethoxy;

$R^{3\alpha}$, $R^{5\alpha}$, $R^{2\beta}$ and $R^{4\beta}$ are methoxy; and $R^{5\beta}$ is thienyl.

19. The compound of claim 16 or its pharmaceutically acceptable salt or ester, wherein:

$R^{2\alpha}$, $R^{6\alpha}$, $R^{3\beta}$ and $R^{6\beta}$ are hydrogen;

$R^{4\alpha}$ is carboxymethoxy;

$R^{3\alpha}$, $R^{5\alpha}$, $R^{2\beta}$ and $R^{4\beta}$ are methoxy; and $R^{5\beta}$ is indolyl.

20. The compound of claim 1 wherein the compound is selected from the group consisting of 4-[3-(2,4-dimethoxy-5-thiophen-2-yl-phenyl)-propynoyl]-benzoic acid methyl ester, 4-[3-{2,4-Dimethoxy-5-(thiophen-2-yl)-phenyl}propynoyl]-benzoic acid, {4-[3-(2,4-Dimethoxy-5-thiophen-2-yl-phenyl)-propynoyl]-2,6-dimethoxy-phenoxy}-acetic acid methyl ester, and {4-[3-(2,4-Dimethoxy-5-thiophen-2-yl-phenyl)-propynoyl]-2,6-dimethoxy-phenoxy}-acetic acid.

21. A pharmaceutical composition comprising a therapeutically effective amount of a compound of claim 1, 2, 3, 4, 5, 6, 7, 8, 9, 10, 11, 12, 13, 14, 15, 16, 17, 18, 19 or 20 together with one or more pharmaceutically acceptable carrier.

22. A method for the treatment of an inflammatory disorder mediated by VCAM-1, comprising administering amount of a compound of claim 1, 2, 3, 4, 5, 6, 7, 8, 9, 10, 11, 12, 13, 14, 15, 16, 17, 18, 19 or 20, wherein the disorder is arthritis.

23. A method for the treatment of an inflammatory disorder mediated by VCAM-1, comprising administering an effective amount of a compound of claim 1, 2, 3, 4, 5, 6, 7, 8, 9, 10, 11, 12, 13, 14, 15, 16, 17, 18, 19 or 20, wherein the disorder is rheumatoid arthritis.

24. A method for the treatment of an inflammatory disorder mediated by VCAM-1, comprising administering an effective amount of a compound of claim 1, 2, 3, 4, 5, 6, 7, 8, 9, 10, 11, 12, 13, 14, 15, 16, 17, 18, 19 or 20, wherein the disorder is asthma.

25. A method for the treatment of an inflammatory disorder mediated by VCAM-1, comprising administering an effective amount of a compound of claim 1, 2, 3, 4, 5, 6, 7, 8, 9, 10, 11, 12, 13, 14, 15, 16, 17, 18, 19 or 20, wherein the disorder is allergic rhinitis.

* * * * *